US007361767B2

(12) United States Patent
Benson et al.

(10) Patent No.: US 7,361,767 B2
(45) Date of Patent: Apr. 22, 2008

(54) N-SULFONYLDICARBOXIMIDE CONTAINING TETHERING COMPOUNDS

(75) Inventors: Karl E. Benson, St. Paul, MN (US); Moses M. David, Woodbury, MN (US); Cary A. Kipke, Woodbury, MN (US); Brinda B. Lakshmi, Woodbury, MN (US); Charles M. Leir, Falcon Heights, MN (US); George G. Moore, Afton, MN (US); Rahul Shah, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 143 days.

(21) Appl. No.: 10/714,053

(22) Filed: Nov. 14, 2003

(65) Prior Publication Data

US 2005/0106709 A1 May 19, 2005

(51) Int. Cl.
*C07D 207/48* (2006.01)
*C07D 209/48* (2006.01)
*C07D 211/96* (2006.01)
*C07D 403/12* (2006.01)

(52) U.S. Cl. ............... 546/219; 548/261; 548/435; 548/514; 548/542

(58) Field of Classification Search ........... 546/219; 548/261, 435, 514, 542
See application file for complete search history.

(56) References Cited

U.S. PATENT DOCUMENTS

| 4,233,029 | A | | 11/1980 | Columbus et al. | |
|---|---|---|---|---|---|
| 5,238,950 | A | * | 8/1993 | Clader et al. | 514/360 |
| 5,246,846 | A | * | 9/1993 | Pittner et al. | 435/174 |
| 5,674,742 | A | | 10/1997 | Northrup et al. | |
| 5,888,594 | A | | 3/1999 | David et al. | |
| 5,948,166 | A | | 9/1999 | David et al. | |
| 6,156,270 | A | | 12/2000 | Buechler et al. | |
| 6,369,893 | B1 | | 4/2002 | Christel et al. | |
| 6,656,428 | B1 | | 12/2003 | Clark et al. | |
| 2003/0170881 | A1 | | 9/2003 | Davis et al. | |

FOREIGN PATENT DOCUMENTS

| EP | 0 657 737 | 6/1995 |
|---|---|---|
| JP | 53 063375 | 6/1978 |
| WO | WO 02/088296 | 11/2002 |
| WO | WO02/094890 | 11/2002 |
| WO | WO03/068712 | 8/2003 |
| WO | WO2004/067732 | 8/2004 |

OTHER PUBLICATIONS

Lukovits, Journal of the Chemical Society, Perkin Transactions 2, 9, 1667-1671, 1988.*
Bozhinov et al., Chemical Abstracts, 117:235734, 1992.*
Kharasch et al., Chemical Abstracts, 47:1656c-i, 1953.*
Webb et al., Chemical Abstracts, 83:189238, 1975.*
Yamahara et al., Chemical Abstracts 133:357243, 2000.*
Kato et al., Chemical Abstracts, 120:65816, 1994.*
Grate et al., "Acoustic Wave Sensors" vol. 2, pp. 38-83, 1996 (XP002334970).
Database Caplus Online? Chemical Abstracts Service, Columbus, Ohio, US; Lukovits, Istvan: "Decomposition of Wiener Topological Index. Application to Drug-receptor Interactions" XP002321504.
M. David et al., "*Plasma Deposition and Etching of Diamond-Like Carbon Films*", *AIChE Journal,* 37 (3), 367-376 (Mar. 1991).
R.R. Shah et al., "*Using Liquid Crystals to Image Reactants and Products of Acid-Base Reactions on Surfaces with Micrometer Resolution*", *J. Am. Chem. Soc.,* 1999, 121, 11300-11310.
J. Lahiri et al., "*Patterning Ligands on Reactive SAMS by Microcontact Printing*", *Langmuir,* 1999, 15, 2055-2060.
R.R. Shah et al., "*Principles for Measurement of Chemical Exposure Based on Recognition-Driven Anchoring Transitions in Liquid Crystals*", *Science,* 2001, 293, 1296.
M. Niculescu et al., "*Redox Hydrogel-Based Amperometric Bienzyme Electrodes for Fish Freshness Monitoring*", *Anal. Chem.* 2000, 72, 1591-1597.
J. Wang et al. "*Ultrathin Porous Carbon Films as Amperometric Transducers for Biocatalytic Sensors*",*Anal. Chem.* 1994, 66, 1988-1992.
P. Wagner et al., "*Covalent Immobilization of Native Biomolecules onto Au(111) via N-Hydroxysuccinimide Ester Functionalized Self-Assembled Monolayers for Scanning Probe Microscopy*", *Biophysical. Journal,* 1996, vol. 70, 2052-2066.

* cited by examiner

*Primary Examiner*—Fiona T. Powers
(74) *Attorney, Agent, or Firm*—Jean A. Lown

(57) ABSTRACT

Compounds having two reactive functional groups are described that can be used as a tethering compound to immobilize an amine-containing material to a substrate. The first reactive functional group can be used to provide attachment to a surface of a substrate. The second reactive functional group is a N-sulfonyldicarboximide group that can be reacted with an amine-containing material, particularly a primary aliphatic amine, to form a connector group between the substrate and the amine-containing material. The invention also provides articles and methods for immobilizing amine-containing materials to a substrate.

8 Claims, 2 Drawing Sheets

N-SULFONYLDICARBOXIMIDE CONTAINING TETHERING COMPOUNDS

FIELD OF THE INVENTION

This invention provides compounds that include both a substrate-reactive group and a N-sulfonyldicarboximide group. The invention also provides articles and methods for immobilizing amine-containing materials to a substrate.

BACKGROUND

Amine-containing materials such as amine-containing analytes, amino acids, peptides, DNA fragments, RNA fragments, protein fragments, organelles, and immunoglobins immobilized on the surface of a substrate can be used in numerous applications. For example, immobilized biological amines can be used for the medical diagnosis of a disease or genetic defect, for biological separations, or for detection of various biomolecules.

The attachment of amine-containing materials to a substrate is often achieved through the use of a tethering compound. A tethering compound usually has two reactive functional groups separated by a linking group. One of the functional groups provides a means for anchoring the tethering compound to a substrate by reacting with a complementary functional group on the surface of the substrate. A second reactive functional group can be selected to react with an amine-containing material. The second reactive functional group can be, for example, an activated acyl derivative, such as an N-hydroxysuccinimide ester, or a cyclic azlactone. An amine-containing material can react with the N-hydroxysuccinimide ester to form a carboxamide resulting in the displacement of an N-hydroxysuccinimide fragment. An amine-containing material can react with the cyclic azlactone resulting in the opening of the ring structure.

Although tethering compounds that include a group such as an N-hydroxysuccinimide ester or a cyclic azlactone can be highly reactive with primary amine-containing materials, such tethering compounds can suffer from a number of disadvantages. Many of the reactions with biological amines are conducted in dilute aqueous solutions. Under these conditions, the N-hydroxysuccinimide ester functional group is known to undergo rapid hydrolysis. This competing reaction can cause incomplete or inefficient immobilization of the amine-containing materials on the substrate. While cyclic azlactone functional groups are more stable to hydrolysis, cyclic azlactone groups tend to be synthetically incompatible with many groups that could be used to attach the tethering compound to a substrate.

SUMMARY

Compounds are provided that can function as tethering compounds for immobilizing an amine-containing material to a substrate. More specifically, the compounds include two types of reactive functional groups. The first type of reactive functional group is a substrate-reactive group capable of reacting with a complementary functional group on a surface of the substrate resulting in the attachment of a tethering group to the substrate. The second type of reactive functional group is a N-sulfonyldicarboximide derivative that can react with an amine-containing material by a ring opening reaction. A connector group is formed between the amine-containing material and the substrate. Articles and methods for immobilizing amine-containing materials to a substrate are also provided.

In one aspect of the invention, compounds are provided. The compounds can be of Formula I:

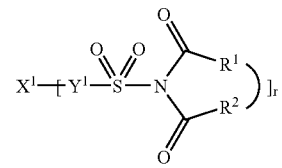

I where
$X^1$ is a substrate-reactive functional group selected from a carboxy, halocarbonyl, halocarbonyloxy, cyano, hydroxy, mercapto, isocyanato, halosilyl, alkoxysilyl, acyloxysilyl, azido, aziridinyl, haloalkyl, tertiary amino, primary aromatic amino, secondary aromatic amino, disulfide, alkyl disulfide, benzotriazolyl, phosphono, phosphoroamido, phosphate, or ethylenically unsaturated group;
$Y^1$ is a single bond or a divalent group selected from an alkylene, heteroalkylene, arylene, carbonyl, carbonyloxy, carbonylimino, oxy, thio, $-NR^d-$ where $R^d$ is hydrogen or alkyl, or combinations thereof;
$R^1$ and $R^2$ together with a dicarboximide group to which they are attached form a four to eight membered heterocyclic or heterobicyclic group that can be fused to an optional aromatic group, optional saturated or unsaturated cyclic group, or optional saturated or unsaturated bicyclic group; and
r is equal to 1 when $X^1$ is a monovalent group or equal to 2 when $X^1$ is a divalent group. The compounds of Formula I can be unsubstituted or substituted with a halo, alkyl, alkoxy, or combinations thereof.

The compounds also can be according to Formula II:

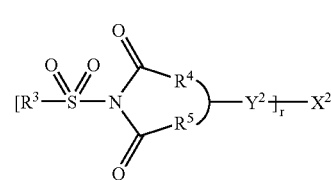

II where
$X^2$ is a substrate-reactive functional group selected from a carboxy, halocarbonyl, halocarbonyloxy, cyano, hydroxy, mercapto, isocyanato, halosilyl, alkoxysilyl, acyloxysilyl, azido, aziridinyl, haloalkyl, tertiary amino, primary aromatic amino, secondary aromatic amino, disulfide, alkyl disulfide, benzotriazolyl, phosphono, phosphoroamido, phosphato, or ethylenically unsaturated group;
$R^4$ and $R^5$ together with a dicarboximide group to which they are attached form a four to eight membered heterocyclic or heterobicyclic group that can be fused to an optional aromatic group, optional saturated or unsaturated cyclic group, or optional saturated or unsaturated bicyclic group;
$Y^2$ is a single bond or a divalent group selected from an alkylene, heteroalkylene, arylene, carbonyl, carbonyloxy, carbonylimino, oxy, thio, $-NR^d-$ where $R^d$ is hydrogen or alkyl, or combinations thereof;

$R^3$ is an alkyl, aryl, aralkyl, or —$NR^b R^c$ wherein $R^b$ and $R^c$ are each an alkyl group or taken together with the nitrogen atom to which they are attached form a four to eight heterocyclic group; and r is equal to 1 when $X^2$ is monovalent or equal to 2 when $X^2$ is a divalent group. The compounds of Formula II can be unsubstituted or substituted with a halo, alkyl, alkoxy, or combinations thereof.

Another aspect of the invention provides articles. In one embodiment, the articles include a tethering group attached to a substrate. The tethering group is the reaction product of the substrate-reactive group $X^1$ in compounds of Formula I or $X^2$ in compound of Formula II with a complementary functional group on the surface of the substrate to form an ionic bond, covalent bond, or combinations thereof. The substrate-attached tethering group has an N-sulfonyldicarboximide group capable of reacting with an amine-containing material. In another embodiment, the articles include an amine-containing material immobilized to a substrate through a connector group.

Yet another aspect of the invention provides a method of immobilizing an amine-containing material to a substrate. The method involves preparing a substrate-attached tethering group by reacting the substrate-reactive group $X^1$ in compounds of Formula I or $X^2$ in compounds of Formula II with a complementary functional group on a surface of a substrate; and reacting a N-sulfonyldicarboximide group of the substrate-attached tethering group with an amine-containing material to form a connector group between the amine-containing material and the substrate.

The above summary of the present invention is not intended to describe each disclosed embodiment or every implementation of the present invention. The detailed description that follows more particularly exemplifies these embodiments.

BRIEF DESCRIPTION OF THE DRAWINGS

The above aspects may be more completely understood in consideration of the following detailed description of various embodiments in connection with the accompanying drawings, in which.

Figure 1:
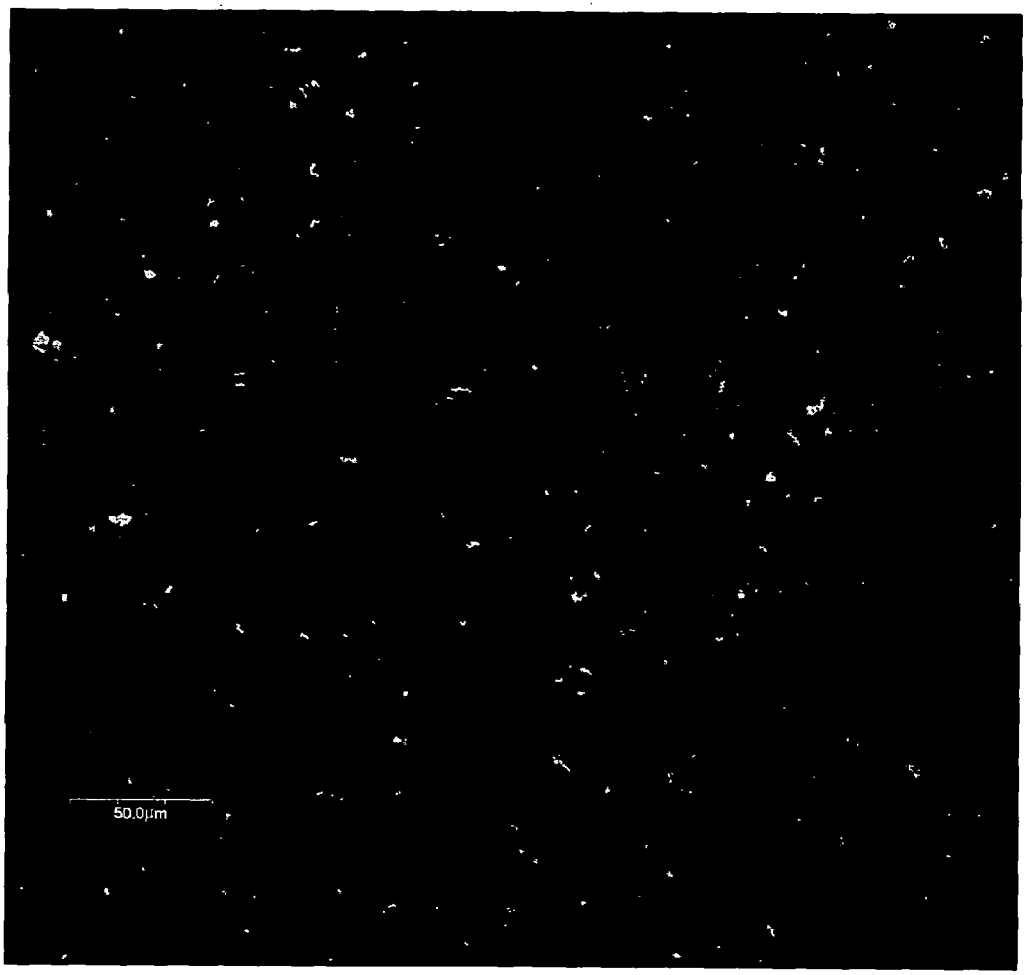
FIG. 1 is a confocal micrograph showing the capture of *Staphylococcus aureus* with immobilized IgG on a multilayer substrate of diamond-like glass/diamond-like carbon/polyimide/diamond-like carbon/diamond-like glass with a connector group derived from a tethering compound of the invention.

While the invention is amenable to various modifications and alternative forms, specifics thereof have been shown by way of example in the drawings will be described in detail. It should be understood, however, that the intention is not to limit the invention to the particular embodiments described. To the contrary, the intention is to cover all modifications, equivalents, and alternatives falling within the spirit and scope of the present disclosure.

DETAILED DESCRIPTION

Compounds having two reactive functional groups are described that can be used to immobilize amine-containing materials to a substrate. The first reactive functional group can be used to provide attachment to a surface of the substrate. The second reactive functional group is a N-sulfonyldicarboximide derivative that can be reacted with an amine-containing material, particularly a primary aliphatic amine-containing material, resulting in the formation of a connector group between the substrate and the amine-containing material. The invention also provides articles and methods for immobilizing amine-containing materials to a substrate.

Definitions

As used herein, the terms "a", "an", and "the" are used interchangeably with "at least one" to mean one or more of the elements being described.

As used herein, the term "acyl" refers to a monovalent group of formula —(CO)R where R is an alkyl group and where (CO) used herein indicates that the carbon is attached to the oxygen with a double bond.

As used herein, the term "acyloxy" refers to a monovalent group of formula —O(CO)R where R is an alkyl group.

As used herein, the term "acyloxysilyl" refers to a monovalent group having an acyloxy group attached to a Si (i.e., Si—O(CO)R where R is an alkyl). For example, an acyloxysilyl can have a formula —Si[O(CO)R]$_{3-n}$L$_n$ where n is an integer of 0 to 2 and L is a halogen or alkoxy. Specific examples include —Si[O(CO)CH$_3$]$_3$, —Si[O(CO)CH$_3$]$_2$Cl, or —Si[O(CO)CH$_3$]Cl$_2$.

As used herein, the term "alkoxy" refers to a monovalent group of formula —OR where R is an alkyl group.

As used herein, the term "alkoxycarbonyl" refers to a monovalent group of formula —(CO)OR where R is an alkyl group.

As used herein, the term "alkoxysilyl" refers to a group having an alkoxy group attached to a Si (i.e., Si—OR where R is an alkyl). For example, an alkoxysilyl can have a formula —Si(OR)$_{3-n}$(L$^a$)$_n$ where n is an integer of 0 to 2 and L$^a$ is a halogen or acyloxy. Specific examples include —Si(OCH$_3$)$_3$, —Si(OCH$_3$)$_2$Cl, or —Si(OCH$_3$)Cl$_2$.

As used herein, the term "alkyl" refers to a monovalent radical of an alkane and includes groups that are linear, branched, cyclic, or combinations thereof. The alkyl group typically has 1 to 30 carbon atoms. In some embodiments, the alkyl group contains 1 to 20 carbon atoms, 1 to 10 carbon atoms, 1 to 6 carbon atoms, or 1 to 4 carbon atoms. Examples of alkyl groups include, but are not limited to, methyl, ethyl, n-propyl, isopropyl, n-butyl, isobutyl, tert-butyl, n-pentyl, n-hexyl, cyclohexyl, n-heptyl, n-octyl, and ethylhexyl.

As used herein, the term "alkyl disulfide" refers to a monovalent group of formula —SSR where R is an alkyl group.

As used herein, the term "alkylene" refers to a divalent radical of an alkane. The alkylene can be straight-chained, branched, cyclic, or combinations thereof. The alkylene typically has 1 to 200 carbon atoms. In some embodiments, the alkylene contains 1 to 100, 1 to 80, 1 to 50, 1 to 30, 1 to 20, 1 to 10, 1 to 6, or 1 to 4 carbon atoms. The rad centers of the alkylene can be on the same carbon atom (i.e., an alkylidene) or on different carbon atoms.

As used herein, the term "aralkyl" refers to a monovalent radical of the compound R—Ar where Ar is an aromatic carbocyclic group and R is an alkyl group.

As used herein, the term "aralkylene" refers to a divalent radical of formula —R—Ar— where Ar is an arylene group and R is an alkylene group.

As used herein, the term "aryl" refers to a monovalent aromatic carbocyclic radical. The aryl can have one aromatic ring or can include up to 5 carbocyclic ring structures that are connected to or fused to the aromatic ring. The other ring structures can be aromatic, non-aromatic, or combinations thereof. Examples of aryl groups include, but are not limited to, phenyl, biphenyl, terphenyl, anthryl, naphthyl, acenaphthyl, anthraquinonyl, phenanthryl, anthracenyl, pyrenyl, perylenyl, and fluorenyl.

As used herein, the term "arylene" refers to a divalent radical of a carbocyclic aromatic compound having one to five rings that are connected, fused, or combinations thereof. In some embodiments, the arylene group has up to 5 rings, up to 4 rings, up to 3 rings, up to 2 rings, or one aromatic ring. For example, the arylene group can be phenylene.

As used herein, the term "azido" refers to a monovalent group of formula —$N_3$.

As used herein, the term "aziridinyl" refers to a cyclic monovalent radical of aziridine having the formula

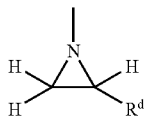

where $R^d$ is hydrogen or alkyl.

As used herein, the term "benzotriazolyl" refers to a monovalent group having a benzene group fused to a triazolyl group. The formula for a benzotriazolyl group is $C_6H_4N_3$—.

As used herein, the term "carbonyl" refers to a divalent group of formula —(CO)—.

As used herein, the term "carbonylimino" refers to a divalent group of formula —(CO)$NR^a$— where $R^a$ is hydrogen, alkyl, or aryl.

As used herein, the term "carbonyloxy" refers to a divalent group of formula —(CO)O—.

As used herein, the term "carbonyloxycarbonyl" refers to a divalent group of formula —(CO)O(CO)—. Such a group is part of an anhydride compound.

As used herein, the term "carbonylthio" refers to a divalent group of formula —(CO)S—.

As used herein, the term "carboxy" refers to a monovalent group of formula —(CO)OH or a salt thereof.

As used herein, the term "cyano" refers to a group of formula —CN.

As used herein, the term "dicarboximide" refers to a trivalent group of formula

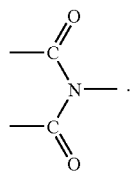

As used herein, the term "disulfide" refers to a divalent group of formula —S—S—.

As used herein, the term "ethylenically unsaturated" refers to a monovalent group having a carbon-carbon double bond of formula —CY=$CH_2$ where Y is hydrogen, alkyl, or aryl.

As used herein, the term "halo" refers to a halogen selected from F, Cl, Br, or I.

As used herein, the term "haloalkyl" refers to an alkyl having at least one hydrogen atom replaced with a halogen selected from F, Cl, Br, or I. Perfluoroalkyl groups are a subset of haloalkyl groups.

As used herein, the term "halocarbonyloxy" refers to a monovalent group of formula —O(CO)X where X is a halogen atom selected from F, Cl, Br, or I.

As used herein, the term "halocarbonyl" refers to a monovalent group of formula —(CO)X where X is a halogen atom selected from F, Cl, Br, or I.

As used herein, the term "halosilyl" refers to a group having a Si attached to a halogen (i.e., Si—X where X is a halogen). For example, the halosilyl group can be of formula —$SiX_{3-n}(L^b)_n$ where n is an integer of 0 to 2 and $L^b$ is selected from an alkoxy, or acyloxy. Some specific examples include the groups —$SiCl_3$, —$SiCl_2OCH_3$, and —$SiCl(OCH_3)_2$.

As used herein, the term "heteroalkylene" refers to a divalent alkylene having one or more carbon atoms replaced with a sulfur, oxygen, or $NR^d$ where $R^d$ is hydrogen or alkyl. The heteroalkylene can be linear, branched, cyclic, or combinations thereof and can include up to 400 carbon atoms and up to 30 heteroatoms. In some embodiments, the heteroalkylene includes up to 300 carbon atoms, up to 200 carbon atoms, up to 100 carbon atoms, up to 50 carbon atoms, up to 30 carbon atoms, up to 20 carbon atoms, or up to 10 carbon atoms.

As used herein, the term "hydroxy" refers to a group of formula —OH.

As used herein, the term "isocyanato" refers to a group of formula —NCO.

As used herein, the term "mercapto" refers to a group of formula —SH.

As used herein, the term "N-sulfonyldicarboximide" refers to a trivalent entity of formula

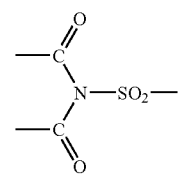

As used herein, the term "oxycarbonylimino" refers to a divalent group of formula —O(CO)$NR^a$— where $R^a$ is hydrogen, alkyl, or aryl.

As used herein, the term "oxy" refers to a divalent group of formula —O—.

As used herein, the term "oxycarbonyloxy" refers to a divalent group of formula —O(CO)O—.

As used herein, the term "oxycarbonylthio" refers to a divalent group of formula —O(CO)S—.

As used herein, the term "perfluoroalkyl" refers to an alkyl group in which all of the hydrogen atoms are replaced with fluorine atoms.

As used herein, the term "phosphate" refers to a monovalent group of formula —$OPO_3H_2$.

As used herein, the term "phosphono" refers to a monovalent group of formula —$PO_3H_2$.

As used herein, the term "phosphoramido" refers to a monovalent group of formula —$NHPO_3H_2$.

As used herein, the term "primary aromatic amino" refers to a monovalent group of formula —$ArNH_2$ where Ar is an aryl group.

As used herein, the term "secondary aromatic amino" refers to a monovalent group of formula —ArNR$^d$H where Ar is an aryl group and R$^e$ is an alkyl or aryl.

As used herein, the term "tertiary amino" refers to a group of formula —NR$_2$ where R is an alkyl.

As used herein, the term "thio" refers to a group of formula —S—.

As used herein, the term "thiocarbonylimino" refers to a divalent group of formula —S(CO)NR$^a$— where R$^a$ is hydrogen, alkyl, or aryl.

As used herein, the term "attachment group" refers to the group formed by reaction of a substrate-reactive group in a compound according to Formula I with a complementary functional group on the surface of a substrate.

As used herein, the term "complementary functional group" refers to a group capable of reacting with a recited group to form an ionic bond, covalent bond, or combinations thereof. For example, the complementary functional group can be a group on a substrate capable of reacting with group X$^1$ in Formula I or with group X$^2$ in Formula II.

As used herein, the term "connector group" refers to a group linking a substrate to an immobilized amine-containing material. The attachment group is part of the connector group.

As used herein, the term "room temperature" refers to a temperature of about 20° C. to about 25° C. or about 22° C. to about 25° C.

As used herein, the term "substrate" refers to a solid phase support to which tethering groups can be attached (i.e., the substrate has a group capable of reacting with a tethering compound). The substrates can have any useful form including, but not limited to, thin films, sheets, membranes, filters, nonwoven or woven fibers, hollow or solid beads, bottles, plates, tubes, rods, pipes, or wafers. The substrates can be porous or non-porous, rigid or flexible, transparent or opaque, clear or colored, or reflective or non-reflective. Suitable substrate materials include polymeric materials, glasses, silicons, ceramics, metals, metal oxides, or combinations thereof.

As used herein, the term "tethering compound" refers to a compound that has two reactive groups. One of the reactive groups (i.e., the substrate-reactive functional group) can react with a complementary functional group on the surface of a substrate to form a tethering group. The other reactive group (i.e., the N-sulfonyldicarboximide group) can react with an amine-containing material. Reaction of both reactive groups of the tethering compound results in the formation of a connector group between the substrate and the amine-containing material (i.e., the amine-containing material can be immobilized on the substrate).

As used herein, the term "tethering group" refers to a group attached to a substrate that results from the reaction of the substrate-reactive group on the tethering compound with a complementary functional group on a surface of a substrate. The tethering group includes a group that can react with an amine-containing material (i.e., the tethering group includes a N-sulfonyldicarboximide group).

As used herein, a curve connecting two groups in a formula indicates that the two groups together form part of a cyclic structure.

Compounds

One aspect of the invention provides compounds that can be used as tethering compounds for immobilizing an amine-containing material to a substrate. The compounds include both a substrate-reactive group and a N-sulfonyldicarboximide group. The substrate-reactive group can be used for attachment to the substrate and the N-sulfonyldicarboximide group can be reacted with an amine-containing material resulting in the formation of a connector group between the amine-containing material and the substrate.

In one embodiment, the compounds are of Formula I:

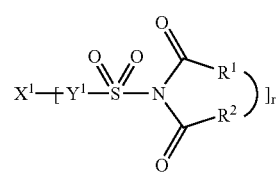

where

X$^1$ is a substrate-reactive functional group selected from a carboxy, halocarbonyl, halocarbonyloxy, cyano, hydroxy, mercapto, isocyanato, halosilyl, alkoxysilyl, acyloxysilyl, azido, aziridinyl, haloalkyl, tertiary amino, primary aromatic amino, secondary aromatic amino, disulfide, alkyl disulfide, benzotriazolyl, phosphono, phosphoroamido, phosphato, or ethylenically unsaturated group;

Y$^1$ is a single bond or a divalent group selected from an alkylene, heteroalkylene, arylene, carbonyl, carbonyloxy, carbonylimino, oxy, thio, —NR$^d$— where R$^d$ is hydrogen or alkyl, or combinations thereof;

R$^1$ and R$^2$ together with a dicarboximide group to which they are attached form a four to eight membered heterocyclic or heterobicyclic group that can be fused to an optional aromatic group, optional saturated or unsaturated cyclic group, or optional saturated or unsaturated bicyclic group; and r is equal to 1 when X$^1$ is a monovalent group or equal to 2 when X$^1$ is a divalent group. The compounds of Formula I can be unsubstituted or substituted with a halo, alkyl, alkoxy, or combinations thereof.

The reactive functional group X$^1$ typically does not react with the N-sulfonyldicarboximide group in Formula I and can be used, for example, to provide attachment to a substrate by reacting with a complementary functional group on a surface of a substrate. That is, X$^1$ can react with a complementary functional group to form a substrate-attached tethering group. X$^1$ can be monovalent or divalent. When X$^1$ is divalent, r is equal to 2 and the compounds of Formula I have the following structure:

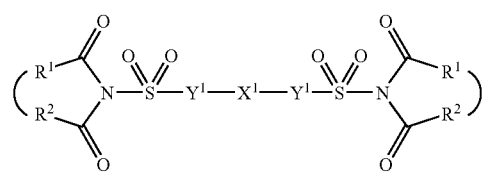

that can be symmetrical about X$^1$. A disulfide is an exemplary divalent X$^1$ group. When X$^1$ is monovalent, r in Formula II is equal to 1 and the compounds have the following structure:

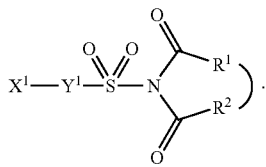

Suitable monovalent $X^1$ groups include a carboxy, halocarbonyl, halocarbonyloxy, cyano, hydroxy, mercapto, isocyanato, halosilyl, alkoxysilyl, acyloxysilyl, azido, aziridinyl, haloalkyl, tertiary amino, primary aromatic amino, secondary aromatic amino, disulfide, alkyl disulfide, benzotriazolyl, phosphono, phosphoroamido, phosphate, or ethylenically unsaturated group.

The $X^1$ groups typically can react with a complementary functional group on the surface of a substrate to form a stable ionic bond, covalent bond, or combination thereof. Suitable $X^1$ groups for attachment to the surface of a polymeric substrate include a carboxy, halocarbonyl, halocarbonyloxy, cyano, hydroxy, mercapto, isocyanato, halosilyl, alkoxysilyl, acyloxysilyl, azido, aziridinyl, haloalkyl, tertiary amino, primary aromatic amino, secondary aromatic amino, or ethylenically unsaturated group. Suitable $X^1$ groups for attachment to the surface of a gold-containing substrate include mercapto, disulfide, or alkyl disulfide. Suitable $X^1$ groups for attachment to the surface of other metal-containing substrates include benzotriazolyl, phosphono, phosphoroamido, or phosphato groups. Suitable $X^1$ groups for attachment to glass or ceramic-containing substrates as well as to metal oxide-containing or hydrated metal oxide-containing substrates include halosilyl, alkoxysilyl, or acyloxysilyl groups.

The group $Y^1$ in Formula I can be a single bond or a divalent group selected from an alkylene, heteroalkylene, arylene, carbonyl, carbonyloxy, carbonylimino, oxy, thio, —$NR^d$— where $R^d$ is hydrogen or alkyl, or combinations thereof. Suitable heteroalkylenes can contain 1 to 400 carbon atoms and up to 30 heteroatoms selected from N, O, S, or combinations thereof. Suitable alkylenes can contain 1 to 200 carbon atoms. The heteroalkylene and alkylene groups can be linear, branched, cyclic, or combinations thereof.

The group $Y^1$ in Formula I often includes an arylene group attached directly to the sulfonyl group as shown in the following structure:

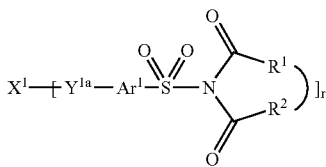

where $Ar^1$ is an arylene group and $Y^{1a}$ is a single bond or a divalent group selected from alkylene, heteroalkylene, carbonyl, carbonyloxy, carbonylimino, oxy, thio, —$NR^d$— where $R^d$ is hydrogen or alkyl, or combinations thereof. The groups $X^1$, r, $R^1$, and $R^2$ are the same as previously defined for Formula I. The compounds can be unsubstituted or substituted with a halo, alkyl, alkoxy, or combinations thereof. In some embodiments, the arylene group is phenylene. In some examples, $Ar^1$ is phenylene and $Y^{1a}$ is a single bond (i.e., $X^1$ is attached directly to the phenylene group).

The group $Y^1$ can include a first alkylene group linked to an arylene group with a group selected from a carbonyl, carbonyloxy, carbonylimino, oxy, thio, or —$NR^d$— where $R^d$ is hydrogen or alkyl. The first alkylene group can be further linked to a second alkylene or a first heteroalkylene group with a group selected from a carbonyl, carbonyloxy, carbonylimino, oxy, thio, or —$NR^d$— where $R^d$ is hydrogen or alkyl. Additional alkylene or heteroalkylene groups can be linked to the second alkylene or to the first heteroalkylene group with a group selected from a carbonyl, carbonyloxy, carbonylimino, oxy, thio, or —$NR^d$— where $R^d$ is hydrogen or alkyl. For example, $Y^1$ in Formula I can include an alkylene group linked to an arylene group by a carbonyloxy or carbonylimino group as in the following formulas:

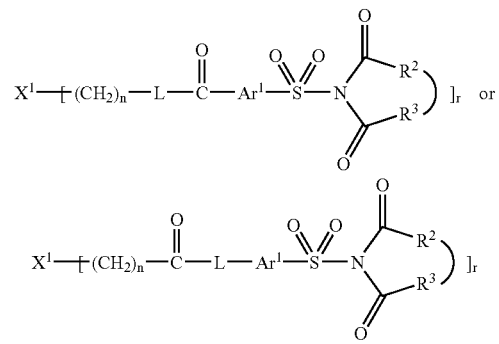

where n is an integer of 1 to 100; $Ar^1$ is an arylene group; and L is oxygen or $NR^d$ where $R^d$ is hydrogen or alkyl. Exemplary compounds include those where n is an integer no greater than 80, no greater than 60, no greater than 40, no greater than 20, or no greater than 10; and $Ar^1$ is phenylene. The groups $X^1$, r, $R^1$, and $R^2$ are the same as previously defined for Formula I. The compounds can be unsubstituted or substituted with a halo, alkyl, alkoxy, or combinations thereof.

In another example, the group $Y^1$ can include a first heteroalkylene group linked to an arylene with a group selected from a carbonyl, carbonyloxy, carbonylimino, oxy, thio, or —$NR^d$— where $R^d$ is hydrogen or alkyl. The first heteroalkylene group can be further linked to a second heteroalkylene or to a first alkylene group with a group selected from a carbonyl, carbonyloxy, carbonylimino oxy, thio, or —$NR^d$— where $R^d$ is hydrogen or alkyl. Additional alkylene or heteroalkylene groups can be linked to the second heteroalkylene or to the first alkylene group with groups selected from carbonyl, carbonyloxy, carbonylimino group, oxy, thio, —$NR^d$— where $R^d$ is hydrogen or alkyl, or combinations thereof. For example, the compounds can have the following structure:

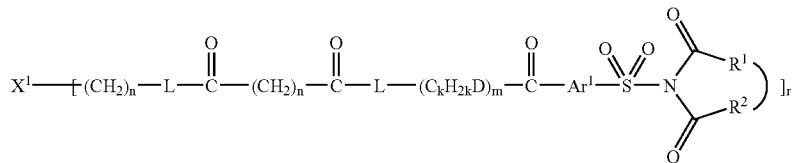

where each n is independently an integer of 1 to 100; m is an integer of 1 to 200; $Ar^1$ is an arylene group; k is an integer of 2 to 4; D is oxygen, sulfur, or NH; and L is oxygen or $NR^d$ where $R^d$ is hydrogen or alkyl. In some compounds, each n is independently an integer no greater than 80, no greater than 60, no greater than 40, no greater than 20, or no greater than 10; and m is an integer no grater than 150, no greater than 100, no greater than 80, no greater than 60, no greater than 40, no greater than 20, or no greater than 10. Exemplary compounds include those where D is oxygen; k is equal to 2; and $Ar^1$ is phenylene. The groups $X^1$, r, $R^1$, and $R^2$ are the same as previously defined for Formula I. The compounds can be unsubstituted or substituted with a halo, alkyl, alkoxy, or combinations thereof.

The $Y^1$ group can be a single bond. For example, in the following formula, $Y^1$ is a single bond when $X^1$ is a primary or secondary aromatic amino group

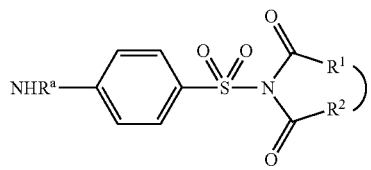

where $R^a$ is hydrogen, alkyl, or aryl. The groups $R^1$ and $R^2$ are the same as previously defined for Formula II. The compounds can be unsubstituted or substituted with a halo, alkyl, alkoxy, or combinations thereof.

In some embodiments, $Y^1$ does not include an arylene group. For example, $Y^1$ can be an alkylene group. In another example, a first alkylene group can be connected to a second alkylene group or to a first heteroalkylene group with a group selected from a carbonyl, carbonylimino, carbonyloxy, oxy, thio, or $-NR^d-$ where $R^d$ is hydrogen or alkyl. Additional alkylene or heteroalkylene groups can be connected to the second alkylene group or the first heteroalkylene group with a group selected from a carbonyl, carbonylimino, carbonyloxy, oxy, thio, or $-NR^d-$ where $R^d$ is hydrogen or alkyl. In another example, $Y^1$ can be a heteroalkylene group. In yet another example, a first heteroalkylene group can be connected to a second heteroalkylene group or to a first alkylene group with a carbonyl, carbonylimino, carbonyloxy, oxy, thio, or $-NR^d-$ where $R^d$ is hydrogen or alkyl. Additional alkylene or heteroalkylene groups can be connected to the second heteroalkylene group or the first alkylene group.

In Formula I, $R^1$ and $R^2$ together with the dicarboximide group to which they are attached form a four to eight membered heterocyclic or heterobicyclic group that can be fused to an optional aromatic, optional saturated or unsaturated cyclic group, or optional saturated or unsaturated bicyclic group. The optional cyclic or bicyclic group can be saturated or unsaturated. Exemplary structures include, but are not limited to, the following:

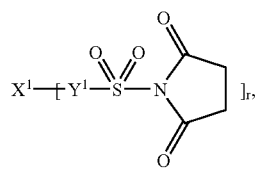

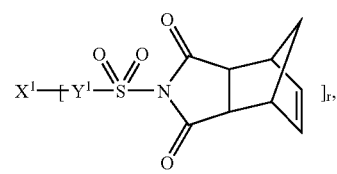

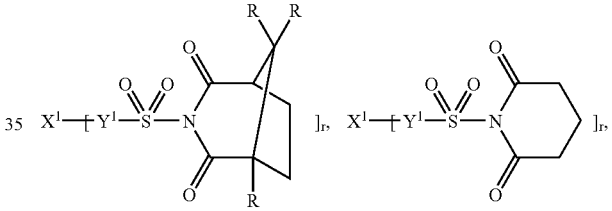

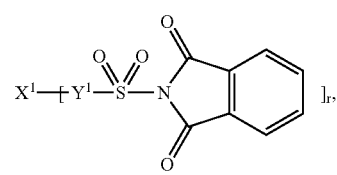

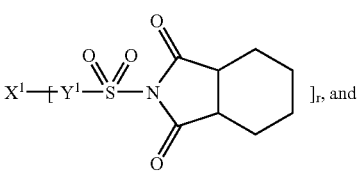

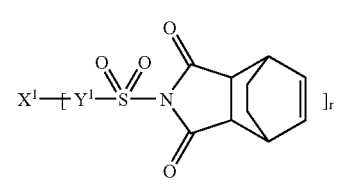

where R is an alkyl and the groups $X^1$, r, and $Y^1$ are the same as previously defined for Formula I. The compounds can be unsubstituted or substituted with a halo, alkyl, alkoxy, or combinations thereof.

In some examples, the compounds have the following structures:

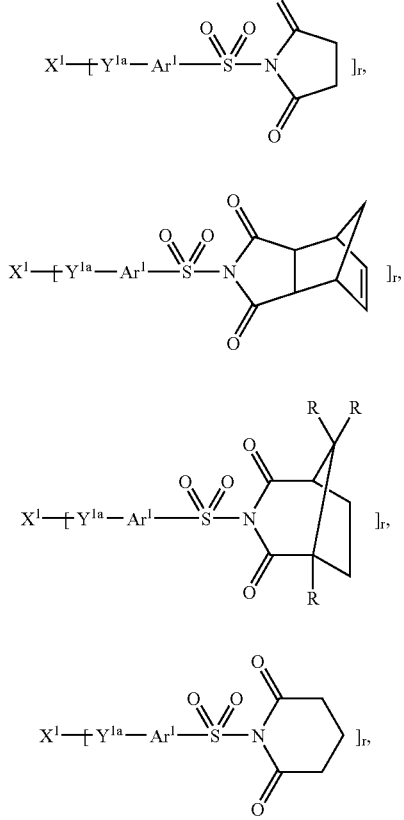

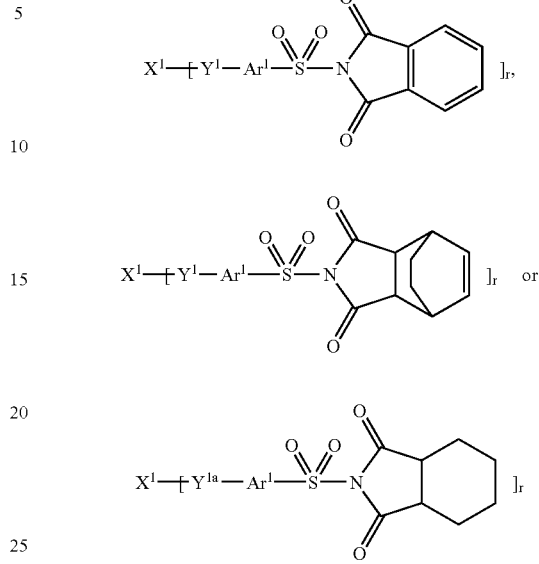

where R is an alkyl; $Ar^1$ is an arylene; and $Y^{1a}$ is selected from a single bond, alkylene, heteroalkylene, carbonyl, carbonyloxy, carbonylimino, oxy, thio, —$NR^d$— where $R^d$ is hydrogen or alkyl, or combinations thereof. The compounds can be unsubstituted or substituted with a halo, alkyl, alkoxy, or combinations thereof. In some examples, $Ar^1$ is phenylene.

Exemplary compounds according to formula I include, but are not limited to, the following:

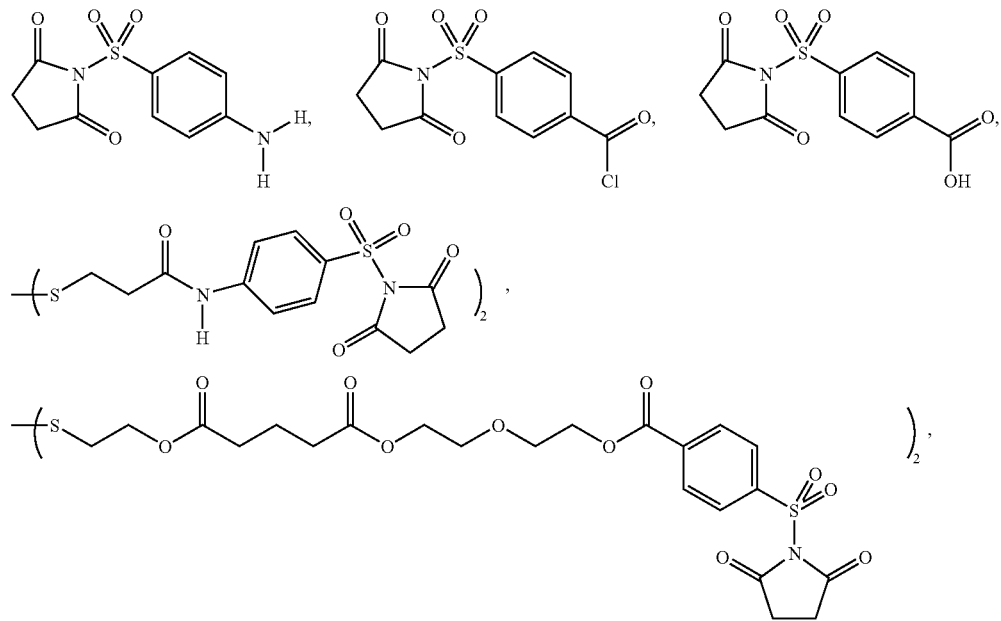

-continued
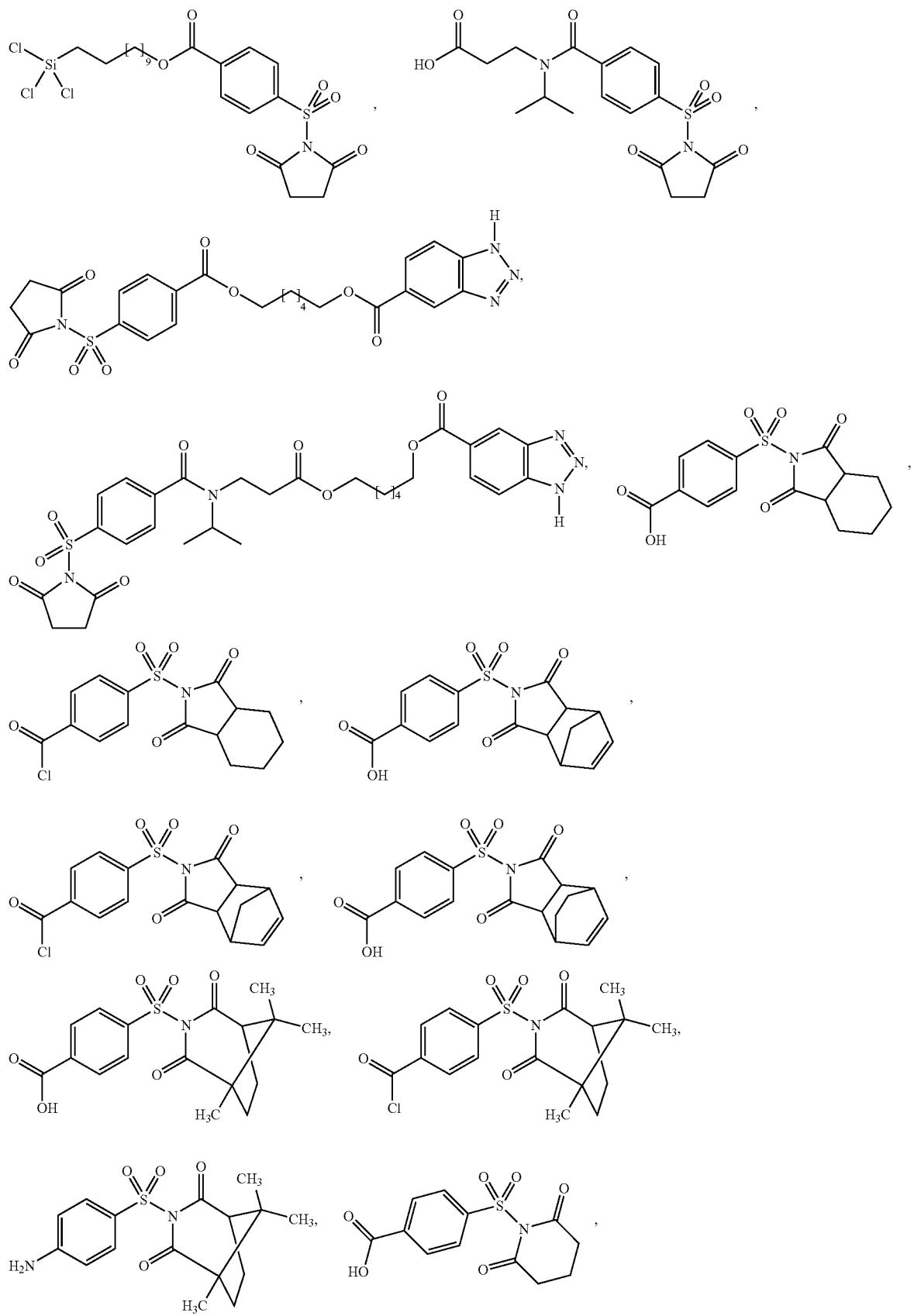

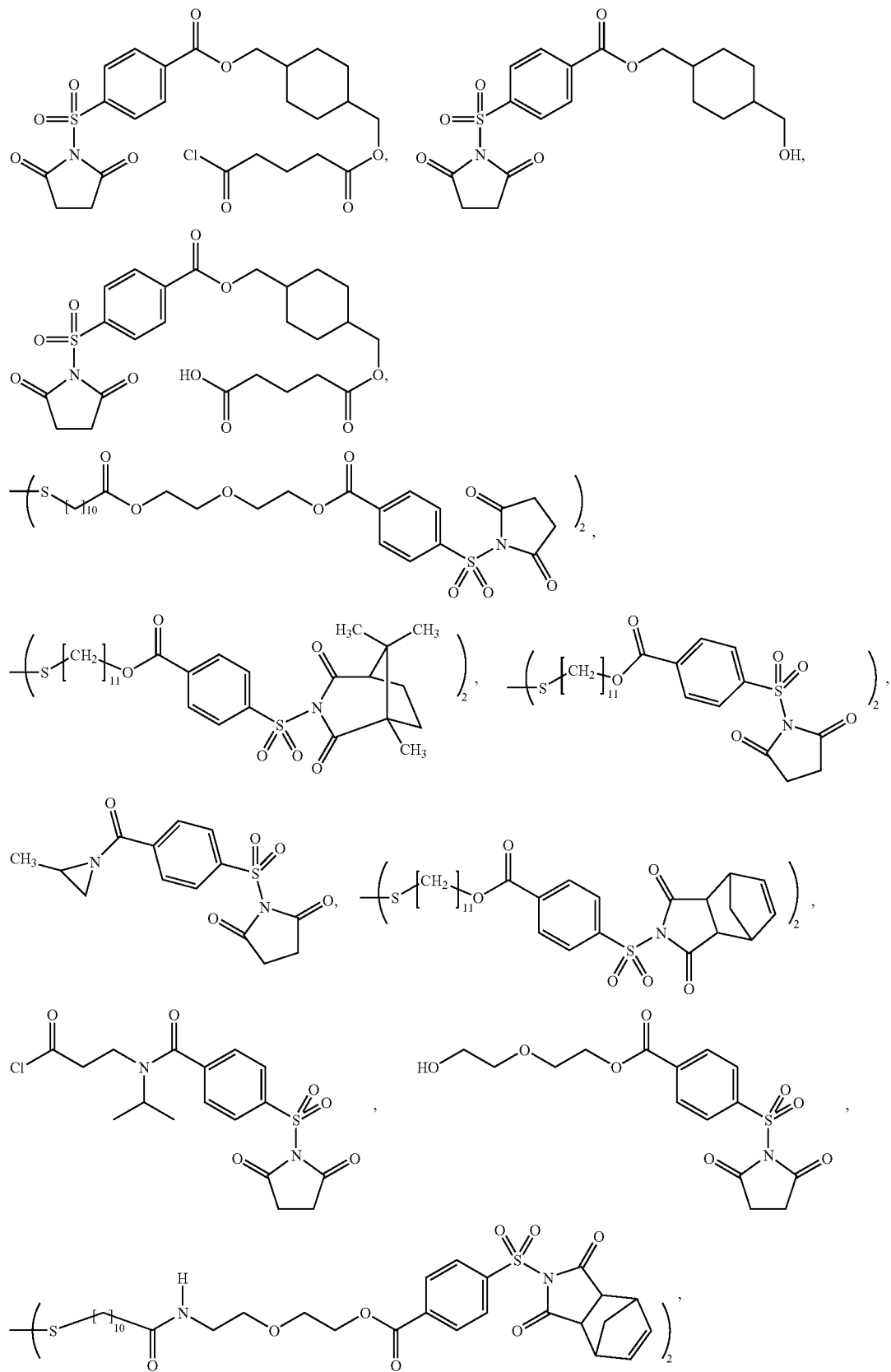

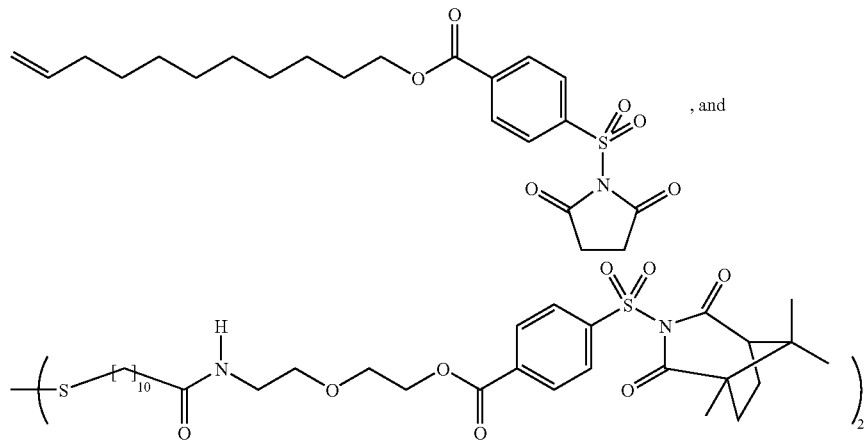

These compounds and any other compounds within the scope of Formula I can be unsubstituted or substituted with a halo, alkyl, alkoxy, or combinations thereof.

Another aspect of the invention provides compounds of Formula II:

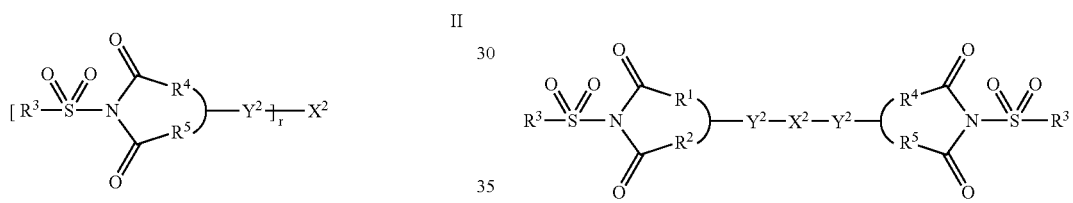

where
X² is a substrate-reactive functional group selected from a carboxy, halocarbonyl, halocarbonyloxy, cyano, hydroxy, mercapto, isocyanato, halosilyl, alkoxysilyl, acyloxysilyl, azido, aziridinyl, haloalkyl, tertiary amino, primary aromatic amino, secondary aromatic amino, disulfide, alkyl disulfide, benzotriazolyl, phosphono, phosphoroamido, phosphato, or ethylenically unsaturated group;
R⁴ and R⁵ together with a dicarboximide group to which they are attached form a four to eight membered heterocyclic or heterobicyclic group that can be fused to an optional aromatic group, optional saturated or unsaturated cyclic group, or optional saturated or unsaturated bicyclic group;
Y² is a single bond or a divalent group selected from an alkylene, heteroalkylene, arylene, carbonyl, carbonyloxy, carbonylimino, oxy, thio, —NR$^d$— where R$^d$ is hydrogen or alkyl, or combinations thereof;
R³ is an alkyl, aryl, aralkyl, or —NR$^b$R$^c$ wherein R$^b$ and R$^c$ are each an alkyl group or taken together with the nitrogen atom to which they are attached form a four to eight membered heterocyclic group; and
r is equal to 1 when X² is monovalent or equal to 2 when X² is a divalent group. The compounds according to Formula II can be unsubstituted or substituted with a halo, alkyl, alkoxy, or combinations thereof.

The functional group X² typically does not react the N-sulfonyldicarboximide group in Formula II and can be used, for example, to provide attachment to a substrate by reacting with a complementary functional group on a surface of a substrate. That is, X² can react with a complementary functional group to form a substrate-attached tethering group. X² can be monovalent or divalent. When X² is divalent, r in Formula II is equal to 2 and the compound has the following structure:

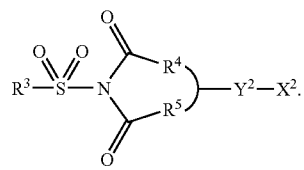

The compound can be symmetrical about X². A disulfide is an exemplary divalent X² group. When X² is monovalent, r in Formula II is equal to 1 and the compounds have the following structure:

Suitable X² groups include a carboxy, halocarbonyl, halocarbonyloxy, cyano, hydroxy, mercapto, isocyanato, halosilyl, alkoxysilyl, acyloxysilyl, azido, aziridinyl, haloalkyl, tertiary amino, primary aromatic amino, secondary aromatic amino, disulfide, alkyl disulfide, benzotriazolyl, phosphono, phosphoroamido, phosphato, and an ethylenically unsaturated group.

The X² groups typically can react with a complementary functional group on a surface of a substrate to form a stable ionic bond, covalent bond, or combination thereof. Suitable X² groups for attachment to the surface of a polymeric substrate include a carboxy, halocarbonyl, halocarbonyloxy, cyano, hydroxy, mercapto, isocyanato, halosilyl, alkoxysilyl, acyloxysilyl, azido, aziridinyl, haloalkyl, tertiary amino, primary aromatic amino, secondary aromatic amino, or ethylenically unsaturated group. Suitable $X^2$ groups for attachment to the surface of gold-containing substrates include mercapto, disulfide, or alkyl disulfide. Suitable $X^2$ groups for attachment to the surface of other metal-containing substrates include benzotriazolyl, phosphono, phosphoroamido, or phosphato groups. Suitable $X^2$ groups for attachment to glass or ceramic-containing substrates as well as to metal oxide-containing or hydrated metal oxide-containing substrates include halosilyl, alkoxysilyl, or acyloxysilyl groups.

The $Y^2$ group can include an alkylene, heteroalkylene, arylene, carbonyl, carbonylimino, carbonyloxy, oxy, thio, —$NR^d$— where $R^d$ is hydrogen or alkyl, or combinations thereof. In some examples, $Y^2$ can be an alkylene group. In other examples, a first alkylene group can be connected to a second alkylene group or to a first heteroalkylene group with a group selected from a carbonyl, carbonyloxy, carbonylimino, oxy, thio, or —$NR^d$— where $R^d$ is hydrogen or alkyl. Additional alkylene or heteroalkylene groups can be connected to the second alkylene group or the first heteroalkylene group with a group selected from a carbonyl, carbonyloxy, carbonylimino, oxy, thio, or —$NR^d$— where $R^d$ is hydrogen or alkyl. In yet other examples, $Y^2$ can be a heteroalkylene group or a first heteroalkylene group can be connected to another group. For example, a first heteroalkylene can be connected to a second heteroalkylene group or to a first alkylene group with a group selected from a carbonyl, carbonyloxy, carbonylimino, oxy, thio, or —$NR^d$— where $R^d$ is hydrogen or alkyl. Additional alkylene or heteroalkylene groups can be connected to the second heteroalkylene group or the first alkylene group with a group selected from a carbonyl, carbonyloxy, carbonylimino, oxy, thio, or —$NR^d$— where $R^d$ is hydrogen or alkyl.

In some examples, the $Y^2$ group can be a heteroalkylene group as in the following formula:

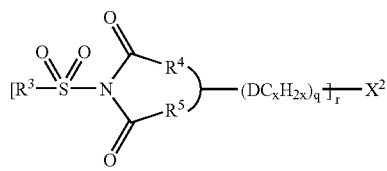

where q is an integer of 1 to 200; x is an integer of 1 to 4; and D is oxygen, sulfur, or NH. Exemplary compounds include those where q is an integer no greater than 150, no greater than 100, no greater than 80, no greater than 60, no greater than 40, no greater than 20, no greater than 10, no greater than 5, no greater than 4, no greater than 3, no greater than 2, or equal to 1; and x is no greater than 3, no greater than 2, or equal to 1. In some compounds, D is oxygen or sulfur; q is equal to 1 or 2; and x is equal to 1 or 2. The groups $X^2$, r, $R^3$, $R^4$, and $R^5$ are the same as previously defined for Formula II. The compounds can be unsubstituted or substituted with a halo, alkyl, alkoxy, or combinations thereof.

In some other examples, the group $Y^2$ can be a single bond with the $X^2$ group bonded directly to the ring structure formed with $R^4$ and $R^5$ together with a dicarboximide group to which they are attached as in the following structure:

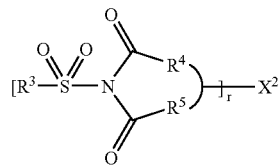

where the groups $X^2$, r, $R^3$, $R^4$, and $R^5$ are the same as previously defined for Formula II. The compounds can be unsubstituted or substituted with a halo, alkyl, alkoxy, or combinations thereof.

In Formula II, $R^4$ and $R^5$ together with a dicarboximide group to which they are attached form a four to eight membered heterocyclic or heterobicyclic group that can be fused to an optional aromatic group, optional saturated or unsaturated cyclic group, or optional saturated or unsaturated bicyclic group. Exemplary structures include, but are not limited to the following:

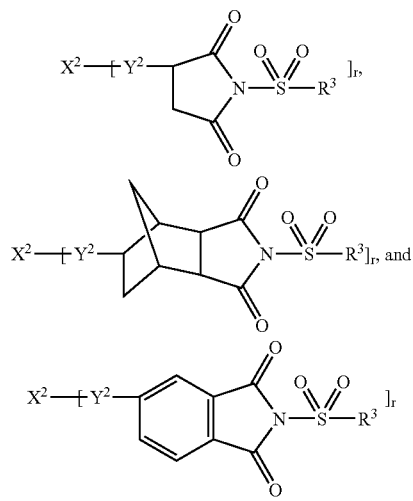

where $X^2$, $Y^2$, $R^3$, and r are as the same as previously defined for Formula II. The compounds can be unsubstituted or substituted with a halo, alkyl, alkoxy, or combinations thereof.

The $R^3$ group in Formula II can be an alkyl, aryl, or aralkyl. Suitable alkyl groups typically contain no greater than 30 carbon atoms, no greater than 20 carbon atoms, no greater than 10 carbon atoms, no greater than 6 carbon atoms, or no greater than 4 carbon atoms. In some compounds, the alkyl group is methyl, ethyl, or propyl. Suitable aryl groups typically contain 6 to 30 carbon atoms, 6 to 24 carbon atoms, 6 to 18 carbon atoms, 6 to 12 carbon atoms, or 6 carbon atoms. In some compounds, the aryl group is phenyl. Suitable aralkyl groups typically contain an aryl group having 6 to 30 carbon atoms and an alkyl group having no greater than 30 carbon atoms. An example of an aralkyl group is 4-methyl-phenyl.

In other embodiments of Formula II, $R^3$ is a group —$NR^bR^c$ where $R^b$ and $R^c$ are alkyl groups having no greater than 30 carbon atoms, no greater than 20 carbon atoms, no greater than 10 carbon atoms, no greater than 6 carbon atoms, or no greater than 4 carbon atoms. Alternatively, the $R^b$ and $R^c$ groups can combine together with the nitrogen atom to which they are attached to form a 4 to 8 membered ring structure. For example, $R^b$ and $R^c$ can combine to form a five or six membered heterocyclic group having a nitrogen heteroatom.

Exemplary compounds according to Formula II include, but are not limited to, the following:

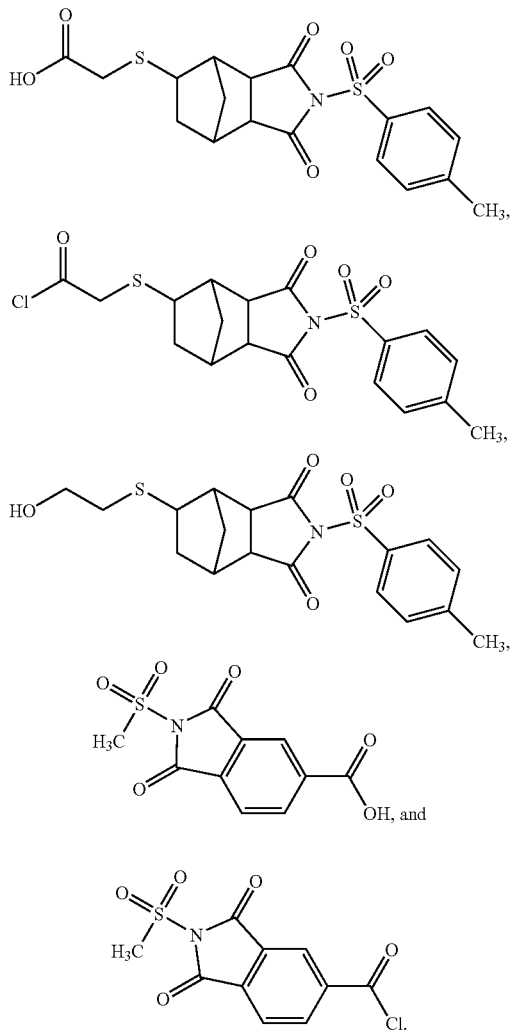

These compounds and any other compounds within the scope of Formula II can be unsubstituted or substituted with a halo, alkyl, alkoxy, or combinations thereof.

Method of Preparing Compounds

The compounds of Formula I may be prepared, for example, by reaction of a first compound having a nitrogen containing group with a second compound that includes a carboxylic acid anhydride. More specifically, the nitrogen containing group of the first compound includes a nitrogen atom directly bonded to a sulfonyl group and to two hydrogen atoms. The first compound may further include a substrate-reactive group $X^1$ or a group that can be converted to a substrate-reactive group $X^1$. The substrate-reactive group does not react, or reacts slowly, with the carboxylic acid anhydride of the second compound such that the nitrogen-containing group of the first compound reacts preferentially with the carboxylic acid anhydride. The reaction is shown in Reaction Scheme A.

Reaction Scheme A

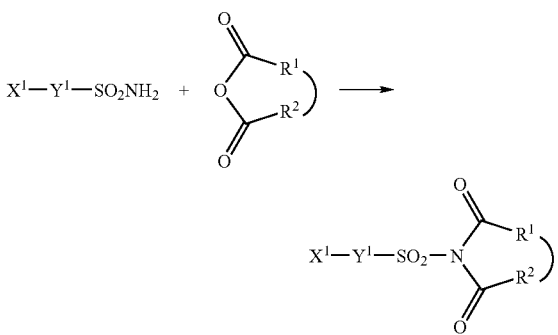

where $X^1$, $Y^1$, $R^1$, and $R^2$ are the same as previously defined for Formula I.

The compounds of Formula II may be prepared, for example, by reaction of a first compound having a nitrogen containing group with a second compound containing a carboxylic acid anhydride. More specifically, the nitrogen-containing group of the first compound includes a nitrogen atom directly bonded to a sulfonyl group and to two hydrogen atom. The second compound can also include a substrate-reactive group $X^2$ or a group that can be converted to a substrate-reactive group $X^2$. A typical synthesis approach is shown in Reaction Scheme B.

Reaction Scheme B

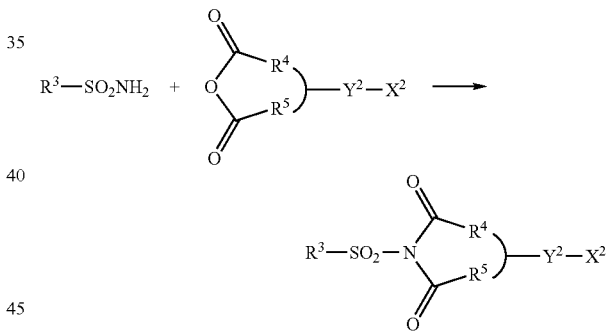

where $R^3$, $R^4$, $R^5$, $Y^2$, and $X^2$ are the same as previously defined for Formula II.

Articles

Another aspect of the invention provides articles that include a tethering group attached to a substrate (i.e., substrate-attached tethering group). The substrate-attached tethering group is the reaction product of the group $X^1$ in compounds of Formula I or the group $X^2$ in the compounds of Formula II with a complementary functional group G on a surface of a substrate. The substrate-attached tethering group has a N-sulfonyldicarboximide group that can react with an amine-containing material to form a connector group between the substrate and the amine-containing material. The formation of the connector group results in the immobilization of the amine-containing material to the substrate.

The substrate is a solid phase material to which the tethering groups can be attached. The substrate is not soluble in a solution used to react a compound of Formula I or II with a complementary functional group on the surface of the substrate (i.e., the substrate is not soluble in a solution used to prepare the substrate-attached tethering group). Typically, a tethering group is attached only to an outer portion of the substrate and a bulk portion of the substrate is not modified during the process of attaching the tethering group to the substrate. If the substrate has groups G distributed throughout the substrate, only those groups in the outer portion (e.g., on or near the surface) are usually capable of reacting with group $X^1$ in compounds of Formula I or with group $X^2$ in compounds of Formula II.

The substrates can have any useful form including, but not limited to, thin films, sheets, membranes, filters, nonwoven or woven fibers, hollow or solid beads, bottles, plates, tubes, rods, pipes, or wafers. The substrates can be porous or non-porous, rigid or flexible, transparent or opaque, clear or colored, and reflective or non-reflective. Suitable substrate materials include, for example, polymeric materials, glasses, silicons, ceramics, metals, metal oxides, hydrated metal oxides, or combinations thereof.

The substrates can have a single layer or multiple layers of material. For example, the substrate can have one or more second layers that provide support for a first layer that includes a complementary functional group capable of reacting with the $X^1$ group in compounds of Formula I or with the $X^2$ group in compounds of Formula II. In some embodiments, a surface of a second layer is chemically modified or coated with another material to provide a first layer that has a complementary functional group capable of reacting with the $X^1$ or the $X^2$ group. The first layer is the outer layer of the substrate.

Suitable polymeric substrate materials include, but are not limited to, polyolefins, polystyrenes, polyacrylates, polymethacrylates, polyacrylonitriles, poly(vinylacetates), polyvinyl alcohols, polyvinyl chlorides, polyoxymethylenes, polycarbonates, polyamides, polyimides, polyurethanes, phenolics, polyamines, amino-epoxy resins, polyesters, silicones, cellulose based polymers, polysaccharides, or combinations thereof. In some embodiments, the polymeric material is a copolymer prepared using a comonomer having a complementary functional group capable of reacting with a group $X^1$ in compounds according to Formula I or with a group $X^2$ in compound according to Formula II. For example, the comonomer can contain a carboxy, mercapto, hydroxy, amino, or alkoxysilyl group.

Suitable glass and ceramic substrate materials can include, for example, sodium, silicon, aluminum, lead, boron, phosphorous, zirconium, magnesium, calcium, arsenic, gallium, titanium, copper, or combinations thereof. Glasses typically include various types of silicate-containing materials. The substrate can be a silicon-based material such as a dielectric material or a material suitable for use in integrated circuits or other electronic devices.

In some embodiments, the substrate has a layer of diamond-like glass as disclosed in International Patent Application WO 01/66820 A1, the disclosure of which is incorporated herein by reference in its entirety. The diamond-like glass is an amorphous material that includes carbon, silicon, and one or more elements selected from hydrogen, oxygen, fluorine, sulfur, titanium, or copper. Some diamond-like glass materials are formed from a tetramethylsilane precursor using a plasma process. A hydrophobic material can be produced that is further treated in an oxygen plasma to control the silanol concentration on the surface.

Diamond-like glass can be in the form of a thin film or in the form of a coating on another layer or material in the substrate. In some applications, the diamond-like glass can be in the form of a thin film having at least 30 weight percent carbon, at least 25 weight percent silicon, and up to 45 weight percent oxygen. Such films can be flexible and transparent. In some embodiments, the diamond-like glass is the outer layer of a multilayer substrate. In a specific example, the second layer (e.g., support layer) of the substrate is a polymeric material and the first layer is a thin film of diamond-like glass. The tethering group is attached to the surface of the diamond-like glass.

In some multilayer substrates, the diamond like glass is deposited on a layer of diamond-like carbon. For example, the second layer (e.g., support layer) is a polymeric film having a layer of diamond-like carbon deposited on a surface. A layer of diamond-like glass is deposited over the diamond-like carbon layer. The diamond-like carbon can, in some embodiments, function as a tie layer or primer layer between a polymeric layer and a layer of diamond-like glass in a multilayer substrate. For example, the multilayer substrate can include a polyimide or polyester layer, a layer of diamond-like carbon deposited on the polyimide or polyester, and a layer of diamond-like glass deposited on the diamond-like carbon. In another example, the multilayer substrate includes a stack of the layers arranged in the following order: diamond-like glass, diamond-like carbon, polyimide or polyester, diamond-like carbon, and diamond-like glass.

Diamond-like carbon films can be prepared, for example, from acetylene in a plasma reactor. Other methods of preparing such films are described U.S. Pat. Nos. 5,888,594 and 5,948,166 as well as in the article M. David et al., *AIChE Journal*, 37 (3), 367–376 (March 1991), the disclosures of which are incorporated herein by reference.

Suitable metals, metal oxides, or hydrated metal oxides for substrates can include, for example, gold, silver, platinum, palladium, aluminum, copper, chromium, iron, cobalt, nickel, zinc, and the like. The metal-containing material can include alloys such as stainless steel, indium tin oxide, and the like. In some embodiments, a metal-containing material is the outer layer of a multilayer substrate. For example, the substrate can have a polymeric second layer and a metal containing first layer. In one more specific example, the second layer is a polymeric film and the first layer is a thin film of gold. In other examples, a multilayer substrate includes a polymeric film coated with a titanium-containing layer and then with a gold-containing layer. That is, the titanium layer can function as a tie layer or a primer layer for adhering the layer of gold to the polymeric film. The polymeric film is some examples can be a polyester or polyimide film.

In still other examples of a multilayer substrate that includes a metal-containing material, a silicon support layer can be covered with one or more metal-containing material. In a specific example, a silicon support layer can be covered with a layer of chromium and then with a layer of gold. The chromium layer can improve the adhesion of the gold layer to the silicon layer.

The surface of the substrate typically includes a group capable of reacting with a carboxy, halocarbonyl, halocarbonyloxy, cyano, hydroxy, mercapto, isocyanato, halosilyl, alkoxysilyl, acyloxysilyl, azido, aziridinyl, haloalkyl, tertiary amino, primary aromatic amino, secondary aromatic amino, disulfide, alkyl disulfide, benzotriazolyl, phosphono, phosphoroamido, phosphato, or ethylenically unsaturated group. That is, the substrate includes a group capable of reacting with the group $X^1$ in compounds Formula I or with the group $X^2$ in compounds of Formula II (i.e., the substrate includes a complementary functional group to the group $X^1$ or $X^2$). Substrates can include a support material treated to form an outer layer that includes a complementary functional group. The substrate can be prepared from any solid phase material known to have groups capable of reacting with $X^1$ or with $X^2$ and is not limited to the following examples of suitable materials.

A carboxy group or a halocarbonyl group can react with a substrate having a hydroxy group to form a carbonyloxy-containing attachment group. Examples of substrate materials having hydroxy groups include, but are not limited to, polyvinyl alcohol, hydroxy substituted esters of polymethacrylates, hydroxy substituted esters of polyacrylates, corona-treated polyethylene, and a polyvinyl alcohol coating on a support material such as glass or polymeric film.

A carboxy group or a halocarbonyl group can also react with a substrate having a mercapto group to form a carbonylthio-containing attachment group. Examples of substrate materials having a mercapto group include, but are not limited to, mercapto substituted esters of polyacrylates, mercapto substituted esters of polymethacrylates, and glass treated with a mercaptoalkylsilane.

Additionally, a carboxy group or a halocarbonyl group can react with a primary aromatic amino group, a secondary aromatic amino group, or a secondary aliphatic amino group to form a carbonylimino-containing attachment group. Examples of substrate materials having aromatic primary or secondary amino group include, but are not limited to, polyamines, amine substituted esters of polymethacrylate, amine substituted esters of polyacrylate, polyethylenimines, and glass treated with an aminoalkylsilane.

A halocarbonyloxy group can react with a substrate having a hydroxy group to form an oxycarbonyloxy-containing attachment group. Examples of substrate materials having hydroxy groups include, but are not limited to, polyvinyl alcohol, corona-treated polyethylene, hydroxy substituted esters of polymethacrylates, hydroxy substituted esters of polyacrylates, and a polyvinyl alcohol coating on a support material such as glass or a polymeric film.

A halocarbonyloxy group can also react with a substrate having a mercapto group to form an oxycarbonylthio-containing attachment group. Examples of substrate materials having a mercapto group include, but are not limited to, mercapto substituted esters of polymethacrylates, mercapto substituted esters of polyacrylates, and glass treated with a mercaptoalkylsilane.

Additionally, a halocarbonyloxy group can react with a substrate having a primary aromatic amino group, a secondary aromatic amino group, or a secondary aliphatic amino group to form an oxycarbonylimino-containing attachment group. Examples of substrate materials having aromatic primary or secondary amino groups include, but are not limited to, polyamines, amine substituted esters of polymethacrylate, amine substituted esters of polyacrylate, polyethylenimines, and glass treated with an aminoalkylsilane.

A cyano group can react with a substrate having an azido group to form a tetrazinediyl-containing attachment group. Examples of substrates having azido groups include, but are not limited to, a coating of poly(4-azidomethylstyrene) on a glass or polymeric support. Suitable polymeric support materials include polyesters, polyimides, and the like.

A hydroxy group can react with a substrate having isocyanate group to form an oxycarbonylimino-containing attachment group. Suitable substrates having isocyanate groups include, but are not limited to, a coating of 2-isocyanatoethylmethacrylate polymer on a support material. Suitable support materials include glass and polymeric materials such as polyesters, polyimides, and the like.

A hydroxy group can react with a substrate having a carboxy, carbonyloxycarbonyl, or halocarbonyl to form a carbonyloxy-containing attachment group. Suitable substrates include, but are not limited to, a coating of acrylic acid polymer or copolymer on a support material or a coating of a methacrylic acid polymer or copolymer on a support material. Suitable support materials include glass and polymeric materials such as polyesters, polyimides, and the like. Other suitable substrates include copolymers of polyethylene with polyacrylic acid, polymethacrylic acid, or combinations thereof.

A mercapto group can react with a substrate having isocyanate groups. The reaction between a mercapto group and an isocyanate group forms a thiocarbonylimino-containing attachment group. Suitable substrates having isocyanate groups include, but are not limited to, a coating of 2-isocyanatoethylmethacrylate polymer on a support material. Suitable support materials include glass and polymeric materials such as polyesters, polyimides, and the like.

A mercapto group can also react with a substrate having a halocarbonyl group to form a carbonylthio-containing attachment group. Substrates having halocarbonyl groups include, for example, chlorocarbonyl substituted polyethylene.

A mercapto group can also react with a substrate having a halocarbonyloxy group to form an oxycarbonlythio-containing attachment group. Substrates having halocarbonyl groups include chloroformyl esters of polyvinyl alcohol.

Additionally, a mercapto group can react with a substrate having an ethylenically unsaturated group to form a thioether-containing attachment group. Suitable substrates having an ethylenically unsaturated group include, but are not limited to, polymers and copolymers derived from butadiene.

An isocyanato group can react with a substrate having a hydroxy group to form a oxycarbonylimino-containing attachment group. Examples of substrate materials having hydroxy groups include, but are not limited to, polyvinyl alcohol, corona-treated polyethylene, hydroxy substituted esters of polymethacrylates or polyacrylates, and a polyvinyl alcohol coating on glass or polymeric film.

An isocyanate group can also react with a mercapto group to form a thiocarbonylimino-containing attachment group. Examples of substrate materials having a mercapto group include, but are not limited to, mercapto substituted esters of polymethacrylates or polyacrylates and glass treated with a mercaptoalkylsilane.

Additionally, an isocyanate group can react with a primary aromatic amino group, a secondary aromatic amino group, or a secondary aliphatic amino group to form an iminocarbonylimino-containing attachment group. Suitable substrates having a primary or secondary amino groups include, but are not limited to, polyamines, polyethylenimines, and coatings of an aminoalkylsilane on a support material such as glass or on a polymeric material such as a polyester or polyimide.

An isocyanate group can also react with a carboxy to form an O-acyl carbamoyl-containing attachment group. Suitable substrates having a carboxylic acid group include, but are not limited to, a coating of an acrylic acid polymer or copolymer or a coating of a methacrylic acid polymer or copolymer on a glass or polymeric support. Copolymers include, but are not limited to, copolymers that contain polyethylene and polyacrylic acid or polymethacrylic acid. Suitable polymeric support materials include polyesters, polyimides, and the like.

A halosilyl group, an alkoxysilyl group, or an acyloxysilyl group can react with a substrate having a silanol group to form a disiloxane-containing attachment group. Suitable substrates include those prepared from various glasses, ceramic materials, or polymeric material. These groups can also react with various materials having metal hydroxide groups on the surface to form a siloxane-containing attachment group. Suitable metals include, but are not limited to, silver, aluminum, copper, chromium, iron, cobalt, nickel, zinc, and the like. In some embodiments, the metal is stainless steel or another alloy. Polymeric material can be prepared to have silanol groups. For example, commercially available monomers with silanol groups include 3-(trimethoxysilyl) propylmethacrylate and 3-aminopropyltrimethoxy silane from Aldrich Chemical Co., Milwaukee, Wis.

An azido group can react, for example, with a substrate having a carbon-carbon triple bond to form a triazolediyl-containing attachment group. An azido group can also react with a substrate having nitrile groups to form a tetrazinediyl-containing attachment group. Substrates having nitrile groups include, but are not limited to, coatings of polyacrylonitrile on a support material such as glass or a polymeric material. Suitable polymeric support material includes polyesters and polyimides, for example. Other suitable substrates having nitrile groups include acrylonitrile polymers or copolymers and 2-cyanoacrylate polymers or copolymers.

An azido group can also react with a strained olefinic group to form a triazolediyl-containing attachment group. Suitable substrates having a strained olefinic group include coatings of materials having pendant norbornenyl functional groups. Suitable support materials include, but are not limited to, glass and polymeric materials such as polyesters and polyimides.

An aziridinyl group can react with a mercapto group to form a β-aminoalkylthioether attachment group. Examples of substrate materials having a mercapto group include, but are not limited to, mercapto substituted esters of polymethacrylates or polyacrylates and glass treated with a mercaptoalkylsilane.

Additionally, an aziridinyl group can react with a carboxy group to form a β-aminoalkyloxycarbonyl-containing attachment group. Suitable substrates having a carboxy include, but are not limited to, a coating of a acrylic acid polymer or copolymer or a coating of a methacrylic acid polymer or copolymer on a glass or polymeric support. Copolymers include, but are not limited to, copolymers that contain polyethylene and polyacrylic acid or polymethacrylic acid. Suitable polymeric support materials include polyesters, polyimides, and the like.

A haloalkyl group can react, for example, with a substrate having a tertiary amino group to form a quaternary ammonium-containing attachment group. Suitable substrates having a tertiary amino group include, but are not limited to, polydimethylaminostyrene or polydimethylaminoethylmethacrylate.

Likewise, a tertiary amino group can react, for example, with a substrate having a haloalkyl group to form a quaternary ammonium-containing attachment group. Suitable substrates having a haloalkyl group include, for example, coatings of a haloalkylsilane on a support material. Support materials can include, but are not limited to, glass and polymeric materials such as polyesters and polyimides.

A primary aromatic amino or a secondary aromatic amino group can react, for example, with a substrate having an isocyanate group to form an oxycarbonylimino-containing attachment group. Suitable substrates having isocyanate groups include, but are not limited to, a coating of a 2-isocyanatoethylmethacrylate polymer or copolymer on a glass or polymeric support. Suitable polymeric supports include polyesters, polyimides, and the like.

A primary aromatic amino or a secondary aromatic amino group can also react with a substrate containing a carboxy or halocarbonyl group to form a carbonylimino-containing attachment group. Suitable substrates include, but are not limited to, acrylic or methacrylic acid polymeric coatings on a support material. The support material can be, for example, glass or a polymeric material such as polyesters or polyimides. Other suitable substrates include copolymers of polyethylene and polymethacrylic acid or polyacrylic acid.

A disulfide or an alkyl disulfide group can react, for example, with a metal surface to form a metal sulfide-containing attachment group. Suitable metals include, but are not limited to gold, platinum, palladium, nickel, copper, and chromium. The substrate can also be an alloy such an indium tin oxide or a dielectric material.

A benzotriazolyl can react, for example, with a substrate having a metal or metal oxide surface. Suitable metals or metal oxides include, for example, silver, aluminum, copper, chromium, iron, cobalt, nickel, zinc, and the like. The metals or metal oxides can include alloys such as stainless steel, indium tin oxide, and the like.

A phosphono, phosphoroamido, or phosphato can react, for example, with a substrate having a metal or metal oxide surface. Suitable metals or metal oxides include, for example, silver, aluminum, copper, chromium, iron, cobalt, nickel, zinc, and the like. The metals or metal oxides can include alloys such as stainless steel, indium tin oxide, and the like.

An ethylenically unsaturated group can react, for example, with a substrate having a mercapto group. The reaction forms a heteroalkylene-containing attachment group. Suitable substrates include, for example, mercapto-substituted alkyl esters of polyacrylates or polymethacrylates.

An ethylenically unsaturated group can also react with a substrate having a silicon surface, such as a silicon substrate formed using a chemical vapor deposition process. Such silicon surfaces can contain —SiH groups that can react with the ethylenically unsaturated group in the presence of a platinum catalyst to form an attachment group with Si bonded to an alkylene group.

Additionally, an ethylenically unsaturated group can react with a substrate having a carbon-carbon double bond to form an alkylene-containing attachment group. Such substrates include, for example, polymers or copolymers derived from butadiene.

The compounds of Formula I and II can undergo self-assembly when contacted with a substrate. As used herein, the term "self-assembly" refers to a process in which materials can spontaneously form a monolayer of substrate-attached tethering groups when contacted with a substrate. For example, compounds having a disulfide or alkyl disulfide group for $X^1$ or $X^2$ can undergo a self-assembly process when exposed to a gold substrate. As another example, compounds having a halosilyl group for $X^1$ or $X^2$ can undergo a self-assembly process when exposed to a diamond-like glass or glass substrate.

In one embodiment, Formula III can represent the articles of the invention:

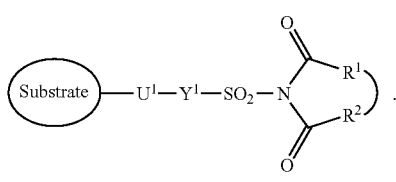

III

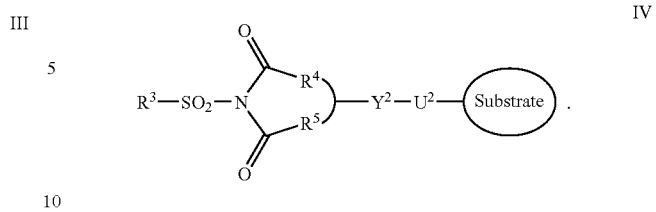

IV

Formula III represents a tethering group attached to a substrate. The tethering group is derived from a compound according to Formula I. The group $U^1$ is the attachment group formed by reaction of $X^1$ in a compound of Formula I with a complementary functional group on a surface of the substrate. The groups $Y^1$, $R^1$, and $R^2$ are the same as previously defined for Formula I. That is, the article includes:

a substrate; and a substrate-attached tethering group that includes a reaction product of a complementary functional group G on a surface of the substrate with a compound of Formula I

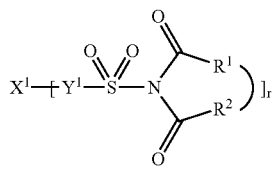

I where $X^1$ is a substrate-reactive functional group selected from a carboxy, halocarbonyl, halocarbonyloxy, cyano, hydroxy, mercapto, isocyanato, halosilyl, alkoxysilyl, acyloxysilyl, azido, aziridinyl, haloalkyl, tertiary amino, primary aromatic amino, secondary aromatic amino, disulfide, alkyldisulfide, benzotriazolyl, phosphono, phosphoroamido, phosphato, or ethylenically unsaturated group;

$Y^1$ is a single bond or a divalent group selected from an alkylene, heteroalkylene, arylene, carbonyl, carbonyloxy, carbonylimino, oxy, thio, or —$NR^d$— where $R^d$ is hydrogen or alkyl, or combinations thereof;

$R^1$ and $R^2$ together with a dicarboximide group to which they are attached form a four to eight membered heterocyclic or heterobicyclic group that can be fused to an optional aromatic group, optional saturated or unsaturated cyclic group, or optional saturated or unsaturated bicyclic group;

r is 1 when $X^2$ is a monovalent group or equal to 2 when $X^2$ is a divalent group; and G is the comoplementary functional group capable of reacting with $X^1$. The tethering group can be unsubstituted or substituted with a halo, alkyl, alkoxy, or combinations thereof.

In another embodiment, Formula IV can represent the articles of the invention:

Formula IV represents a tethering group attached to a substrate. The tethering group is derived from a compound of Formula II. The group $U^2$ is the attachment group formed by reaction of $X^2$ of a compound of Formula II with a complementary functional group on a surface of the substrate. The groups $R^3$, $R^4$, $R^5$, and $Y^2$ are the same as previously defined for Formula II. That is, the article includes:

a substrate;

a substrate-attached tethering group that includes a reaction product of a complementary functional group G on a surface of the substrate with a compound of Formula II

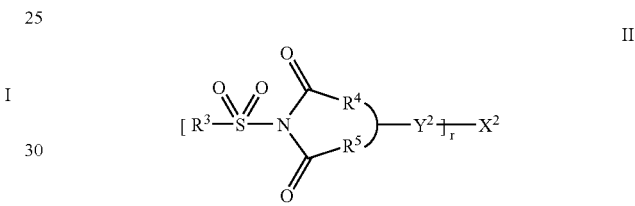

II where $X^2$ is a substrate-reactive functional group selected from a carboxy, halocarbonyl, halocarbonyloxy, cyano, hydroxy, mercapto, isocyanato, halosilyl, alkoxysilyl, acyloxysilyl, azido, aziridinyl, haloalkyl, tertiary amino, primary aromatic amino, secondary aromatic amino, disulfide, alkyl disulfide, benzotriazolyl, phosphono, phosphoroamido, phosphato, or ethylenically unsaturated group;

$R^4$ and $R^5$ together with a dicarboximide group to which they are attached form a four to eight heterocyclic or heterobicyclic group that can be fused to an optional aromatic group, optional saturated or unsaturated cyclic group, or optional saturated or unsaturated bicyclic group;

$Y^2$ is a single bond or a divalent group selected from alkylene, heteroalkylene, arylene, carbonyl, carbonyloxy, carbonylimino, oxy, is hydrogen or alkyl, or combinations thereof;

$R^3$ is an alkyl, aryl, aralkyl, or —$NR^bR^c$ wherein $R^b$ and $R^c$ are each an alkyl group or taken together with the nitrogen atom to which they are attached form a four to eight membered heterocyclic group;

r is equal to 1 when $X^2$ is monovalent or equal to 2 when $X^2$ is a divalent group: and G is the complementary functional group capable of reacting with $X^2$. The tethering group can be unsubstituted or substituted with a halo, alkyl, alkoxy, or combinations thereof.

Formulas III and IV shows only one tethering group attached to the substrate; however, more than one tethering group can be attached to the substrate if there are more than one complementary functional group G on the substrate.

Further, the substrate can have excess G groups on the surface of the substrate that have not reacted with a tethering compound.

Groups on a substrate (i.e., groups G) capable of reacting with $X^1$ groups in compounds according to Formula I or with the $X^2$ groups in compounds according to Formula II include, but are not limited to, hydroxy, mercapto, primary aromatic amino group, secondary aromatic amino group, secondary aliphatic amino group, azido, carboxy, carbonyloxycarbonyl, isocyanate, halocarbonyl, halocarbonyloxy, silanol, and nitrile.

The attachment of tethering groups to the surface of the substrate (i.e., formation of the substrate-attached tethering groups of Formulas III or IV) can be detected using techniques such as, for example, contact angle measurements of a liquid on the substrate before and after attachment of a tethering group derived from Formula I or Formula II (e.g., the contact angle can change upon attachment of a tethering group to the surface of a substrate), ellipsometry (e.g., the thickness of the attached layer can be measured), time-of-flight mass spectroscopy (e.g., the surface concentration can change upon attachment of a tethering group to a substrate), and Fourier Transform Infrared Spectroscopy (e.g., the reflectance and absorbance can change upon attachment of a tethering group to a substrate).

In other embodiments of articles of the invention, the N-sulfonyldicarboximide group in the tethering group has reacted with an amine-containing material to form a connector group resulting in the immobilization of an amine-containing material to the substrate. The amine-containing material can react with a N-sulfonyldicarboximide group of the substrate-attached tethering group of Formula III or Formula IV. The reaction typically opens the ring structure containing the dicarboximide group. In some embodiments, the amine-containing materials are biomolecules such as, for example, an amino acid, peptide, DNA, RNA, protein, enzyme, organelle, immunoglobin, or a fragment thereof. In other embodiments, the amine-containing material is a non-biological amine such as an amine-containing analyte.

The amine-containing material ($H_2N$-T) can react with the substrate-attached tethering groups of Formula III by a ring opening reaction to produce a substrate immobilized amine-containing material of Formula V:

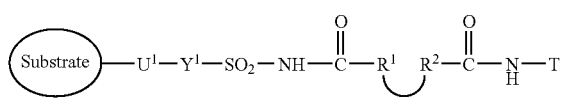

V where $U^1$ is the attachment group formed by reacting $X^1$ with a complementary functional group on the surface of the substrate; T is the remainder of the amine-containing material; and $Y^1$, $R^1$, and $R^2$ are the same as previously defined for Formulas I and III. $H_2N$-T is any suitable amine-containing material.

The amine-containing material ($H_2N$-T) can react with the substrate-attached tethering groups of Formula IV by a ring opening reaction to produce a substrate immobilized amine-containing material of Formula VI:

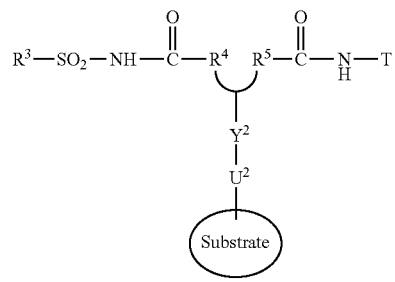

VI where $U^2$ is the attachment group formed by reacting $X^2$ with a complementary functional group on the surface of the substrate; T is the remainder of the amine-containing material; and $Y^2$, $R^3$, $R^3$, and $R^4$ are the same as previously defined for Formulas II and IV. $H_2N$-T is any suitable amine-containing material.

The presence of the immobilized amine can be determined, for example, using mass spectroscopy, contact angle measurement, infrared spectroscopy, and ellipsometry. Additionally, various immunoassays and optical microscopic techniques can be used if the amine-containing material is a biologically active material.

Other materials can be bound to the amine-containing compounds. For example, a complementary RNA or DNA fragment can hybridize with an immobilized RNA or DNA fragment. In another example, an antigen can bind to an immobilized antibody or an antibody can bind to an immobilized antigen. In a more specific example, bacteria can bind to an immobilized immunoglobulin. In an even more specific example, *Staphylococcus aureus* can bind to the immobilized IgG (i.e., Immunoglobulin G).

Method of Immobilizing Amine-Containing Material to a Substrate

Another aspect of the invention provides methods for immobilizing an amine-containing material to a substrate. The method involves preparing a substrate-attached tethering group by reacting a complementary functional group on a surface of the substrate with the substrate-reactive group $X^1$ in compounds of Formula I or $X^2$ in compounds of Formula II with; and reacting a N-sulfonyldicarboximide group of the substrate-attached tethering group with an amine-containing material to form a carbonylimino-containing connector group between the substrate and the immobilized amine-containing material.

In one embodiment, the method of immobilizing an amine-containing material to a substrate is shown in Reaction Scheme C for a monovalent $X^1$.

Reaction Scheme C

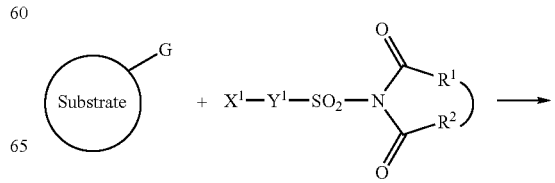

-continued

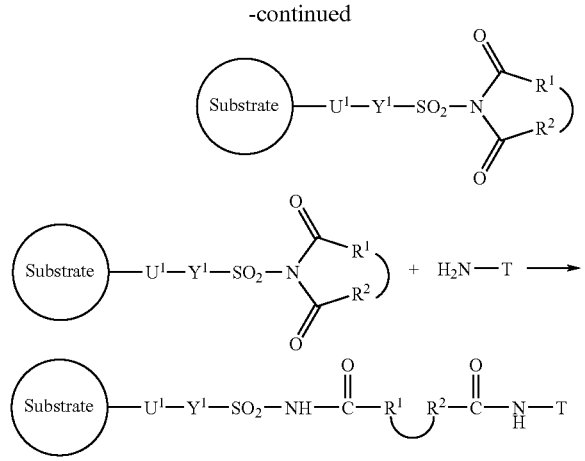

where $U^1$ is the attachment group formed by reacting $X^1$ with a group G on the surface of the substrate; T is the remainder of the amine-containing material (i.e., the group T represents all of the amine-containing material exclusive of the amine group); and $Y^1$, $R^1$, and $R^2$ are the same as previously defined for Formula I.

The method involves:

selecting a compound of Formula I

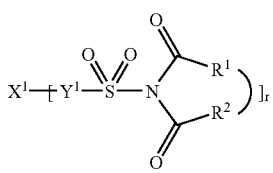

I where $X^1$ is a substrate-reactive functional group selected from a carboxy, halocarbonyl, halocarbonyloxy, cyano, hydroxy, mercapto, isocyanato, halosilyl, alkoxysilyl, acyloxysilyl, azido, aziridinyl, haloalkyl, tertiary amino, primary aromatic amino, secondary aromatic amino, disulfide, alkyldisulfide, benzotriazolyl, phosphono, phosphoroamido, phosphato, and ethylenically unsaturated group;

$Y^1$ is a single bond or a divalent group selected from an alkylene, heteroalkylene, arylene, carbonyl, carbonyloxy, carbonylimino, oxy, thio, $—NR^d—$ where $R^d$ is hydrogen or alkyl, or combinations thereof;

$R^1$ and $R^2$ together with a dicarboximide group to which they are attached form a four to eight membered heterocyclic or heterobicyclic group that can be fused to an optional aromatic group, optional saturated or unsaturated cyclic group, or optional saturated or unsaturated bicyclic group;

r is 1 when $X^1$ is a monovalent group or equal to 2 when $X^1$ is a divalent group; and said compound of Formula I is unsubstituted or substituted with a halo, alkyl, alkoxy, or combinations thereof;

providing a substrate having a complementary functional group capable of reacting with $X^1$;

preparing a substrate-attached tethering group by reacting $X^1$ with the complementary functional group on the substrate resulting in an ionic bond, covalent bond, or combinations thereof; and reacting a N-sulfonyldicarboximide group of the substrate-attached tethering group with an amine-containing material to form a connector group between the substrate and the amine-containing material. The connector group is the divalent group between the substrate and the group T in Formula V. The attachment group is part of the connector group.

In another embodiment, the method of attaching an amine-containing material to a substrate is shown in Reaction Schemes D for a monovalent $X^2$.

Reaction Scheme D

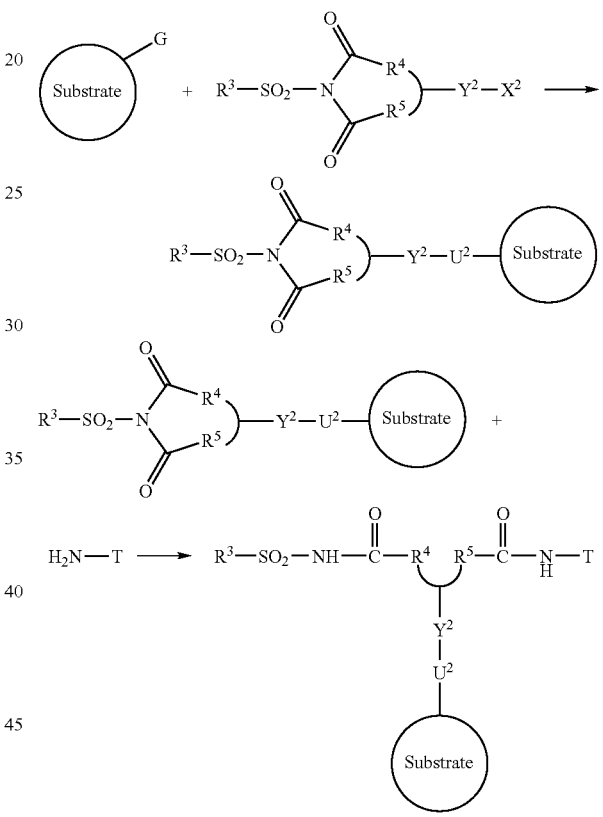

where $U^2$ is the attachment group formed by reacting $X^2$ with a group G on the surface of the substrate; T is the remainder of the amine-containing material; and $Y^2$, $R^3$, $R^4$, and $R^5$ are the same as previously defined for Formula II.

The method involves:

selecting a compound of Formula II

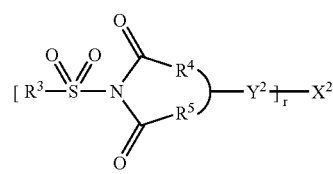

II where
- $X^2$ is a substrate-reactive functional group selected from a carboxy, halocarbonyl, halocarbonyloxy, cyano, hydroxy, mercapto, isocyanato, halosilyl, alkoxysilyl, acyloxysilyl, azido, aziridinyl, haloalkyl, tertiary amino, primary aromatic amino, secondary aromatic amino, disulfide, alkyl disulfide, benzotriazolyl, phosphono, phosphoroamido, phosphate, and ethylenically unsaturated group;
- $R^4$ and $R^5$ together with a dicarboximide group to which they are attached form a four to eight membered heterocyclic or heterobicyclic group that can be fused to an optional aromatic group, optional saturated or unsaturated cyclic group, or optional saturated or unsaturated bicyclic group;
- $Y^2$ is a single bond or a divalent group selected from alkylene, heteroalkylene, arylene, carbonyl, carbonyloxy, carbonylimino, oxy, thio, —$NR^d$— where $R^d$ is hydrogen or alkyl, or combinations thereof;
- $R^3$ is an alkyl, aryl, aralkyl, or —$NR^bR^c$ wherein $R^b$ and $R^c$ are each an alkyl group or taken together with the nitrogen atom to which they are attached form a four to eight membered heterocyclic group;
- r is equal to 1 when $X^3$ is monovalent or equal to 2 when $X^3$ is a divalent group; and
- said compound of Formula II is unsubstituted or substituted with a halo, alkyl, alkoxy, or combination thereof;

providing a substrate having a complementary functional group capable of reacting with $X^2$;

preparing a substrate-attached tethering group by reacting $X^2$ with the complementary functional group on the substrate resulting in an ionic, covalent bond, or combinations thereof; and reacting a N-sulfonyldicarboximide group of the substrate-attached tethering group with an amine-containing material to form a connector group between the substrate and the amine-containing material. The connector group is the divalent group between the substrate and the group T in Formula VI. The attachment group is part of the connector group.

Uses

The compounds of the invention can be used, for example, for immobilizing amine-containing material. In some embodiments, the amine-containing material is an amine analyte. In other embodiments, the amine-containing material is a biomolecules such as, for example, an amino acid, peptide, DNA, RNA, protein, enzyme, organelle, immunoglobin, or fragments thereof. Immobilized biological amine-containing materials can be useful in the medical diagnosis of a disease or of a genetic defect. The immobilized amine-containing materials can also be used for biological separations or for detection of the presence of various biomolecules. Additionally, the immobilized amine-containing materials can be used in bioreactors or as biocatalysts to prepare other materials. The substrate-attached tethering groups can be used to detect amine-containing analytes.

Biological amine-containing materials often can remain active after attachment to the substrate (i.e., the articles according to Formula V or VI can include biologically active amine-containing materials immobilized to the substrate). For example, an immobilized antibody can bind with an antigen or an immobilized antigen can bind with an antibody. An amine-containing material can bind to a bacterium. In a more specific example, the immobilized amine-containing material can bind to a Staphylococcus aureus bacterium (e.g., the immobilized amine-containing material can be a biomolecule that has a portion that can specifically bind to the bacterium).

The articles prepared by attaching the compounds of the invention to a substrate typically have improved hydrolytic stability compared to previously known articles prepared using a tethering compound that is a derivative of N-hydroxysuccinimide. Because of the hydrolytic stability, the compounds and the substrate-attached tethering groups of the invention can typically be used in aqueous systems.

When an amine-containing material reacts with a N-sulfonyldicarboximide group, a connector group is formed that results in the immobilization of the amine-containing material to the substrate (i.e., substrate immobilized amine-containing materials according to Formulas V or VI). The rate of reaction of amine-containing materials with the N-sulfonyldicarboximide groups of the substrate-attached tethering groups is typically faster than the rate of hydrolysis of the N-sulfonyldicarboximide group. That is, immobilization of amine-containing materials occurs at a faster rate than the hydrolysis reactions. The amine-containing materials are not easily displaced once immobilization to a substrate has occurred due to the formation of a covalent carbonylimino bond.

EXAMPLES

Unless otherwise noted, all solvents and chemical reagents were or can be obtained from Aldrich Chemical Co., Milwaukee, Wis. Aqueous buffers were obtained from Sigma Aldrich Co., Milwaukee, Wis. or were prepared by known methods.

Gold-coated silicon substrates were obtained from Wafer-Net, Inc., San Jose, Calif. and were 150 mm prime-grade N-type silicon wafers onto one side of which metal was deposited by reactive sputtering. The wafers were first treated to deposit, by reactive sputtering, a layer of chromium and were then treated to deposit, by reactive sputtering, a layer of gold. The thickness of the gold layer was 5000 Angstroms.

The IR and $^1$HNMR spectra of each product were consistent with the assigned structure.

Glossary

As used herein:

"DMF" refers to N,N-dimethylformamide;

"HSA" refers to human serum albumin, which was obtained from Jackson ImmunoResearch Laboratories, Inc., West Grove, Pa.;

"SA-HRP" refers to streptavidin conjugated with horseradish peroxidase, which was obtained from Jackson ImmunoResearch Laboratories, Inc.;

"ABTS" refers to 2,2'-azino-di-(3-ethylbenzthiazoline-6-sulfonate), which was obtained in kit form from KPL Inc., Gaithersburg, Md.;

"NMP" refers to N-methylpyrrolidinone;

"MBA" refers to the polymer formed by polymerizing methylenebis(acrylamide);

"DLC" refers to a diamond-like carbon coating prepared as described;

"DLG" refers to a diamond-like glass coating prepared as described;

"ELISA" refers to enzyme-linked immunoabsorbent assay;

"THF" refers to tetrahydrofuran;

"PBS" refers to phosphate buffered saline which has a pH of about 7.4;

"SDS" refers to sodium dodecyl sulfate;

"TWEEN 20" refers to polyoxyethylene(20) sorbitan monolaurate; and

"VAZO 64" refers to a trade designation for 2,2'-azobisisobutyronitrile available from Dupont Chemical Co., Wilmington, Del.

Methods

Contact Angle Measurements

Advancing and receding contact angles of deionized water were measured in air at room temperature using a Model 100 goniometer (available from Rame-Hart, Inc., Mountain Lakes, N.J.).

Ellipsometry

Ellipsometric determination of the monolayer thickness was carried out using a Model AutoEL ellipsometer (available from Rudolph Technologies, Inc., Flanders, N.J.) at a wavelength of 6320 Angstroms and at an angle of incidence of 70 degrees. For each substrate, ellipsometric constants were determined by extrapolation of self assembled monolayers of 1-mercaptohexadecane, 1-mercaptododecane, and 1-mercaptooctane. The ellipsometric thicknesses of the monolayers were estimated by using a three-layer model and by assuming the refractive index of 1.46 for the monolayer.

Preparative Example 1

Preparation of

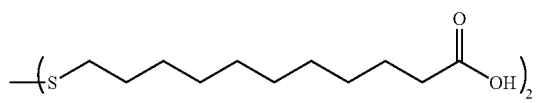

A solution of KOH (2.7 g) in ethanol (30.8 g) was magnetically stirred at room temperature. 11-Mercaptoundecanoic acid (5.0 g) was added slowly to the KOH solution. After the addition was complete, a solution of iodine (2.9 g) in ethanol (62.2 g) was added and the mixture was stirred for approximately one hour longer. The mixture was then poured into 1N aqueous HCl and the precipitated solid was isolated by filtration. The solid was washed with deionized water and was dried in air to afford 5.0 g of product.

Preparative Example 2

Preparation of

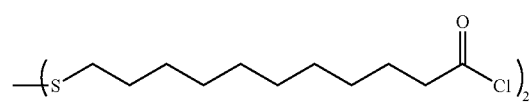

A mixture of the carboxy-containing product from Preparative Example 1 (2.0 g), thionyl chloride (1.15 g), and methylene chloride (12.6 g) was stirred and heated at reflux under a nitrogen atmosphere within a round bottom flask that was fitted with a magnetic stir bar, a reflux condenser, and a heating mantle. After 6 hours, the mixture was cooled to room temperature and the volatile components were removed using a rotary evaporator to afford the product.

Preparative Example 3

Preparation of

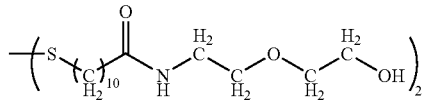

The chlorocarbonyl-containing product of Preparative Example 2 (10.9 g) dissolved in methylene chloride (30 mL) was added slowly to a magnetically stirred solution of 2-(2-aminoethoxy)ethanol (9.7 g) and N,N-diisopropylethylamine (6.27 g) in methylene chloride (37 mL) within a round bottom flask. During the addition, the flask was cooled in an ice bath. After the addition was complete, the mixture became very viscous. An attempt to extract the mixture with deionized water resulted in a heterogeneous partial emulsion. The volatile components were removed using a rotary evaporator and the remaining mixture was heated to boiling, which resulted in the precipitation of a white solid. This solid was filtered and was then dissolved in acetonitrile (250 mL). The acetonitrile solution was stirred and was concentrated by directing a stream of nitrogen gas onto the surface of the solution. The resultant white crystals were isolated by filtration and were dried overnight under a stream of nitrogen gas to afford 12.6 g of product.

Preparative Example 4

Preparation of

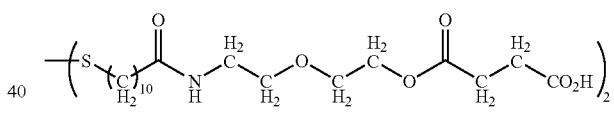

The mixture of the hydroxy-containing product of Preparative Example 3 (3.0 g), succinic anhydride (1.1 g), and triethylamine (1.15 g) was heated within an Erlenmeyer flask for 6 hours. The mixture was allowed to cool to room temperature and methyl alcohol was added to the flask. The product formed a dark thick liquid that was not miscible with the methyl alcohol. The methyl alcohol was decanted away from the dark residue and the product was then recrystallized from acetonitrile to afford 3.43 g of product.

Preparative Example 5

Preparation of

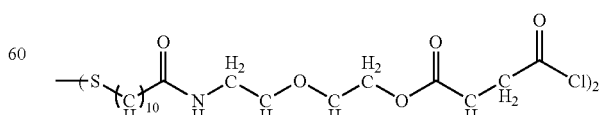

A mixture of the carboxy-containing product of Preparative Example 4 (0.5 g), thionyl chloride (0.15 g), DMF (1 drop), and dichloromethane (2.0 g) was magnetically stirred overnight. The volatile components were removed using a rotary evaporator to afford the product (0.52 g).

Preparative Example 6

Preparation of

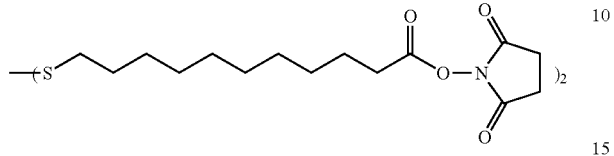

A mixture of the carboxy-containing product of Preparative Example 1 (2.0 g), thionyl chloride (1.15 g), and methylene chloride (12.6 g) was heated under reflux within a round bottom flask that was fitted with a reflux condenser, a hose adapter connected to a source of nitrogen gas, and a heating mantle. After 6 hours, the mixture was concentrated to dryness using a rotary evaporator. Methylene chloride (12.6 g) was added to the flask followed by dropwise addition of a mixture of N-hydroxysuccinimide (1.11 g) and pyridine (0.8 g). The mixture was stirred at room temperature overnight and then the volatile materials were removed using a rotary evaporator. The residue was recrystallized from isopropyl alcohol to afford 2.91 g of product.

Preparative Example 7

Attachment a N-acyloxysuccinimide Containing Tethering Group to Gold-Coated Silicon Substrate A 250-micromolar solution of the N-acyloxysuccinimide-containing product of Preparative Example 6 in acetone was prepared. A 1 cm by 1 cm portion of a gold-coated silicon wafer was immersed in the solution for 30 minutes, removed and rinsed sequentially with ethanol and methanol, and then dried by directing a stream of nitrogen gas over the treated gold surface for approximately 1 minute. The ellipsometric thickness was 17 Angstroms and the static advancing contact angle of deionized water on the surface was 50 degrees. The measurements were made on the layer of material attached to the gold layer of the substrate.

Preparative Example 8

Preparation of

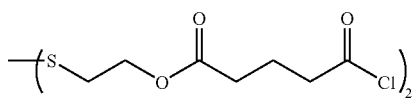

A mixture of 2-hydroxyethyl disulfide (4.0 g), glutaric anhydride (6.5 g) and triethylamine (6.1 g) were stirred together within a round bottom flask and was heated to 100° C. for six hours. After the mixture was allowed to cool to room temperature, the product was taken up in ethyl acetate and this solution was washed sequentially with 1N aqueous HCl and saturated aqueous NaCl. The solution was dried over MgSO$_4$ and then filtered. Thionyl chloride (6.8 g) and DMF (1 drop) was added to the filtrate within a round bottom flask fitted with a magnetic stir bar and a reflux condenser. The mixture was stirred and heated under reflux for two hours and then cooled to room temperature. The volatile components were removed using a rotary evaporator to afford the product.

Preparative Example 9

Preparation of

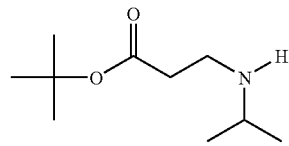

A mixture of t-butyl acrylate (6.9 g) and isopropyl amine (3.2 g) in a round bottom flask was magnetically stirred at room temperature for approximately 6 hours. Analysis of the mixture by gas chromatography indicated that the reaction was not complete. An additional charge of isopropyl amine (3.2 g) was added to the flask and the mixture was magnetically stirred overnight at room temperature. The volatile components were removed using a rotary evaporator to afford 10 g of product.

Preparative Example 10

Preparation of

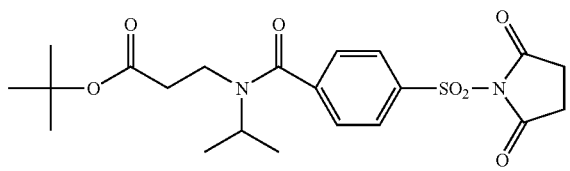

A solution of the t-butyl ester product of Preparative Example 9 (1.3 g), triethyl amine (0.74 g), and NMP (4.2 g) was slowly added to a solution of the carbonyl chloride product of Example 5 (2.0 g) in NMP (9 g) in a round bottom flask that was cooled in an ice bath. The ice bath was removed and the mixture was magnetically stirred for approximately 6 hours as the mixture warmed to room temperature. The mixture was then poured into 1N aqueous HCl and this mixture was extracted with ethyl acetate. The organic phase was washed with saturated aqueous NaCl and was dried over MgSO$_4$, after which it was filtered. The filtrate was concentrated to dryness using a rotary evaporator and the residue was recrystallized from methanol to afford 1.14 g of product.

Preparative Example 11

Preparation of

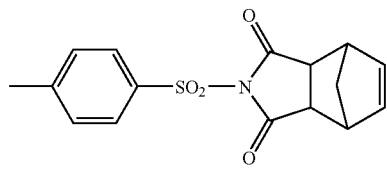

A 3-neck round bottom flask, fitted with a magnetic stir bar, an addition funnel and a hose adapter that was connected to a source of nitrogen gas, was charged with a 60 weight percent dispersion of NaH in mineral oil (9.45 g) and hexane (20 mL). The mixture was stirred for approximately 15 minutes after which DMF (100 mL) was added to the flask. A mixture of p-toluenesulfonamide (15.7 g) and 5-norbornene-2,3-dicarboxylic anhydride (16.2 g) in DMF (100 mL) was slowly added to the flask from the addition funnel. The mixture was allowed to stir overnight at room temperature. A solution of 5-norbornene-2,3-dicarboxylic anhydride (1.6 g) in DMF (10 mL) was added dropwise to the flask and the mixture was stirred for approximately 6 hours. Acetic anhydride (28.14 g) was then added to the flask and the mixture was stirred overnight. Aqueous $NaHCO_3$ solution was then added to the flask, followed by aqueous HCl. The mixture was filtered and the filtered solid was dried overnight using a vacuum oven. The solid was then recrystallized from methanol to afford 14.8 g of product.

Preparative Example 12

Preparation of

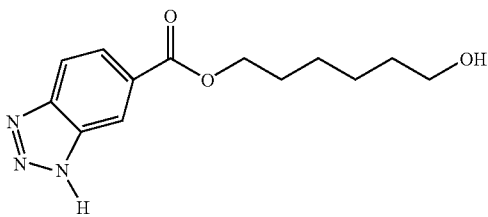

A mixture of benzotriazole-5-carboxylic acid (5.7 g), 1,6-hexanediol (24.7 g), and p-toluenesulfonic acid were stirred together within a round bottom flask at 125° C. while a stream of dry nitrogen gas was slowly bubbled through the liquid. The mixture became homogeneous and, after 12 hours, triethylamine (0.42 g) was added to the flask. Volatile components were removed using a rotary evaporator and the residue was taken up in ethyl acetate. The ethyl acetate solution was washed with saturated aqueous NaCl, dried over $MgSO_4$ and concentrated to dryness using a rotary evaporator. The residue was taken up in boiling acetonitrile and this solution was cooled to room temperature and further cooled in an ice bath. The tan crystals that formed were isolated by filtration, washed with cold acetonitrile and dried in air at room temperature to afford 2.97 g of product.

Preparative Example 13

Preparation of a Multilayer Substrate of DLG-DLC-polyimide-DLC-DLG

A Model 2480 parallel-plate capacitively coupled reactive ion etcher (obtained from PlasmaTherm, St. Petersburg, Fla.) was used to deposit a diamond-like glass (DLG) coating using a tetramethylsilane plasma onto a diamond-like carbon coating (DLC). The DLC coating was deposited using an acetylene plasma with the Model 2480 reactive ion etcher onto a polyimide film.

An approximately 20 cm by 30 cm sample of polyimide film (available under the trade designation "KAPTON E" from E.I. du Pont de Nemours & Co., Wilmington, Del.) was affixed to the powered electrode of the ion etcher using 3M 811 Adhesive Tape from 3M Company, St. Paul, Minn. The ion etcher chamber was closed and the chamber was pumped to a pressure of 0.67 Pa (0.005 Torr). Oxygen gas was introduced into the chamber at a flow rate of 500 standard $cm^3$ per minute, and the pressure of the chamber was maintained at 6.7 Pa (0.050 Torr). Plasma was ignited and was sustained at a power of 2000 W for 15 seconds. The oxygen gas flow was then terminated and the chamber was allowed to pump to a pressure of 0.67 Pa (0.005 Torr). Acetylene gas was then introduced into the chamber at a flow rate of 200 standard $cm^3$ per minute, and the pressure of the chamber was maintained at 2 Pa (0.015 Torr). Plasma was ignited and was sustained at a power of 1600 W for 10 seconds. The flow of acetylene gas was then terminated and the chamber was allowed to pump to a pressure of 0.67 Pa (0.005 Torr).

Oxygen gas was again introduced into the chamber at a flow rate of 500 standard $cm^3$ per minute and, the pressure of the chamber was maintained at 20 Pa (0.15 Torr). Plasma was ignited and was sustained at a power of 300 W for 10 seconds. With the oxygen gas flow rate maintained at 500 standard $cm^3$ per minute, tetramethylsilane gas was introduced into the chamber at a flow rate of 150 standard $cm^3$ per minute. The chamber pressure was maintained at 20 Pa (0.15 Torr). Plasma was ignited and was sustained at a power of 300 W for 12 seconds. The flow of tetramethylsilane gas was terminated. After a period of 1 minute, with both the flow of oxygen gas and the chamber pressure of 20 Pa (0.15 Torr) maintained, plasma was ignited and was sustained at a power of 300 W for 20 seconds. The flow of oxygen gas was then terminated and the chamber pressure was allowed to pump to a pressure of 0.67 Pa (0.005 Torr). The chamber was then opened to the atmosphere and the sample of polyimide film was removed from the powered electrode, turned so that the DLG coating faced the electrode, and was again affixed to the electrode. The sequence of plasma treatments was repeated to provide a sample of polyimide film with sequential layers of DLC and DLG on each side.

Preparative Example 14

Preparation of Multilayer Substrate of Glass-DLC-DLG

A 25 mm by 75 mm glass microscope slide (available as "MICRO SLIDES SELECTED" from VWR Scientific, West Chester, Pa.) was treated in a plasma chamber according to the method of Preparative Example 13 to sequentially deposit layers of DLC and DLG onto one side of the glass microscope slide.

Preparative Example 15

Preparation of Multilayer Substrate of Polyimide-titanium-gold

Sequential layers of titanium and gold were deposited by electron beam evaporation onto polyimide film. A 10 cm by 15 cm sample of polyimide film (available under the trade designation "KAPTON E" from E. I. Du Pont de Nemours & Co., Wilmington, Del.) was affixed to the plate of the planetary system in a Model Mark 50 high vacuum deposition system (available from CHA Industries, Fremont, Calif.) using metal stationery binder clips. The chamber was evacuated for approximately 2 hours, during which time the chamber pressure was reduced to approximately $6.7 \times 10^{-4}$ Pa ($5 \times 10^{-6}$ mm Hg). Titanium metal was deposited at a rate of approximately 5 Angstroms per second to a total thickness of approximately 200 Angstroms. Deposition of titanium was then terminated and the system was allowed to cool for approximately 30 minutes. Gold metal was then deposited onto the titanium layer at a rate of approximately 1 Angstrom per second to a total thickness of approximately 2000 Angstroms. Deposition of gold was then terminated and the system was allowed to cool for approximately 30 minutes before the chamber pressure was raised to atmospheric pressure and the samples were removed.

Preparative Example 16

Preparation of Acid Chloride Functionalized Poly(methylmethacrylate-co-methacrylic acid) Beads Poly(methylmethacrylate-co-methacrylic acid) beads (available in ethanol under the trade designation "MACRO-PREP CM" from Bio-Rad Laboratories, Hercules, Calif.) were filtered using a fritted glass funnel and were then dried overnight using a vacuum oven at 40° C. into which nitrogen gas was slowly introduced such that the pressure was maintained at less than about 133.3 Pa (1 mm Hg). The dried beads (approximately 100 g) were combined with 1N aqueous HCl (approximately 750 mL) in a glass jar overnight.

The beads were then filtered, washed successively with deionized water, isopropyl alcohol and diethyl ether, and dried overnight using a vacuum oven at 40° C. into which nitrogen gas was slowly introduced such that the pressure was maintained at less than about 133.3 Pa (1 mm Hg). A portion of these dried beads (39.81 g) was combined with acetonitrile (112.5 g), thionyl chloride (8.0 g), and DMF (3 drops) in a round bottom flask fitted with a magnetic stir bar, a reflux condenser and a source of nitrogen gas. The mixture was heated under reflux for 4 hours, after which time it was allowed to cool to room temperature and was then magnetically stirred overnight. The mixture was filtered and the beads were washed with acetonitrile and then with diethyl ether. The product was dried at room temperature to constant weight.

Preparative Example 17

Preparation of Hydroxyl Functionalized Poly(methylmethacrylate-co-methacrylic acid) Beads The acid chloride functionalized beads of Preparative Example 16 (10.0 g) were poured into a rapidly stirring mixture of pyridine (1.42 g) and tetraethylene glycol (26.17 g). The mixture was heated to approximately 50° C. and was stirred at that temperature overnight. After the mixture was allowed to cool to room temperature, it was filtered using a fritted glass funnel and then the beads were washed successively with isopropyl alcohol, methanol, deionized water and methanol. The beads were dried by drawing nitrogen gas through them in the fritted glass funnel to constant weight.

Preparative Example 18

Preparation of a Substrate of MBA Beads

MBA beads (0.62 g, available under the trade designation "ULTRALINK BIOSUPPORT MEDIUM" from Pierce Biotechnology, Rockford, Ill.) were suspended in dichloromethane (10 g) in a screw cap vial by magnetically stirring the mixture. N-Propyl amine (0.19 g) was added, the vial was sealed, and the mixture was magnetically stirred at room temperature overnight. The beads were then filtered and were washed with dichlormethane and were again filtered. The beads were dried by drawing nitrogen gas through them in the filter funnel.

Example 1

Preparation of 4-aminobenzenesulfonyl Succinimide

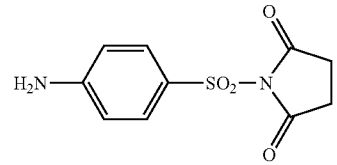

A suspension of NaH in dry DMF was prepared by successively washing 8.4 g of a 60 wt % mixture of NaH and mineral oil with three portions of heptane in a round bottom flask. DMF (25 mL) was then added to the flask and the solid was suspended by agitating the flask. This suspension of NaH in DMF was added in one portion to a flask that contained a solution of succinic anhydride (11.0 g) in 30 mL of dry DMF. The resultant suspension was stirred while a solution of sulfanilamide (17.2 g) in 25 mL of dry DMF was added over a period of about 10 minutes. The mixture was stirred overnight at room temperature and then acetic anhydride (10.2 g) was added in one portion. The mixture was stirred for an additional three hours and was then poured into deionized water. As this mixture was stirred, the product slowly solidified. The solid was filtered, washed with deionized water, and then dried to give 7.6 g of product.

Example 2

Preparation of

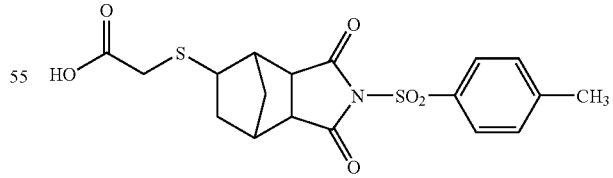

A solution of the N-(4-methylbenzenesulfonyl)dicarboximide product of Preparative Example 11 (25.0 g) and mercaptoacetic acid (7.63 g) in ethyl acetate (161 g) within a 3-neck round bottom flask was purged with nitrogen gas for 10 minutes. The flask was fitted with a reflux condenser and a magnetic stir bar. Azobis(isobutyronitrile) (0.0484 g) was added to the flask and the mixture was stirred and heated at 55° C. for sixteen hours. After the mixture had cooled to room temperature, the solvent was removed using a rotary evaporator. The brown solid was recrystallized from toluene/acetonitrile to give 11.9 g of product.

Example 3

Preparation of

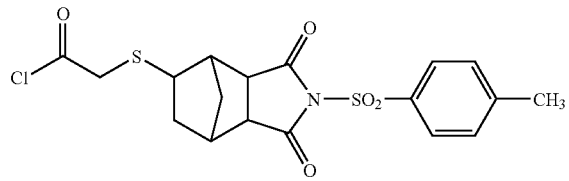

A mixture of the carboxy-containing product of Example 2 (5.06 g), thionyl chloride (1.62 g), DMF (1 drop), and chloroform (61.8 g) was made within a 100 mL round bottom flask. The flask was fitted with a magnetic stir bar and a reflux condenser and then the mixture was stirred and heated under reflux for two hours. The mixture was allowed to cool to room temperature and then heptane was added to the flask until the product precipitated. The mixture was filtered and the product was dried in a vacuum oven to give 4.8 g of product.

Example 4

Preparation of

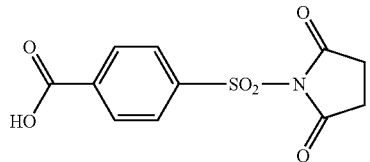

A mixture of DMF (154 mL), 4-carboxybenzenesulfonamide (30.0 g), succinic anhydride (16.41 g), and triethylamine (33.19 g) within a round bottom flask was stirred and heated to 50° C. under a nitrogen atmosphere for four hours. The mixture was allowed to cool to room temperature and then acetic anhydride (18.27 mL) was added and the mixture was stirred at room temperature for an additional three hours. The mixture was then poured into 400 mL of stirred 1N aqueous HCl. This mixture was filtered and the tan precipitate was washed with deionized water and dried in a vacuum oven to afford 36.94 g of product.

Example 5

Preparation of

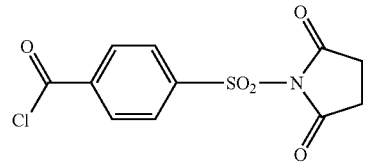

Thionyl chloride (10.0 g) and DMF (1 drop) were added to a stirred mixture of the carboxy-containing product of Example 4 (20.0 g) and dry acetonitrile (85 g) within a round bottom flask. This mixture was stirred and heated under reflux for one hour. The mixture was cooled to room temperature and further cooled in an ice bath, which resulted in the formation of a solid precipitate. The solid was collected by filtration, washed sequentially with cold acetonitrile and cold toluene, and dried overnight in a vacuum oven at 50° C. to give 17.7 g of product.

Example 6

Preparation of

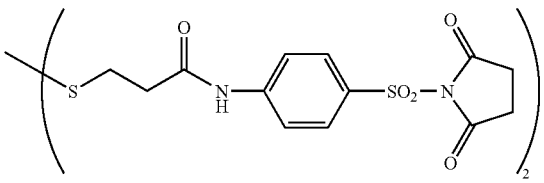

A mixture of 3,3'-dithiobis(propionic acid) (5.0 g), thionyl chloride (2.97 g), DMF (1 drop), and ethyl acetate (24 mL) was placed within a round bottom flask fitted with a magnetic stir bar and a reflux condenser. The mixture was stirred and heated to reflux for two hours. The mixture was allowed to cool to room temperature and then the volatile components were removed using a rotary evaporator. The residue was dissolved in dry NMP (13.1 mL) and this solution was added to a cold stirred solution of sulfanilamide (4.5 g) and pyridine (2.2 g) in dry NMP. The mixture was warmed to room temperature, stirred for an additional two hours, and then poured into deionized water (100 mL) with stirring. The solid that formed was filtered and was dried overnight in a vacuum oven at room temperature and at a pressure of 133.3 Pa (1 mm Hg) to afford 6.25 g of solid.

This solid was dissolved in dry DMF (21.6 mL) with succinic anhydride (2.99 g) and triethylamine (2.65 g) in a round bottom flask that was fitted with a magnetic stir bar and a reflux condenser. The mixture was heated to 90° C. and was stirred at that temperature for eight hours. After the mixture was allowed to cool to room temperature, acetic anhydride (1.28 g) was added and the mixture was stirred at room temperature for an additional one hour. The mixture was then poured into deionized water in a beaker and the resultant mass was triturated with deionized water and isopropyl alcohol until a solid formed. The solid was filtered and dried and was then recrystallized from a mixture of acetic acid and acetic anhydride. The resultant crystalline solid was filtered and was washed sequentially with acetic acid, isopropyl alcohol and diethyl ether and was dried in air at room temperature to afford 5.7 g of product.

Example 7

Preparation of

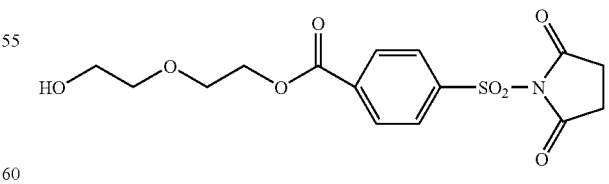

Dry diethylene glycol (12.0 g) and the acid chloride product of Example 5 (3.0 g) were stirred together within a round bottom flask fitted with a magnetic stir bar. After three hours, the mixture was poured into deionized water with vigorous stirring and the resultant solid was collected by filtration, washed with deionized water, and dried in a vacuum oven at room temperature overnight at 133.3 Pa (1 mm Hg). The crude material was recrystallized from methanol to afford 2.21 g of product.

Example 8

Preparation of

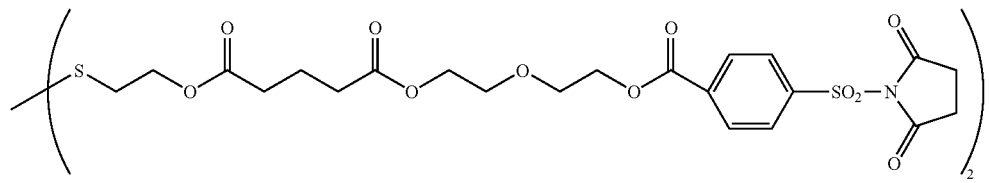

The alcohol product of Example 7 (1.5 g), the dithiobis (acid chloride) product of Preparative Example 8 (0.81 g), and pyridine (0.35 g) were combined at 10° C. with acetonitrile (11.9 g) within a round bottom flask that was fitted with a magnetic stir bar. Pyridine (0.35 g) was added to the flask and the mixture was stirred at room temperature for two hours. The mixture was then poured into deionized water in a beaker and that mixture was stirred vigorously. The solid precipitate that formed was isolated by filtration and was washed with deionized water. The solid was dried in a vacuum oven overnight and was then recrystallized from isopropyl alcohol to afford 1.7 g of product.

Example 9

Preparation of

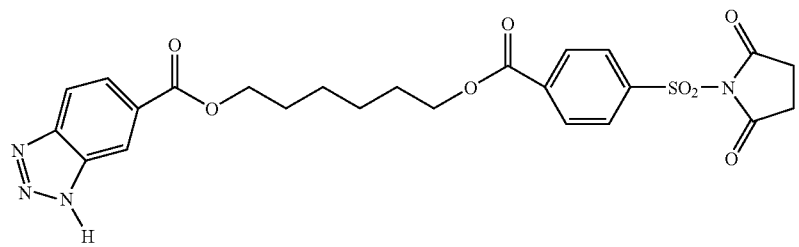

A solution of the benzotriazole alcohol product of Preparative Example 12 (1.0 g) in NMP (2.4 mL) was cooled to approximately −5° C. within a round bottom flask fitted with a magnetic stir bar. A solution of the carbonyl chloride product of Example 5 (1.1 g) in NMP (2.5 mL) was added slowly to the flask, followed by pyridine (0.3 g). The mixture was then allowed to warm to room temperature and was stirred overnight. The mixture was poured into deionized water in a beaker and the aqueous mixture was extracted with ethyl acetate. The organic phase was washed successively with deionized water and saturated aqueous NaCl and then dried over MgSO$_4$. The solution was filtered and the filtrate was concentrated to dryness using a rotary evaporator. The resultant solid was recrystallized from isopropyl alcohol to afford 0.86 g of tan crystals.

Example 10

Preparation of

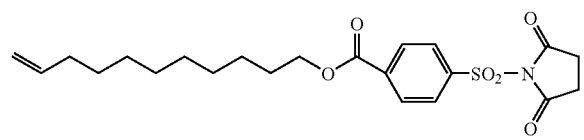

A solution of the carbonyl chloride product of Example 5 (5.0 g) in dry NMP (20 g) was placed within a round bottom flask fitted with a magnetic stir bar and cooled in an ice bath. A solution of 10-undecen-1-ol in dry NMP (13.5 g) was added slowly to the flask. The stirring mixture was warmed to room temperature and stirred for approximately 6 hours. The mixture was then poured into deionized water in a beaker and the resultant solid precipitate was isolated by filtration and washed successively with deionized water, isopropyl alcohol and diethyl ether. The product was dried in air at room temperature overnight and then recrystallized from acetic acid to afford 4.25 g of white crystals.

Example 11

Preparation of

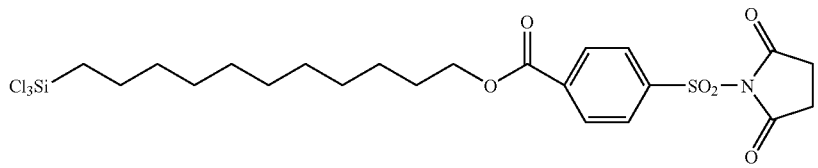

A solution of the alkene product of Example 10 (2.63 g) and HSiCl₃ (3.5 g) in methylene chloride (35 g) was prepared in a 125 mL screw cap bottle. Platinum(0)-1,3-divinyl-1,1,3,3-tetramethyldisiloxane complex in xylenes was diluted with methylene chloride to a concentration of approximately 1.5 weight percent, and 3 drops of this solution were added to the bottle. The bottle was then sealed and was heated to 60° C. in a water bath. After 30 hours, the mixture was allowed to cool to room temperature. The volatile components were removed using a rotary evaporator to afford 2.3 g of the product.

Example 12

Preparation of

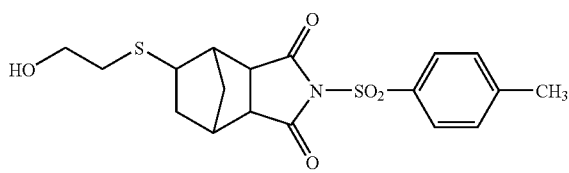

A mixture of 2-mercaptoethanol (1.69 g), the N-(4-methylbenzenesulfonyl)succinimide product of Preparative Example 11 (7.0 g), VAZO 64 (0.2 g), and ethyl acetate (8.7 g) was purged with nitrogen gas for approximately 15 minutes and was then heated at 55° C. under a nitrogen atmosphere for 24 hours. The solution was allowed to cool to room temperature, during which time white crystals precipitated. The crystals were isolated by filtration, washed with ethyl acetate and dried to afford 3.2 g of product.

Example 13

Preparation of

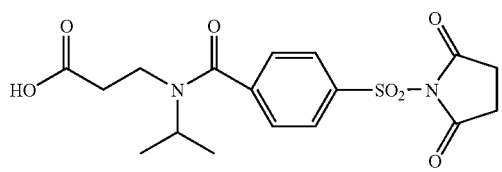

The tertiary butyl ester product of Preparative Example 10 (0.95 g) was combined with acetic acid (2.2 g), acetic anhydride (1 drop), and p-toluenesulfonic acid (approximately 0.005 g). The mixture was stirred and heated at 70° C. for one hour. The mixture was cooled slightly and the volatile components were removed using a rotary evaporator. The resultant brown oil was triturated with diethyl ether, which resulted in solidification of most of the residue. The solid was isolated by filtration, washed with diethyl ether, and dried in air at room temperature overnight to afford 0.6 g of product.

Example 14

Preparation of

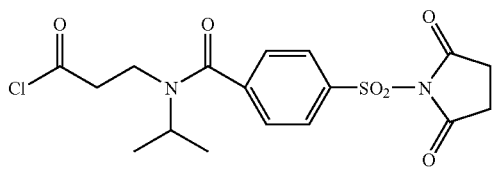

The carboxylic acid product of Example 13 (0.6 g) was combined with thionyl chloride (0.37 g), acetonitrile (2.44 g), and DMF (1 drop) in a round bottom flask that was fitted with a magnetic stir bar, a reflux condenser, and a heating mantle. The mixture was stirred and heated at reflux for 1 hour, after which time it was allowed to cool to room temperature. The volatile components were then removed using a rotary evaporator. The resultant solid was washed into a fritted glass funnel, washed with diethyl ether, and dried at room temperature under a stream of nitrogen gas to the product.

Example 15

Preparation of

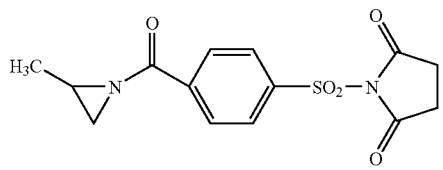

A solution of the acid chloride product of Example 5 (3.0 g), and NMP (12.8 g) was magnetically stirred within a round bottom flask as the mixture was cooled in an ice bath. A mixture of 2-methylaziridine (0.62 g) and triethylamine (1.11 g) was slowly added to the flask and then the ice bath was removed. The mixture was allowed to warm to room temperature and was magnetically stirred overnight. The mixture was then poured into saturated aqueous sodium bicarbonate and this mixture was extracted with ethyl acetate. The organic phase was dried over sodium carbonate and the mixture was then filtered. The volatile components were removed using a rotary evaporator to afford the product.

Example 16

Preparation of

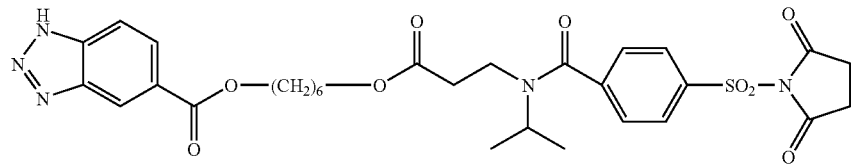

A solution of the acid chloride product of Example 14 (0.63 g) in NMP (1.5 g) was prepared within a round bottom flask fitted with a magnetic stir bar. The solution was stirred as it was cooled in an ice bath. A solution of the benzotriazole alcohol product of Preparative Example 12 (0.4 g), pyridine (0.23 g), and NMP (0.9 g) was prepared and this solution was slowly added to the solution of the acid chloride. The ice bath was removed and the solution was allowed to warm to room temperature. The entire reaction mixture was then combined with ethyl acetate (50 mL) and this solution was washed with 1N aqueous HCl and then with aqueous NaCl. The solution was then dried over anhydrous MgSO4, after which time it was filtered and the filtrate was then concentrated to dryness using a rotary evaporator. The residue was then triturated with diethyl ether and the resultant solid was isolated by filtration, washed with diethyl ether, and then dried in air at room temperature to afford 0.96 g of product.

Example 17

Preparation of

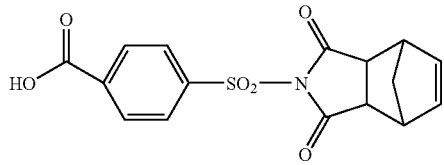

A mixture of norbornene-2,3-dicarboxylic anhydride (26.9 g), p-sulfamylbenzoic acid (30.0 g), triethylamine (49.8 g) and DMF (82 g) was magnetically stirred under a nitrogen atmosphere within a round bottom flask for two hours at 50° C. and then heating was continued overnight at 90° C. The mixture was then cooled to room temperature and acetic anhydride (18.3 g) was added to the flask. The mixture was stirred overnight at room temperature. The mixture was then poured into aqueous IN HCl and the resultant solid was isolated by filtration and dried using a vacuum oven. The product was recrystallized from glacial acetic acid to afford a total of 12.6 g.

Example 18

Preparation of

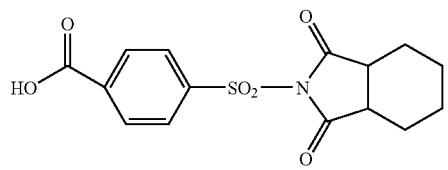

A mixture of cyclohexane-1,2-dicarboxylic anhydride (25.3 g), p-sulfamylbenzoic acid (30.0 g), triethylamine (49.8 g), and DMF (79 g) was magnetically stirred under a nitrogen atmosphere in a round bottom flask overnight at 50° C. The mixture was then allowed to cool to room temperature and acetic anhydride (18.3 g) was slowly added to the flask. The mixture was stirred for one hour and then poured into aqueous 1N HCl. The resultant solid was isolated by filtration, washed sequentially with isopropyl alcohol, methanol, and diethyl ether and dried using a vacuum oven to afford 41.23 g of product.

Example 19

Preparation of

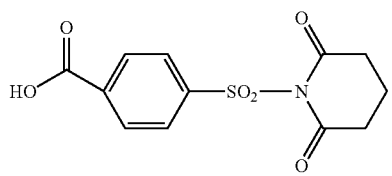

A mixture of glutaric anhydride (18.7 g), p-sulfamylbenzoic acid (30.0 g), triethylamine (49.8 g), and DMF (71 g) was magnetically stirred under a nitrogen atmosphere within a round bottom flask for 6 hours at 50° C. and then overnight at room temperature. Acetic anhydride (18.3 g) was slowly added to the flask and the mixture was stirred overnight at room temperature. The mixture was poured into 1N aqueous HCl. The resultant solid was isolated by filtration, washed sequentially with isopropyl alcohol, methanol and diethyl ether, and dried in a vacuum oven to afford 30 g of product that appeared to be impure, based on ¹HNMR analysis. This material (28.7 g) was combined with glutaric anhydride (9.5 g), triethylamine (24.9 g), DMF (38.5 g) and this mixture was stirred and heated overnight at 50° C. The mixture was then allowed to cool to room temperature and acetic anhydride (9.15 g) was added to the flask. The mixture was stirred at room temperature overnight after which time it was poured into 1N aqueous HCl. The resultant solid was isolated by filtration, washed sequentially with isopropyl alcohol, methanol and diethyl ether, and was dried in a vacuum oven. The solid was recrystallized from glacial acetic acid to give 20 g of product.

Example 20

Preparation of

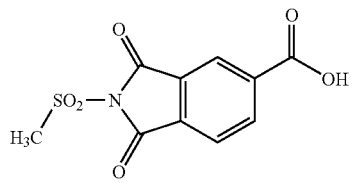

A mixture of methane sulfonamide (10 g), 1,2,4-benzenetricarboxylic anhydride (26.3 g), triethylamine (37.2 g), and DMF (84.6 g) was magnetically stirred under a nitrogen atmosphere overnight at room temperature. The mixture was then heated to 50° C. and stirred at this temperature for 30 minutes, after which time it was allowed to cool to room temperature and was filtered. The solid was recrystallized from glacial acetic acid and the white crystalline solid was filtered, washed with diethyl ether, and dried to afford 5.4 g of product.

Example 21

Preparation of

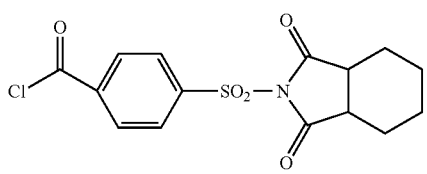

A mixture of the carboxylic acid product of Example 18 (10.0 g), thionyl chloride (4.58 g), DMF (1 drop), and acetonitrile (58.3 g) within a round bottom flask fitted with a condenser was magnetically stirred under a nitrogen atmosphere under reflux for 1 hour. The mixture was allowed to cool to room temperature and the volatile components were removed using a rotary evaporator. The resultant solid was washed into a fritted glass funnel, washed with diethyl ether, and dried at room temperature under a stream of nitrogen gas to afford 8.3 g of product.

Example 22

Preparation of

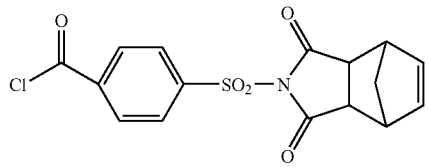

A mixture of the carboxylic acid product of Example 17 (5.0 g), thionyl chloride (2.2 g), DMF (1 drop) and acetonitrile (28.9 mL) within a round bottom flask fitted with a reflux condenser was magnetically stirred under a nitrogen atmosphere at reflux for 1 hour. The mixture was allowed to cool to room temperature and the volatile components were removed using a rotary evaporator. The resultant solid was washed into a fritted glass funnel, washed with diethyl ether, and then dried at room temperature under a stream of nitrogen gas to afford 4.7 g of product.

Example 23

Preparation of

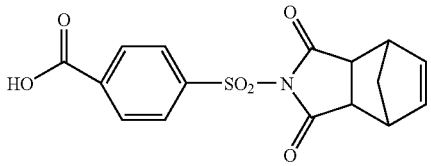

A mixture of bicyclo[2.2.2]octa-2-ene-5,6-dicarboxylic anhydride (10.0 g), p-sulfamylbenzoic acid (10.3 g), triethylamine (17.1 g) and DMF (45 g) was magnetically stirred in a round bottom flask at 90° C. for two hours. Analysis of the infrared spectrum of the mixture indicated that some of the starting anhydride was still present. Additional DMF (36 g) was added to the flask and the mixture was stirred overnight at 90° C. Additional DMF was added to the heterogeneous mixture until a clear solution resulted. Heating and stirring were continued for an additional 4 hours. The mixture was cooled to room temperature and then acetic anhydride (6.25 g) was added to the flask. This mixture was stirred overnight at room temperature. The mixture was poured into 1N aqueous HCl. The resultant solid was isolated by filtration, washed sequentially with isopropyl alcohol, methanol and diethyl ether, and was dried in a vacuum oven. The solid was recrystallized from glacial acetic acid to afford 12.8 g of product.

Example 24

Preparation of

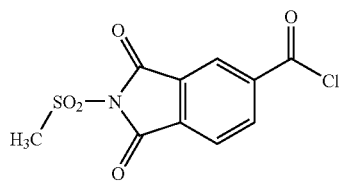

A mixture of the carboxylic acid product of Example 20, (3.0 g), thionyl chloride (1.72 g), DMF (1 drop), and acetonitrile (18.9 g) within a round bottom flask fitted with a reflux condenser was magnetically stirred under a nitrogen atmosphere at reflux for 1 hour. The volatile components were then removed using a rotary evaporator and the partially solid residue in the flask was washed into a fritted glass funnel with diethyl ether. The solid was washed with diethyl ether and was dried under a flow of nitrogen gas to afford 2.9 g of product.

Example 25

Preparation of

A solution of 11,11'-dithiobis(undecan-1-ol) (0.38 g) in NMP (2 g) was prepared in a round bottom flask which was fitted with a magnetic stir bar and a hose adapter that was connected to a source of nitrogen gas. Separately, a mixture of the acid chloride product of Example 22 (0.79 g) in NMP (2.7 g) was prepared and this mixture was added slowly to the flask. The mixture was stirred overnight and then the mixture was poured into 0.1N aqueous HCl within a beaker. The resultant solid was filtered and then washed sequentially with isopropyl alcohol, methanol, and diethyl ether. The filtered solid was then dried at room temperature to afford the product.

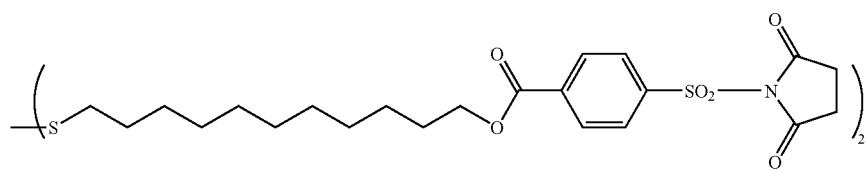

A solution of the carboxylic acid product of Example 5, (1.2 g) and THF (5.0 g) was stirred in a round bottom flask fitted with a pressure-equalizing addition funnel. The flask was partially immersed in a bath of cold tap water. A solution of 11,11'-dithiabis(undecan-1-ol) (0.75 g), pyridine (0.32 g), and THF (2.7 g) was slowly added to the flask via the addition funnel. The mixture was stirred overnight and then the volatile components were removed using a rotary evaporator. The residue was recrystallized from isopropyl alcohol to afford 0.65 g of product.

Example 26

Preparation of

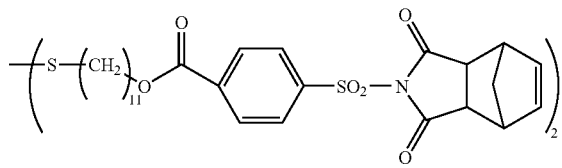

Example 27

Preparation of

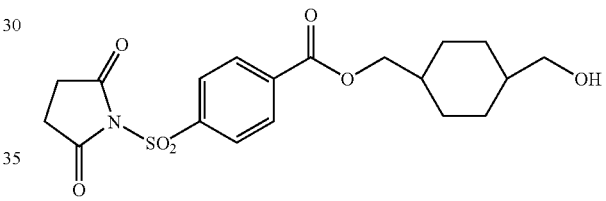

A solution of 1,4-bis(hydroxymethyl)cyclohexane (3.82 g) in NMP (5 g) was stirred within a round bottom flask in an ice bath while a solution of the acid chloride product of Example 5 (2.0 g) in NMP (8.6 g) was slowly added to the flask. The ice bath was then removed and the mixture was allowed to warm to room temperature. The mixture was stirred overnight and then mixed with deionized water. The mixture was then extracted with ethyl acetate. The ethyl acetate fraction was washed two times with deionized water and once with saturated aqueous NaCl. The solution was then dried over MgSO₄ and filtered. Removal of the volatile components using a rotary evaporator afforded 1.95 g of product.

Example 28

Preparation of

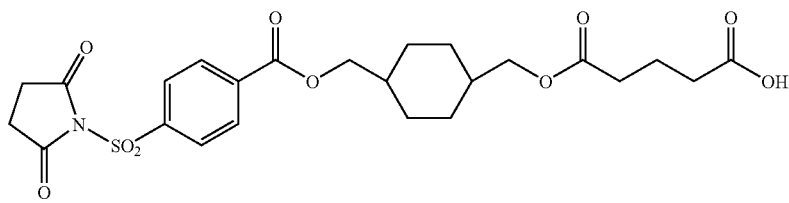

A mixture of the alcohol product of Example 27 (1.95 g), glutaric anhydride (0.83 g), pyridine (0.63 g), and DMF (11.13 g) was stirred at room temperature in a round bottom flask. After 4 hours, more glutaric anhydride (0.17 g) was added to the flask and the mixture was allowed to stir overnight at room temperature. The mixture was then poured into 0.1N aqueous HCl in a beaker. The resultant solid was filtered and washed sequentially with isopropyl alcohol and methanol. The solid was dried in a vacuum oven overnight at room temperature and 67 Pa (0.5 mm Hg) to afford 3.4 g of product.

Example 29

Preparation of

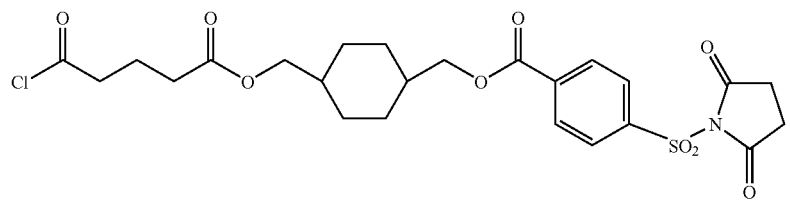

A mixture of the carboxylic acid product of Example 28 (3.5 g), thionyl chloride (1.18 g), DMF (1 drop), and acetonitrile (18.73 g) was stirred overnight at room temperature within a round bottom flask that was fitted with a magnetic stir bar, a reflux condenser, and a hose adapter that was connected to a source of nitrogen gas. The mixture was then heated, at a temperature that was just below that at which the mixture refluxed, for 4 hours. The mixture was then allowed to cool to room temperature and added to an excess of toluene. The solid was retained as the organic liquid mixture was decanted away. The solid was suspended in diethyl ether, filtered, washed with diethyl ether, and dried under a stream of nitrogen gas to afford the product.

Example 30

Preparation of

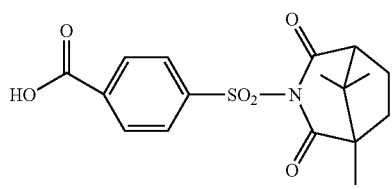

A 3-neck round bottom flask, fitted with a reflux condenser, a thermometer, a pressure-equalizing addition funnel, a magnetic stir bar, and a hose adapter connected to a source of nitrogen gas, was charged with 16.22 g of a 60 weight percent dispersion of NaH in mineral oil. The dispersion was washed three times with heptane by stirring the mixture for several minutes, allowing the mixture to stand, and then using a pipette to remove the supernatant heptane. NMP (50 g) was then added to the flask and the mixture was stirred. A solution of camphoric anhydride (14 g), 4-carbomethoxybenzenesulfonamide (15 g), and NMP (61 g) was slowly added to the flask using the addition funnel. The mixture was then stirred at room temperature for approximately 1 hour and then poured into deionized water within a beaker. This mixture was then extracted with ethyl acetate and the volatile components were removed using a rotary evaporator to afford a solid intermediate.

The intermediate was combined with THF (111 g), acetic anhydride (8.54 g), and triethylamine (23.3 g) and then stirred for 1 hour at 60° C. The mixture was then poured into aqueous 1N HCl in a beaker and the resultant solid was isolated by filtration. The solid was combined with methanol and this mixture was heated to boiling, cooled to room temperature, filtered, and washed sequentially with methanol and diethyl ether. The solid was dried overnight in a vacuum oven at room temperature and 67 Pa (0.5 mm Hg) to afford the product.

Example 31

Preparation of

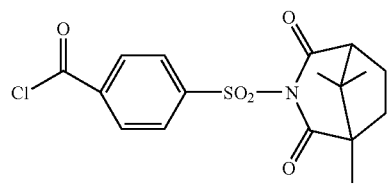

A 3-neck round bottom flask, fitted with a magnetic stir bar, reflux condenser, digital temperature probe, rubber septum, and a hose adapter connected to a source of nitrogen gas, was charged with a mixture of the carboxylic acid product of Example 30 and acetonitrile (20 g). The flask was placed in an ice bath and a 20 weight percent solution of phosgene in toluene (15.57 g) that was obtained from Fluka Holding AG, Buchs, Switzerland was added slowly via syringe. The mixture was then allowed to warm to room temperature and then heated at reflux. Periodically, the atmosphere above the reaction mixture was tested for the presence of phosgene using phosgene indicator paper. When no phosgene could be detected in this way, the flask was fitted with a distillation head and a small amount of the volatile materials were distilled away. The mixture was then filtered and the solid was dried under a stream of nitrogen gas to afford the product.

Example 32

Preparation of

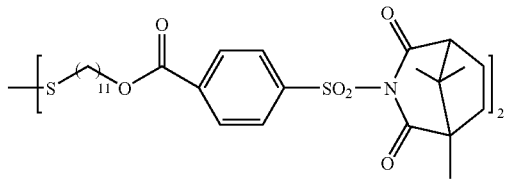

A mixture of 11,11'-dithiobis(undecan-1-ol) (0.37 g), the acid chloride product of Example 31, triethylamine (0.21 g), and chloroform (4.7 g) was magnetically stirred overnight at room temperature. The mixture was then washed with saturated aqueous $NaHCO_3$, washed with saturated aqueous NaCl, and dried over $Na_2SO_4$. The mixture was filtered and the volatile components were removed from the filtrate using a rotary evaporator. The resultant solid was dried overnight using a vacuum oven at room temperature and 67 Pa (0.5 mm Hg) to afford the product.

Example 33

Preparation of

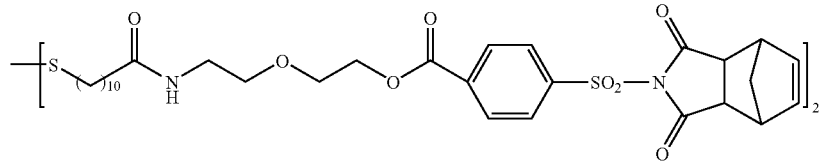

The chlorocarbonyl containing product of Example 22 (0.88 g) was added to a stirred solution of the alcohol product of Preparative Example 3 (0.7 g) in dry NMP (6.33 g). The mixture was stirred overnight at room temperature and then poured into deionized water in a beaker. The resultant precipitate was filtered, washed with deionized water, and dried. This dry solid was recrystallized from acetonitrile to afford 0.9 g of product.

Example 34

Preparation of

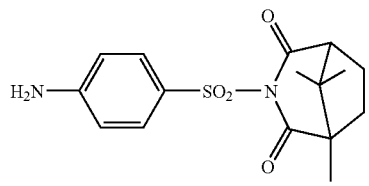

A 3-neck round bottom flask, fitted with a reflux condenser, a thermometer, a pressure-equalizing addition funnel, a magnetic stir bar, and a hose adapter connected to a source of nitrogen gas, was charged with 22.52 g of a 60 weight percent dispersion of NaH in mineral oil. The dispersion was washed three times with heptane by stirring the mixture for several minutes, allowing the mixture to stand, and then using a pipette to remove the supernatant heptane. NMP (32 g) was added to the flask and the mixture was stirred. A solution of camphoric anhydride (11.7 g), sulfanilamide (10 g), and NMP (50 g) was slowly added to the flask using the addition funnel. The mixture was then stirred at room temperature for 24 hours. The mixture was combined with 0.1N aqueous HCl and this mixture was extracted with ethyl acetate. The extract was dried over $MgSO_4$ and the volatile components were removed using a rotary evaporator. This intermediate material was combined with methanesulfonyl chloride (6.98 g), triethylamine (13.51 g), and DMF (82.4 g) in a round bottom flask. The mixture was magnetically stirred for was stirred for 1 hour at 60° C. The mixture was then poured into aqueous 1N HCl within a beaker and the resultant solid was isolated by filtration. The solid was recrystallized from methanol to afford 3 g of product.

Example 35

Preparation of

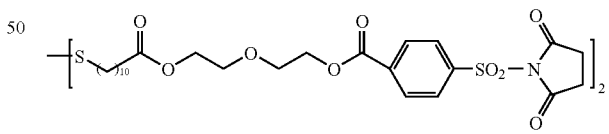

The product of the dithiobis(acid chloride) product of Preparative Example 2 (0.91 g) was added slowly to a solution of the alcohol product of Example 7 (1.5 g) in acetonitrile (9.1 g) within a round bottom flask. The mixture was cooled in an ice bath. As the mixture was magnetically stirred, pyridine (0.33 g) was added slowly. The mixture was stirred overnight after it was allowed to warm to room temperature. The volatile components were removed using a rotary evaporator and the residue was isolated by column chromatography on silica gel by elution with chloroform.

Example 36

Attachment of a N-sulfonyldicarboximide-containing Tethering Groups to a Gold-coated Silicon Substrate A 250 micromolar solution of the dithiobis(N-sulfonyldicarboximide) product of Example 35 in acetone was prepared. A 1 cm by 1 cm portion of a gold-coated silicon wafer was immersed in the solution for 45 minutes. The sample was removed, rinsed sequentially with ethanol and methanol, and dried by directing a stream of nitrogen gas over the treated gold surface for approximately 1 minute. The ellipsometric thickness was 26 Angstroms. The static advancing contact angles of deionized water and of hexadecane on this surface were 49 degrees and 0 degrees, respectively. The measurements were made for the layer of material attached to the gold surface of the s

Example 37

Immobilization of 1-aminododecane with a N-sulfonyldicarboximide Containing Tethering Group Attached to a Gold-coated Silicon Substrate A sample of the gold-coated silicon substrate having attached N-sulfonyldicarboximide containing tethering groups, prepared according to the method of Example 36, was immersed in a 1 millimolar solution of 1-aminododecane in ethanol. After 12 hours, the sample was removed from the solution, rinsed with ethanol, and then dried by directing a stream of nitrogen gas over the surface of the sample for approximately 1 minute. The ellipsometric thickness was 39 Angstroms. The static advancing contact angle of deionized water was 94 degrees. The measurements were made on for the layer attached to the gold surface of the substrate.

Examples 38-44

Immobilization of 1-aminododecane with a N-sulfonyldicarboximide-containing Tethering Group Attached to a Gold-coated Silicon Substrate Eight samples of the N-sulfonyldicarboximide containing tethering groups attached to a gold-coated silicon substrate, prepared according to the method of Example 36, were immersed in a 1 millimolar solution of 1-aminododecane in ethanol. Individual samples were removed from the solution, at the times indicated in Table 1, rinsed with ethanol, and dried by directing a stream of nitrogen gas over the surfaces for approximately 1 minute. The ellipsometric thickness of each sample and static advancing contact angle of deionized water on each sample were determined. The measurements were made on the layer of material attached to the gold surface of the substrate. The data are given in Table 1.

TABLE 1

Examples 38-44

| Example | Time in 1-aminododecane solution (min) | Ellipsometric thickness (Angstroms) | Static advancing contact angle of deionized water (degrees) |
| --- | --- | --- | --- |
| 38 | 0.1 | 28 | 55 |
| 39 | 1 | 29 | 58 |
| 40 | 6 | 30 | 67 |
| 41 | 15 | 31 | 81 |
| 42 | 45 | 32 | 92 |
| 43 | 135 | 39 | 94 |
| 44 | 180 | 38 | 94 |

Examples 45-51

Immobilization of Lysine with a N-sulfonyldicarboximide-containing Tethering Group Attached to a Gold-coated Silicon Substrate Eight samples of the N-sulfonyldicarboximide containing tethering groups attached to a gold-coated silicon substrate, prepared according to the method of Example 36, were immersed in a 1 millimolar solution of lysine in carbonate buffer. Individual samples were removed from the solution, at the times indicated in Table 2, rinsed with deionized water, and dried by directing a stream of nitrogen gas over the surfaces for approximately 1 minute. The ellipsometric thickness of each sample and static advancing contact angle of deionized water on each sample were determined. The measurements were made on the layer of material attached to the gold surface of the substrate. The data are given in Table 2.

TABLE 2

Examples 45-51

| Example | Time in lysine solution (min) | Ellipsometric thickness (Angstroms) | Static advancing contact angle of deionized water (degrees) |
| --- | --- | --- | --- |
| 45 | 0.1 | 28 | 49 |
| 46 | 1 | 29 | 47 |
| 47 | 15 | 33 | 40 |
| 48 | 60 | 34 | 27 |
| 49 | 120 | 39 | 24 |
| 50 | 180 | 37 | 15 |
| 51 | 1440 | 37 | 15 |

Examples 52-55

Immobilization of HSA with a N-sulfonyldicarboximide-containing Tethering Group Attached to a Gold-coated Silicon Substrate Four samples of the N-sulfonyldicarboximide containing tethering groups attached to a gold-coated silicon substrate, prepared according to the method of Example 36, were immersed in a 1 millimolar solution of HSA in carbonate buffer. Individual samples were removed from the solution, at the times indicated in Table 3, rinsed with deionized water, and dried by directing a stream of nitrogen gas over the surfaces for approximately 1 minute. the ellipsometric thickness of each sample was determined. The measurements were made on the layer of material attached to the gold surface of the substrate. The data are giving in Table 3.

TABLE 3

Examples 52–55

| Example | Time in HSA solution (min) | Ellipsometric thickness (Angstroms) |
| --- | --- | --- |
| 52 | 10 | 29 |
| 53 | 30 | 37 |
| 54 | 60 | 47 |
| 55 | 90 | 51 |

Example 56–59

Immobilization of HSA with a N-sulfonyldicarboximide-containing Tethering Group Attached to a Gold-coated Silicon Substrate Four samples of the N-sulfonyldicarboximide containing tethering groups attached to a gold-coated silicon substrate, prepared according to the method of Example 36, were immersed in a 10 micromolar solution of HSA in carbonate buffer. Individual samples were removed from the solution, at the times indicated in Table 4, rinsed with deionized water, and dried by directing a stream of nitrogen gas over the surfaces for approximately 1 minute. The ellipsometric thickness of each sample was determined. The measurements were made on the layer of material attached to the gold surface of the substrate. The data are given in Table 4.

TABLE 4

Examples 56–59

| Example | Time in HSA solution (min) | Ellipsometric thickness (Angstroms) |
| --- | --- | --- |
| 56 | 10 | 45 |
| 57 | 30 | 56 |
| 58 | 60 | 62 |
| 59 | 90 | 64 |

Example 60

Attachment of N-sulfonylsuccinimide-containing Tethering Groups to a Multilayer Polyimide-titanium-gold Substrate A 1 millimolar solution of the disulfide product of Example 25 in acetone was prepared. A sample a polyimide-titanium-gold multilayer substrate, approximately 2.5 cm by 7 cm, the product of Preparative Example 15, was immersed in this solution for 30 minutes, after which time both sides were rinsed with acetone and the sample was dried by directing a stream of nitrogen gas over the treated gold surface for approximately 1 minute.

Example 61

Attachment of N-sulfonylsuccinimide-containing Tethering Groups to a Multilayer DLG-DLC-polyimide-DLC-DLG Substrate A 1 millimolar solution of the trichlorosilane product of Example 11 in methylene chloride was prepared. A sample a DLG-DLC-polyimide-DLC-DLG multilayer substrate, approximately 2.5 cm by 7 cm, the product of Preparative Example 13, was immersed in this solution for 30 minutes, after which time both sides were rinsed with methylene and the sample was dried by directing a stream of nitrogen gas over the treated DLG surface for approximately 1 minute.

Example 62

Attachment of N-sulfonylcamphorimide-containing Tethering Groups to a Polyimide-titanium-gold Substrate A 1 millimolar solution of the disulfide product of Example 32 in acetone was prepared. A sample a polyimide-titanium-gold multilayer substrate, approximately 2.5 cm by 7 cm, the product of Preparative Example 15, was immersed in this solution for 30 minutes, after which time both sides were rinsed with acetone and the sample was dried by directing a stream of nitrogen gas over the treated gold surface for approximately 1 minute.

Example 63

Attachment of N-sulfonylnorborneneimide-containing Tethering Groups to a Polyimide-titanium-gold Substrate A 1 millimolar solution of the disulfide product of Example 26 in acetone was prepared. A sample a polyimide-titanium-gold multilayer substrate, approximately 2.5 cm by 7 cm, the product of Preparative Example 15, was immersed in this solution for 30 minutes, after which time both sides were rinsed with acetone and the sample was dried by directing a stream of nitrogen gas over the treated gold surface for approximately 1 minute.

Example 64

ELISA Using a Multilayer Substrate of Polyimide-titanium-gold having Attached N-sulfonylsuccinimide Containing Tethering Groups A 1 cm by 1 cm sample of the product of Example 60 (a multilayer substrate of polyimide-titanium-gold with attached N-sulfonylsuccinimide containing tethering groups) was placed in a sterile culture tube that contained CHES buffer (1 mL) and the antibody anti-human mouse IgG at a concentration of 50 µg/ml. The tube was shaken on a laboratory shaker for an exposure time of 60 minutes. The buffer was removed from the tube using a pipette and then the substrate immobilized IgG sample was washed three times with PBS buffer that contained 0.05 weight percent TWEEN 20.

To the tube there was then added 1.5 mL of a solution of 2 weight percent nonfat dry milk powder (available under the trade designation "NESTLE CARNATION NONFAT DRY MILK POWDER" from Nestle USA, Glendale, Calif.) in PBS buffer. The tube was placed on the shaker for 1 hour after which time the solution was removed using a pipette and then the sample in the tube was washed three times with PBS buffer that contained 0.05 weight percent TWEEN 20.

A 1 mL aliquot of a solution of biotin-conjugated human IgG in PBS buffer, at a concentration of 4 µg/mL, was then added to the tube. The tube was placed on the shaker for 1 hour after which time the solution was removed using a pipette and then the sample in the tube was washed three times with PBS buffer that contained 0.05 weight percent TWEEN 20. A 1 mL aliquot of a solution of the detecting enzyme SA-HRP in PBS buffer, at a concentration of 0.5 µg/mL, was added to the tube. The tube was placed on the shaker for 30 minutes, after which time the solution was removed using a pipette. Then the sample film was washed three times with PBS buffer that contained 0.05 weight percent TWEEN 20.

A 1 mL aliquot of the ABTS solution was added to the tube and, after 5 minutes, a solution of 1 weight percent aqueous SDS solution (1 mL) was added. An aliquot of the solution in the tube was transferred to a standard cuvette and the absorbance of the solution at 405 nm was measured using a Model 8453 ultraviolet/visible spectrophotometer (available from Hewlett-Packard Co., Palo Alto, Calif.). The absorbance at 405 nm (average of two measurements) was found to be 0.365.

Example 65

ELISA Using a Multilayer Substrate of DLG-DLC-polyimide-DLC-DLG Having Attached N-sulfonylsuccinimide Containing Tethering Groups A 1 cm by 1 cm sample of the product of Example 61 (a multilayer substrate of DLG-DLC-polyimide-DLC-DLG with attached N-sulfonylsuccinimide containing tethering groups) was placed in a sterile culture tube that contained CHES buffer (1 mL) and the antibody anti-human mouse IgG at a concentration of 50 µg/ml. The tube was shaken on a laboratory shaker for an exposure time of 60 minutes. The buffer was removed from the tube using a pipette and then the substrate immobilized IgG sample was washed three times with PBS buffer that contained 0.05 weight percent TWEEN 20.

To the tube there was then added 1.5 mL of a solution of 2 weight percent nonfat dry milk powder (available under the trade designation "NESTLE CARNATION NONFAT DRY MILK POWDER" from Nestle USA, Glendale, Calif.) in PBS buffer. The tube was placed on the shaker for 1 hour after which time the solution was removed using a pipette and then the sample in the tube was washed three times with PBS buffer that contained 0.05 weight percent TWEEN 20.

A 1 mL aliquot of a solution of biotin-conjugated human IgG in PBS buffer, at a concentration of 4 µg/mL, was then added to the tube. The tube was placed on the shaker for 1 hour after which time the solution was removed using a pipette and then the sample in the tube was washed three times with PBS buffer that contained 0.05 weight percent TWEEN 20. A 1 mL aliquot of a solution of the detecting enzyme SA-HRP in PBS buffer, at a concentration of 0.5 µg/mL, was added to the tube. The tube was placed on the shaker for 30 minutes, after which time the solution was removed using a pipette. Then the sample film was washed three times with PBS buffer that contained 0.05 weight percent TWEEN 20.

A 1 mL aliquot of the ABTS solution was added to the tube and, after 5 minutes, a solution of 1 weight percent aqueous SDS solution (1 mL) was added. An aliquot of the solution in the tube was transferred to a standard cuvette and the absorbance of the solution at 405 nm was measured using a Model 8453 ultraviolet/visible spectrophotometer (available from Hewlett-Packard Co., Palo Alto, Calif.). The absorbance at 405 nm (average of two measurements) was found to be 0.287.

Example 66

ELISA Using a Multilayer Substrate of polyimide-titanium-gold Having Attached N-sulfonylnorborneneimide Containing Tethering Groups A 1 cm by 1 cm sample of the product of Example 63 (a multilayer substrate of polyimide-titanium-gold with attached N-sulfonylnorborneneimide containing tethering groups) was placed in a sterile culture tube that contained CHES buffer (1 mL) and the antibody anti-human mouse IgG at a concentration of 50 µg/ml. The tube was shaken on a laboratory shaker for an exposure time of 60 minutes. The buffer was removed from the tube using a pipette and then the substrate immobilized IgG sample was washed three times with PBS buffer that contained 0.05 weight percent TWEEN 20.

To the tube there was then added 1.5 mL of a solution of 2 weight percent nonfat dry milk powder (available under the trade designation "NESTLE CARNATION NONFAT DRY MILK POWDER" from Nestle USA, Glendale, Calif.) in PBS buffer. The tube was placed on the shaker for 1 hour after which time the solution was removed using a pipette and then the sample in the tube was washed three times with PBS buffer that contained 0.05 weight percent TWEEN 20.

A 1 mL aliquot of a solution of biotin-conjugated human IgG in PBS buffer, at a concentration of 4 µg/mL, was then added to the tube. The tube was placed on the shaker for 1 hour after which time the solution was removed using a pipette and then the sample in the tube was washed three times with PBS buffer that contained 0.05 weight percent TWEEN 20. A 1 mL aliquot of a solution of the detecting enzyme SA-HRP in PBS buffer, at a concentration of 0.5 µg/mL, was added to the tube. The tube was placed on the shaker for 30 minutes, after which time the solution was removed using a pipette. Then the sample film was washed three times with PBS buffer that contained 0.05 weight percent TWEEN 20.

A 1 mL aliquot of the ABTS solution was added to the tube and, after 5 minutes, a solution of 1 weight percent aqueous SDS solution (1 mL) was added. An aliquot of the solution in the tube was transferred to a standard cuvette and the absorbance of the solution at 405 nm (average of two measurements) was measured using a Model 8453 ultraviolet/visible spectrophotometer (available from Hewlett-Packard Co., Palo Alto, Calif.). The absorbance at 405 nm was found to be 0.418.

Example 67

ELISA Using a Multilayer Substrate of polyimide-titanium-gold Having Attached N-sulfonylcamphorimide Containing Tethering Groups A 1 cm by 1 cm sample of the product of Example 62 (a multilayer substrate of polyimide-titanium-gold with attached N-sulfonylcamphorimide containing tethering groups) was placed in a sterile culture tube that contained CHES buffer (1 mL) and the antibody anti-human mouse IgG at a concentration of 50 µg/ml. The tube was shaken on a laboratory shaker for an exposure time of 60 minutes. The buffer was removed from the tube using a pipette and then the substrate immobilized IgG sample was washed three times with PBS buffer that contained 0.05 weight percent TWEEN 20.

To the tube there was then added 1.5 mL of a solution of 2 weight percent nonfat dry milk powder (available under the trade designation "NESTLE CARNATION NONFAT DRY MILK POWDER" from Nestle USA, Glendale, Calif.) in PBS buffer. The tube was placed on the shaker for 1 hour after which time the solution was removed using a pipette and then the sample in the tube was washed three times with PBS buffer that contained 0.05 weight percent TWEEN 20.

A 1 mL aliquot of a solution of biotin-conjugated human IgG in PBS buffer, at a concentration of 4 µg/mL, was then added to the tube. The tube was placed on the shaker for 1 hour after which time the solution was removed using a pipette and then the sample in the tube was washed three times with PBS buffer that contained 0.05 weight percent TWEEN 20. A 1 mL aliquot of a solution of the detecting enzyme SA-HRP in PBS buffer, at a concentration of 0.5 µg/mL, was added to the tube. The tube was placed on the shaker for 30 minutes, after which time the solution was removed using a pipette. Then the sample film was washed three times with PBS buffer that contained 0.05 weight percent TWEEN 20.

A 1 mL aliquot of the ABTS solution was added to the tube and, after 5 minutes, a solution of 1 weight percent aqueous SDS solution (1 mL) was added. An aliquot of the solution in the tube was transferred to a standard cuvette and the absorbance of the solution at 405 nm was measured using a Model 8453 ultraviolet/visible spectrophotometer (available from Hewlett-Packard Co., Palo Alto, Calif.). The absorbance at 405 nm (average of two measurements) was found to be 0.568.

Example 68

Capture of *Staphylococcus Aureus* with Immobilized IgG on Multilayer Substrate of DLG-DLC-polyimide-DLC-DLG Rabbit IgG specific to *Staphylococcus aureus* (rabbit anti *Staphylococcus aureus*, obtained from Accurate Chemical & Scientific Corp., Westbury, N.Y.) was used at a concentration of 4.52 mg/mL. This solution was diluted with CHES buffer to give a solution with a concentration of the IgG of 50 µg/mL. A 1 cm by 1 cm sample of the product of Example 61 (N-sulfonylsuccinimide containing tethering group attached to a multilayer substrate of DLG-DLC-polyimide-DLC-DLG) was immersed in this solution for 30 minutes after which time it was washed sequentially with PBS buffer, PBS buffer containing 0.05 weight percent TWEEN 20, and PBS buffer. The sample with immobilized IgG was then allowed to dry in air at room temperature for approximately 1 hour.

A solution of acridine orange in deionized water at a concentration of 10 mg/mL (obtained from Molecular Probes, Inc., Eugene, Oreg.) was diluted to a concentration of 0.1 mg/mL with deionized water. A 500 microliter aliquot of this solution was mixed in a centrifuge tube with a 500 microliter aliquot of a suspension of *Staphylococcus aureus* in deionized water at a concentration of $10^9$ colony forming units per milliliter (cfu/mL). This mixture was allowed to stand at room temperature for 15 minutes, after which time it was mixed using a laboratory vortex mixer and was then centrifuged at 8000 rpm. The supernatant liquid was removed using a pipette and the bacteria were washed three times by adding 500 microliters of deionized water to the tube, mixing the contents using the vortex mixer, centrifuging the tube at 8000 rpm, and removing the supernatant liquid. The bacteria were then dispersed in PBS buffer by adding 500 microliters of buffer to the centrifuge tube and mixing the contents by using the vortex mixer. The concentration of *S. aureus* in the buffer was $10^9$ colony forming units per milliliter ($10^9$ cfu/mL).

The substrate with immobilized IgG was then affixed to a glass microscope slide using double-sided adhesive tape (available from 3M Company, St. Paul, Minn.) and this construction was immersed in the suspension of *S. aureus* in PBS buffer for 1 hour. The sample was then washed sequentially with PBS buffer, PBS buffer containing 0.05 weight percent TWEEN 20, and PBS buffer. The sample was then immersed in a 1 weight percent aqueous solution of paraformaldehyde for 15 minutes, after which time it was washed with deionized water. The sample was analyzed by confocal microscopy using an Olympus Model FV-300 confocal microscope (available from Leeds Precision Inc., Minneapolis, Minn.). The results are shown in FIG. 1.

Comparative Example 3

Figure 2:
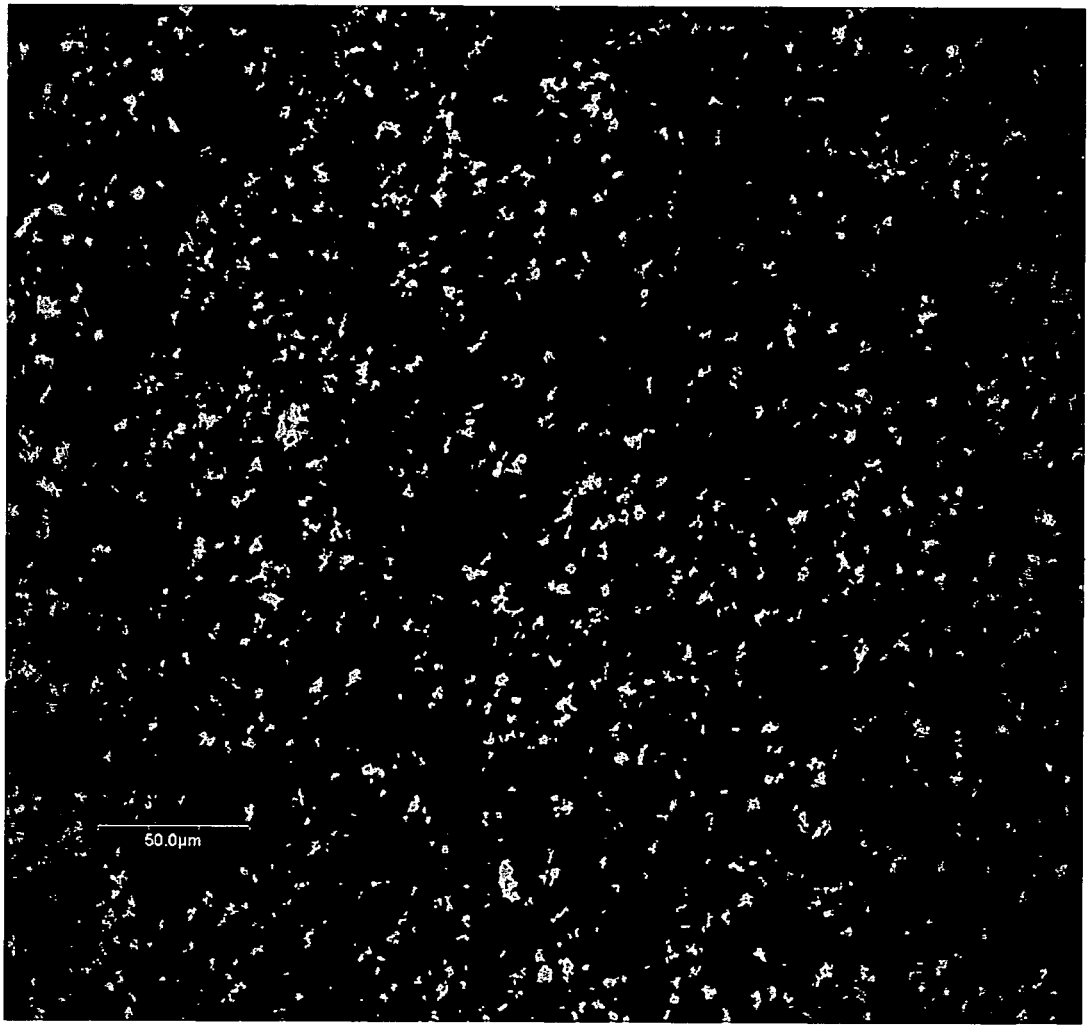
FIG. 2 is a confocal micrograph showing the exposure of a multilayer substrate of diamond-like glass/diamond-like carbon/polyimide/diamond-like carbon/diamond-like glass to *Staphylococcus aureus* in the absence of a tethering group.

Exposure of *Staphylococcus Aureus* to Multilayer Substrate of DLG-DLC-polyimide-DLC-DLG A 1 cm by 1 cm sample of the substrate of Preparative Example 13 (multilayer substrate of DLG-DLC-polyimide film-DLC-DLG) was immersed CHES buffer for 30 minutes after which time it was washed sequentially with PBS buffer, PBS buffer containing 0.05 weight percent TWEEN 20, and PBS buffer. The substrate was then allowed to dry in air at room temperature for approximately 1 hour. The substrate was then immersed in a suspension of *S. aureus* and was then rinsed and immersed in a 1 weight percent aqueous paraformaldehyde solution as described in Example 68. The sample was analyzed by confocal microscopy using an Olympus Model FV-300 confocal microscope (available from Leeds Precision Inc., Minneapolis, Minn.). The results are shown in FIG. 2.

Example 69

Preparation of a Substrate of poly(methylmethacrylate-co-methacrylic Acid) Beads Having Attached N-sulfonylsuccinimide Containing Tethering Groups A mixture of the hydroxyl functionalized poly(methylmethacrylate-co-methacrylic acid) beads of Preparative Example 17 (5.0 g), dry NMP (25.44 g) and the acid chloride product of Example 5 (1.36 g) was stirred overnight at room temperature in a round bottom flask. The mixture was then filtered using a fritted glass funnel and the beads were washed successively with isopropyl alcohol and diethyl ether. The beads were dried by drawing nitrogen gas through them in the fritted glass funnel to constant weight.

Example 70

Preparation of a Substrate of Agarose Beads Having Attached N-sulfonylsuccinimide Containing Tethering Groups Agarose beads (available in isopropyl alcohol under the trade designation "N-HYDROXYSUCCINIMIDYL-SEPHAROSE 4 FAST FLOW" from Sigma-Aldrich Corp, St. Louis, Mo.) (12.5 mL) were placed in a fritted glass funnel and 2-aminoethanol (5 drops) was added. The mixture was stirred and was allowed to stand at room temperature in the funnel for 2 hours. The mixture was then filtered using the funnel and the beads were washed successively with isopropyl alcohol and NMP. The beads were transferred to a screw cap vial and were combined with NMP (5 mL) and the acid chloride product of Example 5 (0.09 g). The vial was sealed and was placed on a two-roll mixer for approximately 16 hours. The mixture was then filtered and the beads were washed with dry isopropyl alcohol to afford the product.

Example 71

Preparation of a Substrate of MBA Beads Having Attached N-sulfonylsuccinimide Containing Tethering Groups The substrate of MBA beads of Preparative Example 18 (0.64 g) were suspended in THF (47 g) in a glass jar. Pyridine (0.04 g) and the acid chloride product of Example 5 (0.16 g) were added and the jar was sealed and was placed on a two-roll mixer for approximately 16 hours. The mixture was then filtered and the beads were washed with THF and were again filtered. The beads were dried first by drawing nitrogen gas through them in the filter funnel and then by using a vacuum oven at 50° C.

Example 72

Immobilization of HSA with a N-sulfonylsuccinimide-containing Tethering Group Attached to Agarose Beads The agarose beads with N-sulfonylsuccinimide containing tethering groups, prepared according to the method of Example 70 (1 mL), were washed with 0.1M bicarbonate buffer having a pH of 9.0 in a centrifuge tube by adding the buffer (1 mL) to the tube, centrifuging the tube, and then decanting the supernatant liquid. These steps were repeated for a total of four washing cycles. A solution of HSA (available from Sigma-Aldrich Co., St. Louis, Mo.) (7.5 mg) in 0.1M bicarbonate buffer having a pH of 9.0 (1 mL) was added to the tube and the mixture was agitated on a standard laboratory rocker-mixer for 2 hours. A solution of ethanolamine (3M in deionized water) was then added to the tube and the mixture was agitated on the rocker for 2 hours. The beads were then washed by centrifuging the tube, decanting the supernatant liquid and then adding PBS buffer having a pH of 7.2 (1 mL), again centrifuging the tube and again decanting the supernatant liquid. This washing with PBS buffer was repeated for a total of four washing cycles. The beads were then washed four times with 0.1M glycine hydrochloride buffer (1 mL) using the centrifuging and decanting procedure, and they were then washed four times with PBS buffer (1 mL) using the same procedure.

The beads were then packed into a 350 microliter glass column with 25 micrometer fritted glass endcaps (available from Omnifit, Ltd., Cambridge, UK) and affinity chromatography was carried out using a liquid chromatograph (available under the trade designation "AKTA FPLC" from Amersham Pharmacia Biotech AB, Uppsala, Sweden) with a flow rate of 0.4 mL per minute of PBS buffer. A solution of goat anti-HSA IgG in PBS buffer (1 mL of a solution having a concentration of 5 mg/mL, available from Sigma-Aldrich Corp., St. Louis, Mo.) was passed through the column. The column was then washed with PBS buffer (4 mL) to elute IgG that was not captured by the beads. The antibody that was captured by the beads was then washed from the column using 0.1M glycine hydrochloride buffer (3.5 mL). The absorbance at 280 nm of each of these solutions was measured and the values were compared to determine that IgG was captured by the beads in the column. The binding capacity of these beads was calculated to be 1.3 mg of IgG per 1 mL of beads.

Example 73

Immobilization of Recombinant Protein A with a N-sulfonylsuccinimide-containing Tethering Group Attached to Agarose Beads The agarose beads with N-sulfonylsuccinimide containing tethering groups, prepared according to the method of Example 70 (1 mL), were washed with 0.1M bicarbonate buffer having a pH of 9.0 in a centrifuge tube by adding the buffer (1 mL) to the tube, centrifuging the tube, and then decanting the supernatant liquid. These steps were repeated for a total of four washing cycles. A solution of recombinant Protein A (available from RepliGen Corp., Waltham, Mass.) (7.5 mg) in 0.1M bicarbonate buffer having a pH of 9.0 (1 mL) was added to the tube and the mixture was agitated on a standard laboratory rocker-mixer for 2 hours. A solution of ethanolamine (3M in deionized water) was then added to the tube and the mixture was agitated on the rocker for 2 hours. The beads were then washed by centrifuging the tube, decanting the supernatant liquid and then adding PBS buffer having a pH of 7.2 (1 mL), again centrifuging the tube and again decanting the supernatant liquid. This washing with PBS buffer was repeated for a total of four washing cycles. The beads were then washed four times with 0.1M glycine hydrochloride buffer (1 mL) using the centrifuging and decanting procedure, and they were then washed four times with PBS buffer (1 mL) using the same procedure.

The beads were then packed into a 350 microliter glass column with 25 micrometer fritted glass endcaps (available from Omnifit, Ltd., Cambridge, UK) and affinity chromatography was carried out using a liquid chromatograph (available under the trade designation "AKTA FPLC" from Amersham Pharmacia Biotech AB, Uppsala, Sweden) with a flow rate of 0.4 mL per minute of PBS buffer. A solution of human IgG in PBS buffer (1 mL of a solution having a concentration of 5 mg/mL, available from Sigma-Aldrich Corp., St. Louis, Mo.) was passed through the column. The column was then washed with PBS buffer (4 mL) to elute IgG that was not captured by the beads. The antibody that was captured by the beads was then washed from the column using 0.1M glycine hydrochloride buffer (3.5 mL). The absorbance at 280 nm of each of these solutions was measured and the values were compared to determine that IgG was captured by the beads in the column. The binding capacity of these beads was calculated to be 11 mg of IgG per 1 mL of beads.

Example 74

Immobilization of HSA with a N-sulfonylsuccinimide-containing Tethering Group Attached to MBA Beads 125 mg of MBA beads with N-sulfonylsuccinimide containing tethering groups, prepared according to the method of Example 71, were added to a solution of HSA (available from Sigma-Aldrich Co., St. Louis, Mo.) (7.5 mg) in 0.1M bicarbonate buffer having a pH of 9.0 (2 mL) and the mixture was agitated on a standard laboratory rocker-mixer for 2 hours. A solution of ethanolamine (3M in deionized water) was then added to the tube and the mixture was agitated on the rocker for 2 hours. The beads were washed by centrifuging the tube, decanting the supernatant liquid and then adding PBS buffer having a pH of 7.2 (1 mL), again centrifuging the tube and again decanting the supernatant liquid. This washing with PBS buffer was repeated for a total of four washing cycles. The beads were then washed four times with 0.1M glycine hydrochloride buffer (1 mL) using the centrifuging and decanting procedure, and they were then washed four times with PBS buffer (1 mL) using the same procedure.

The beads were then packed into a 350 microliter glass column with 25 micrometer fritted glass endcaps (available from Omnifit, Ltd., Cambridge, UK) and affinity chromatography was carried out using a liquid chromatograph (available under the trade designation "AKTA FPLC" from Amersham Pharmacia Biotech AB, Uppsala, Sweden) with a flow rate of 0.4 mL per minute of PBS buffer. A solution of goat anti-HSA IgG in PBS buffer (1 mL of a solution having a concentration of 5 mg/mL, available from Sigma-Aldrich Corp., St. Louis, Mo.) was passed through the column. The column was then washed with PBS buffer (4 mL) to elute IgG that was not captured by the beads. The antibody that was captured by the beads was then washed from the column using 0.1M glycine hydrochloride buffer (3.5 mL). The absorbance at 280 nm of each of these solutions was measured and the values were compared to determine that IgG was captured by the beads in the column. The binding capacity of these beads was calculated to be 1.0 mg of IgG per 1 mL of beads.

Example 75

Immobilization of Recombinant Protein A with a N-sulfonylsuccinimide-containing Tethering Group Attached to MBA Beads 125 mg MBA beads with N-sulfonylsuccinimide containing tethering groups, prepared according to the method of Example 71, were added to a solution of recombinant Protein A (available from RepliGen Corp., Waltham, Mass.) (7.5 mg) in 0.1M bicarbonate buffer having a pH of 9.0 (2 mL) and the mixture was agitated on a standard laboratory rocker-mixer for 2 hours. A solution of ethanolamine (3M in deionized water) was then added to the tube and the mixture was agitated on the rocker for 2 hours. The beads were then washed by centrifuging the tube, decanting the supernatant liquid and then adding PBS buffer having a pH of 7.2 (1 mL), again centrifuging the tube and again decanting the supernatant liquid. This washing with PBS buffer was repeated for a total of four washing cycles. The beads were then washed four times with 0.1M glycine hydrochloride buffer (1 mL) using the centrifuging and decanting procedure, and they were then washed four times with PBS buffer (1 mL) using the same procedure.

The beads were then packed into a 350 microliter glass column with 25 micrometer fritted glass endcaps (available from Omnifit, Ltd., Cambridge, UK) and affinity chromatography was carried out using a liquid chromatograph (available under the trade designation "AKTA FPLC" from Amersham Pharmacia Biotech AB, Uppsala, Sweden) with a flow rate of 0.4 mL per minute of PBS buffer. A solution of human IgG in PBS buffer (1 mL of a solution having a concentration of 5 mg/mL, available from Sigma-Aldrich Corp., St. Louis, Mo.) was passed through the column. The column was then washed with PBS buffer (4 mL) to elute IgG that was not captured by the beads. The antibody that was captured by the beads was then washed from the column using 0.1M glycine hydrochloride buffer (3.5 mL). The absorbance at 280 nm of each of these solutions was measured and the values were compared to determine that IgG was captured by the beads in the column. The binding capacity of these beads was calculated to be 2.2 mg of IgG per 1 mL of beads.

Example 76

Preparation of

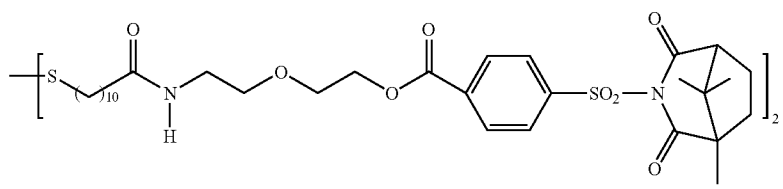

The chlorocarbonyl containing product of Example 31 (0.99 g) was added to a stirred solution of the alcohol product of Preparative Example 3 (0.75 g) in dry NMP (6.97 g). The mixture was magnetically stirred overnight at room temperature and was then poured into deionized water in a beaker. The resultant precipitate was filtered, washed with deionized water, and dried to afford 1.27 g of product.

We claim:
1. A compound according to Formula I:

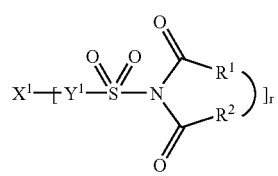

wherein
$X^1$ is a substrate-reactive functional group selected from a halocarbonyl, halocarbonyloxy, mercapto, isocyanato, halosilyl, alkoxysilyl, acyloxysilyl, azido, aziridinyl, disulfide, alkyl disulfide, benzotriazolyl, phosphono, phosphoroamido, or phosphato;
$Y^1$ is a single bond or a divalent group selected from an alkylene, heteroalkylene, arylene, carbonyl, carbonyloxy, carbonylimino, oxy, thio, —$NR^d$— where $R^d$ is hydrogen or alkyl, or combinations thereof;

R¹ and R² together with a dicarboximide group to which they are attached form a four to eight membered heterocyclic or heterobicyclic group that can be fused to an optional aromatic group, optional saturated or unsaturated cyclic group, or optional saturated or unsaturated bicyclic group;

r is equal to 1 when X¹ is a monovalent group or equal to 2 when X¹ is a divalent group; and said compound is unsubstituted or substituted with a halo, alkyl, alkoxy, or combinations thereof.

2. The compound of claim 1, wherein the compound is of formula

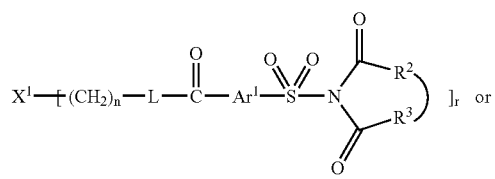

or

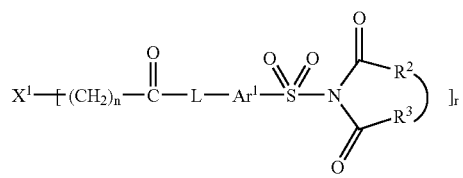

wherein
n is an integer of 1 to 100;
Ar¹ is an arylene; and
L is oxygen or $NR^d$ where $R^d$ is hydrogen or alkyl; and
said compound is unsubstituted or substituted with a halo, alkyl, alkoxy, or combinations thereof.

3. The compound of claim 1, wherein the compound is of formula

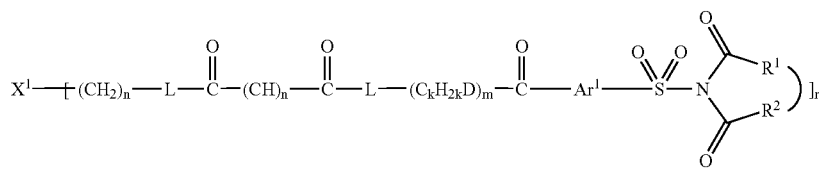

wherein each n is independently an integer of 1 to 100;
m is an integer of 1 to 200;
Ar¹ is an arylene;
k is an integer of 2 to 4;
D is oxygen, sulfur, or NH;
L is oxygen or $NR^d$ where $R^d$ is hydrogen or alkyl; and
said compound is unsubstituted or substituted with a halo, alkyl, alkoxy, or combinations thereof.

4. The compound of claim 1, wherein the compound is of formula

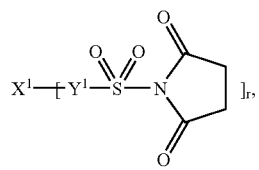

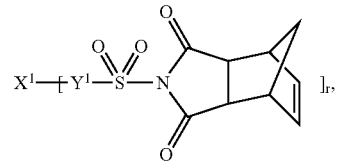

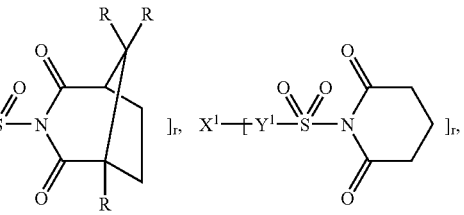

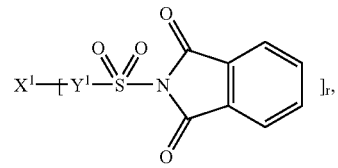

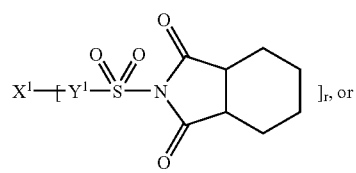

-continued

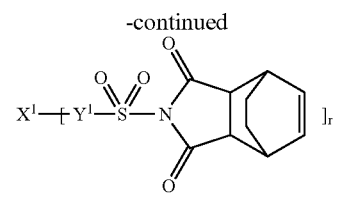

wherein R is an alkyl and said compound is unsubstituted or substituted with a halo, alkyl, alkoxy, or combinations thereof.

5. The compound of claim 1, wherein the compound is of formula

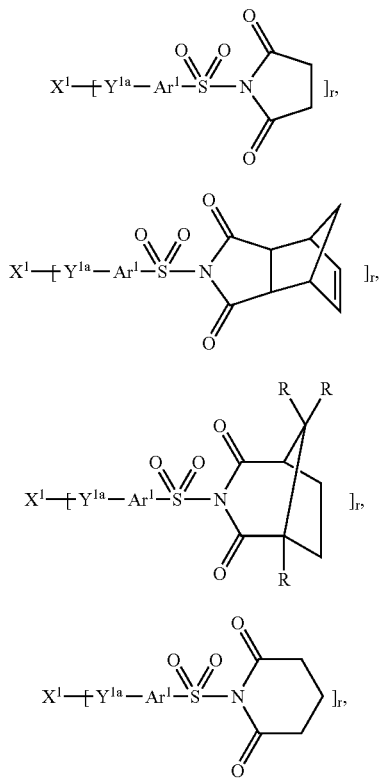
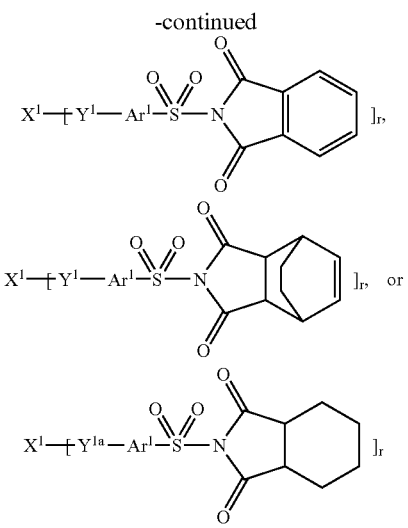

wherein
R is an alkyl;
Ar¹ is an arylene;
$Y^{1a}$ is selected from a single bond, alkylene, heteroalkylene, carbonyl, carbonyloxy, carbonylimino, oxy, thio, —NR$^d$— where R$^d$ is hydrogen or alkyl, or combinations thereof; and
said compound is unsubstituted or substituted with a halo, alkyl, alkoxy, or combinations thereof.

6. The compound of claim 5, wherein Ar¹ is phenylene.

7. A compound is selected from

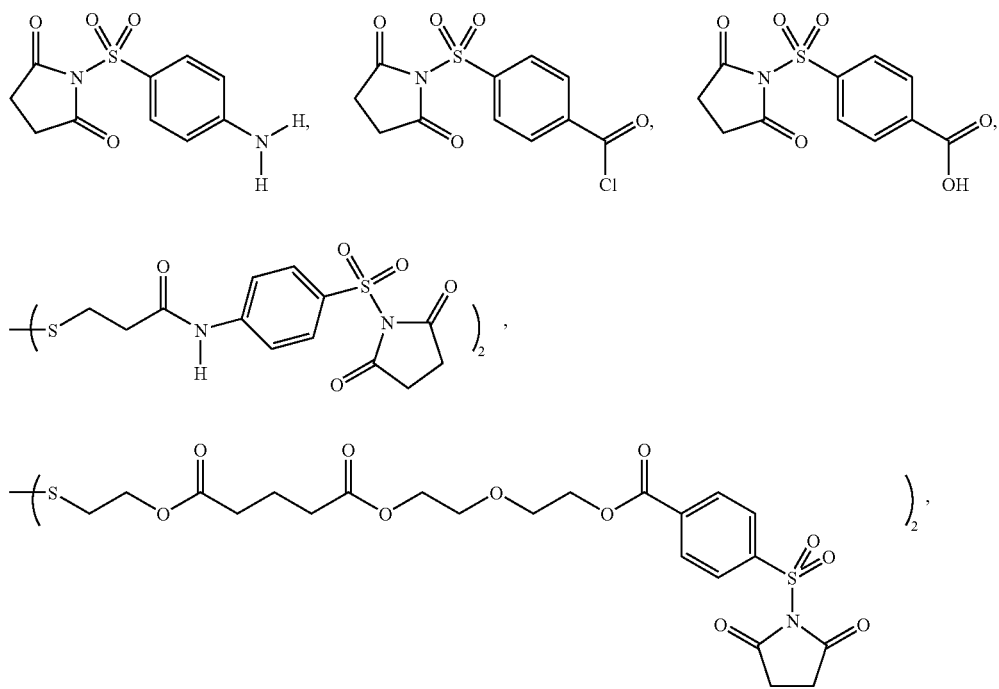

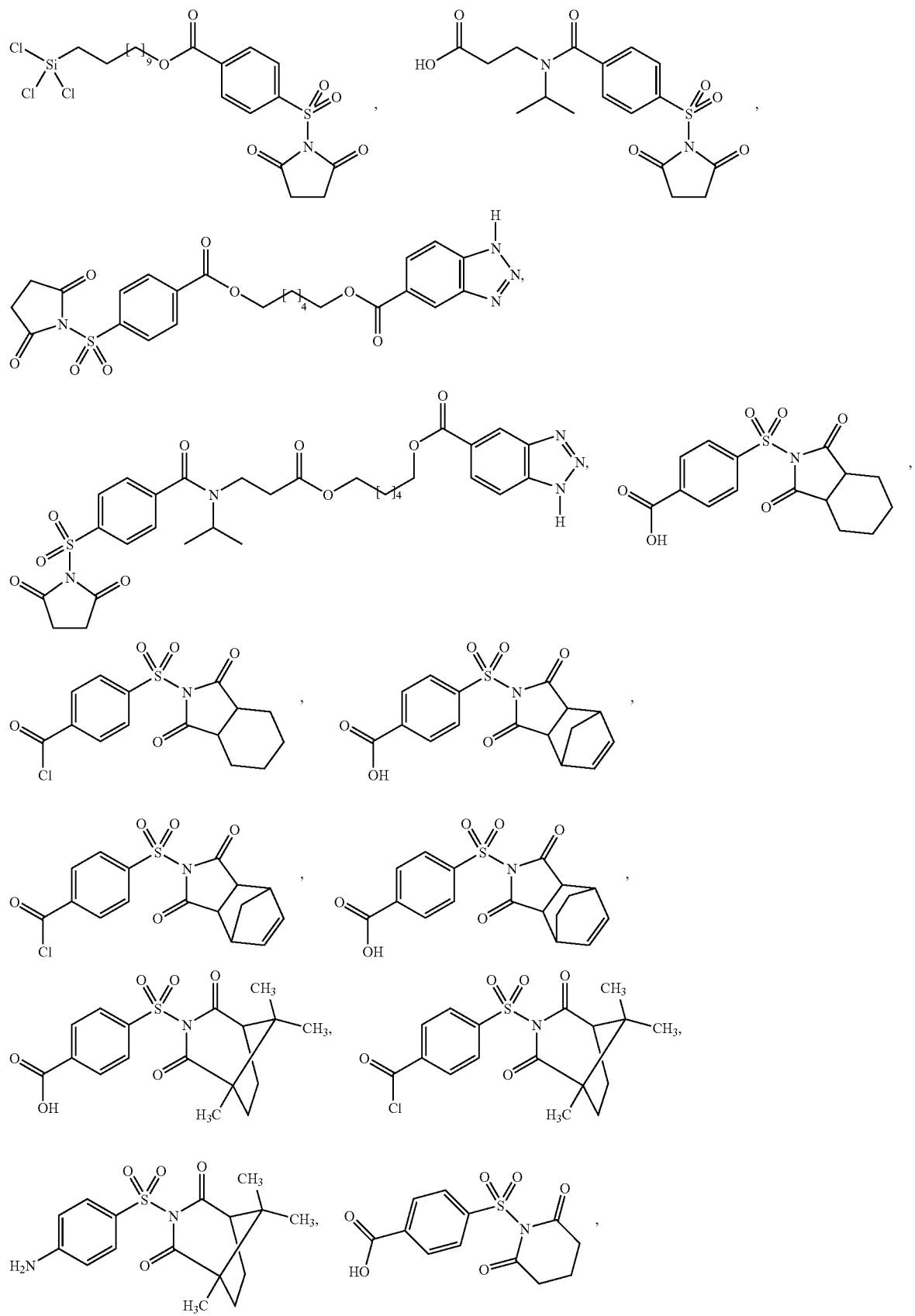

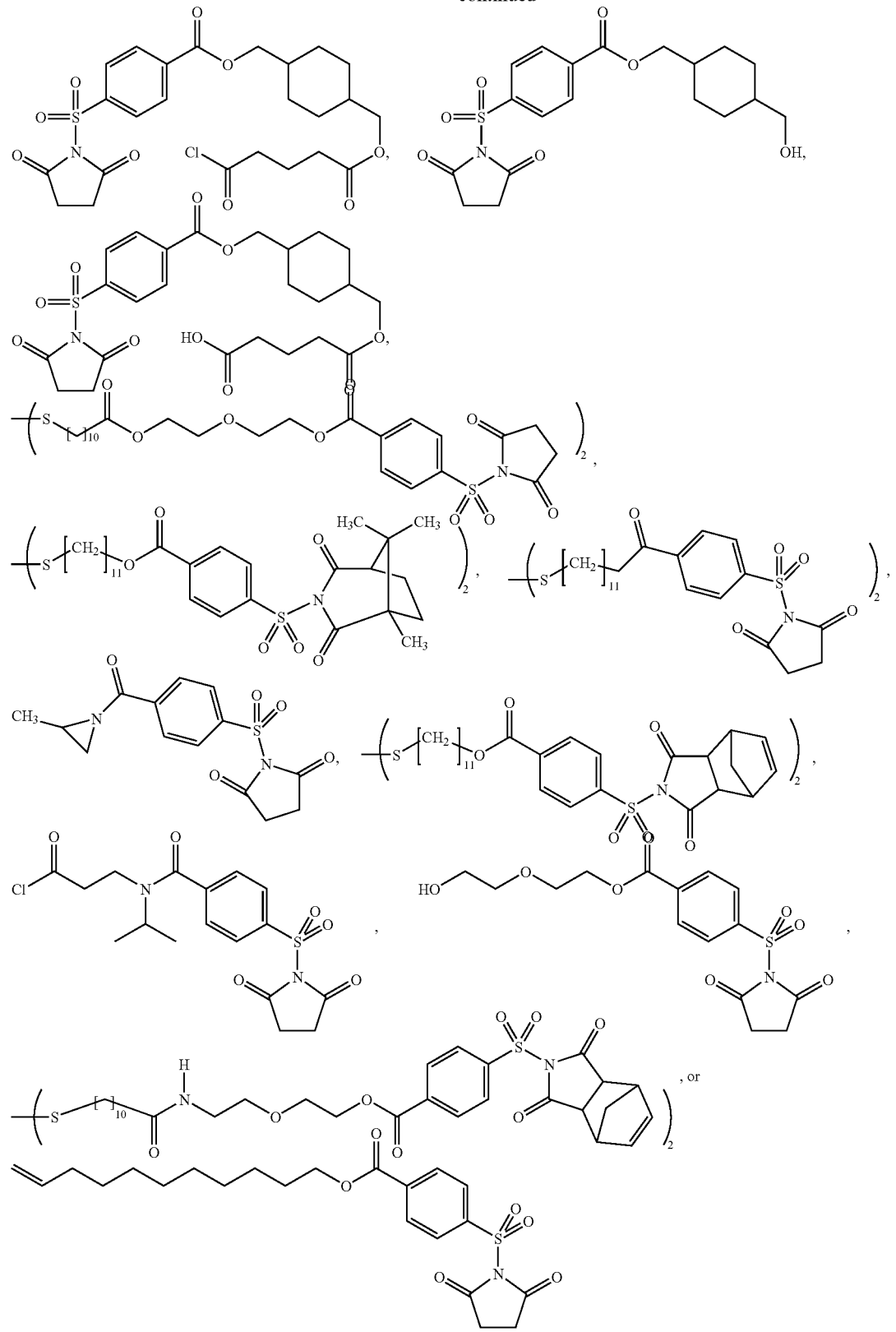
that is unsubstituted or substituted with a halo, alkyl, alkoxy, or combinations thereof.

8. A compound of formula

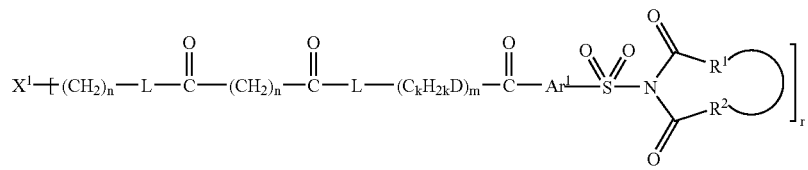

wherein
- $X^1$ is a substrate-reactive functional group selected from a carboxy, halocarbonyl, halocarbonyloxy, cyano, hydroxy, mercapto, isocyanato, halosilyl, alkoxysilyl, acyloxysilyl, azido, aziridinyl, haloalkyl, tertiary amino, primary aromatic amino, secondary aromatic amino, disulfide, alkyldisulfide, benzotriazolyl, phosphono, phosphoroamido, phosphato, and ethylenically unsaturated group;
- $R^1$ and $R^2$ together with a dicarboximide group to which they are attached form a four to eight membered heterocyclic or heterobicyclic group that can be fused to an optional aromatic group, optional saturated or unsaturated cyclic group, or optional saturated or unsaturated bicyclic group;
- r is 1 when $X^1$ is a monovalent group or equal to 2 when $X^1$ is a divalent group;
- each n independently an integer of 1 to 100;
- m is an integer of 1 to 200;
- $Ar^1$ is an arylene;
- k is an integer of 2 to 4;
- D is oxygen, sulfur, or NH;
- L is oxygen or $NR^d$ where $R^d$ is hydrogen or alkyl; and
- said compound is unsubstituted or substituted with a halo, alkyl, alkoxy, or combinations thereof.

* * * * *

UNITED STATES PATENT AND TRADEMARK OFFICE
CERTIFICATE OF CORRECTION

PATENT NO. : 7,361,767 B2
APPLICATION NO. : 10/714053
DATED : April 22, 2008
INVENTOR(S) : Karl E. Benson Page 1 of 1

It is certified that error appears in the above-identified patent and that said Letters Patent is hereby corrected as shown below:

Title Pg, Item (56), Column 2 (Other Publications), Line 18 - Delete "SAMS" and insert -- SAMs --, therefor.

Title Pg, Item (56), Column 2 (Other Publications), Line 27 - Delete ",Anal." and insert -- , Anal. --, therefor.

Column 2, Line 21 - Delete "phosphate" and insert -- phosphato --, therefor.

Column 4, Line 57 - Delete "rad" and insert -- radical --, therefor.

Column 4, Line 57 - Delete "ceters" and insert -- centers --, therefor.

Column 6, Line 58 (Approx.) - Delete "phosphate" and insert -- phosphato --, therefor.

Column 9, Line 17 (Approx.) - Delete "phosphate" and insert -- phosphato --, therefor.

Column 19, Line 65 - After "react" insert -- with --.

Signed and Sealed this

First Day of September, 2009

David J. Kappos
*Director of the United States Patent and Trademark Office*